(12) United States Patent
Dashper et al.

(10) Patent No.: US 8,241,611 B2
(45) Date of Patent: Aug. 14, 2012

(54) BIOFILM TREATMENT

(75) Inventors: Stuart Geoffrey Dashper, Carlton (AU);
Eric Charles Reynolds, Carlton (AU);
Paul David Veith, Carlton (AU); Ching Seng Ang, Preston (AU)

(73) Assignee: Oral Health Austrailia Pty. Ltd., Carlton, Victoria (AU)

( * ) Notice: Subject to any disclaimer, the term of this patent is extended or adjusted under 35 U.S.C. 154(b) by 149 days.

(21) Appl. No.: 12/668,652

(22) PCT Filed: Jul. 11, 2008

(86) PCT No.: PCT/AU2008/001017
§ 371 (c)(1),
(2), (4) Date: Apr. 29, 2010

(87) PCT Pub. No.: WO2009/006699
PCT Pub. Date: Jan. 15, 2009

(65) Prior Publication Data
US 2010/0209362 A1    Aug. 19, 2010

(30) Foreign Application Priority Data
Jul. 12, 2007 (AU) .................. 2007903788

(51) Int. Cl.
*A61K 8/18* (2006.01)
*A61Q 11/00* (2006.01)
(52) U.S. Cl. .................. 424/49; 424/48; 424/50
(58) Field of Classification Search ............... None
See application file for complete search history.

(56) References Cited

U.S. PATENT DOCUMENTS

| | | | |
|---|---|---|---|
| 4,603,112 A | 7/1986 | Paoletti et al. |
| 4,735,801 A | 4/1988 | Stocker |
| 4,837,151 A | 6/1989 | Stocker |
| 5,210,035 A | 5/1993 | Stocker |
| 5,475,097 A | 12/1995 | Travis et al. |
| 5,523,390 A | 6/1996 | Travis et al. |
| 5,707,620 A | 1/1998 | Travis et al. |
| 5,711,937 A | 1/1998 | Nishida et al. |
| 6,129,917 A | 10/2000 | Potempa et al. |
| 6,274,718 B1 | 8/2001 | Travis et al. |
| 6,444,799 B1 | 9/2002 | Ross |
| 6,511,666 B1 | 1/2003 | Reynolds et al. |
| 6,528,038 B1 | 3/2003 | Reynolds et al. |
| 6,576,226 B1 | 6/2003 | Jernberg |
| 6,726,898 B2 | 4/2004 | Jernberg |
| 6,962,706 B1 | 11/2005 | O'Brien-Simpson et al. |
| 7,204,991 B2 | 4/2007 | Barr et al. |
| 7,262,271 B2 | 8/2007 | Reynolds et al. |
| 7,341,727 B1 | 3/2008 | Tucker et al. |
| 7,419,671 B2 | 9/2008 | Reynolds et al. |
| 7,544,777 B2 | 6/2009 | Ross et al. |
| 7,749,502 B2 | 7/2010 | Reynolds et al. |
| 2003/0083287 A1 | 5/2003 | Burgess et al. |
| 2005/0288866 A1 | 12/2005 | Sachdeva et al. |
| 2006/0078950 A1 | 4/2006 | Progulske-Fox et al. |
| 2007/0036734 A1 | 2/2007 | Tahara et al. |
| 2007/0098649 A1 | 5/2007 | Wu et al. |
| 2007/0189981 A1 | 8/2007 | Ross et al. |
| 2008/0175867 A1 | 7/2008 | Reynolds et al. |
| 2010/0034908 A1 | 2/2010 | Ross et al. |
| 2010/0092471 A1 | 4/2010 | Dashper et al. |
| 2010/0297179 A1 | 11/2010 | Dashper et al. |
| 2011/0081358 A1 | 4/2011 | Reynolds et al. |
| 2011/0104179 A1 | 5/2011 | Reynolds et al. |
| 2011/0213129 A1 | 9/2011 | Reynolds et al. |

FOREIGN PATENT DOCUMENTS

| | | |
|---|---|---|
| GB | 2 381 449 | 5/2003 |
| WO | WO 94/27606 | 12/1994 |
| WO | WO 95/07286 | 3/1995 |
| WO | WO 95/09181 A1 | 4/1995 |
| WO | WO 95/11298 | 4/1995 |
| WO | WO 95/26404 A1 | 10/1995 |
| WO | WO 97/34629 A1 | 9/1997 |
| WO | WO 99/29870 | 6/1999 |
| WO | WO 00/67917 A1 | 11/2000 |
| WO | WO 00/75346 A1 | 12/2000 |
| WO | WO 02/102370 A1 | 12/2002 |
| WO | WO 03/055529 A1 | 7/2003 |
| WO | WO 03/080113 A1 | 10/2003 |
| WO | WO 96/17936 A2 | 3/2005 |
| WO | WO 2005/019249 A2 | 3/2005 |
| WO | WO 2008/016385 A2 | 2/2008 |
| WO | WO 2008/124646 A2 | 10/2008 |

OTHER PUBLICATIONS

Supplementary Search Report issued on Feb. 9, 2011 in application No. EP 08 77 2643.
International Search Report issued on Nov. 1, 2005 in application No. PCT/AU2005/001463 (corresponding to US 2009/0175867 and US 2011/0081358).
International Search Report issued on Aug. 17, 2007 in application No. PCT/AU2007/000890 (corresponding to US 2010/0092471).
International Search Report issued on Oct. 13, 2009 in application No. PCT/AU2009/001112 (corresponding to U.S. Appl. No. 13/060,653).
International Search Report issued on Jan. 31, 1997 in application No. PCT/AU96/00673 (corresponding to US 6,511,666 and US 2007/0189982).
International Search Report issued on Jan. 28, 1999 in application No. PCT/AU98/01023 (corresponding to US 7,544,777 and US 2010/0034908).
International Search Report issued on Sep. 12, 2008 in application No. PCT/AU2008/001018 (corresponding to U.S. Appl. No. 12/668,407).

(Continued)

Primary Examiner — Padma Baskar
(74) Attorney, Agent, or Firm — Foley & Lardner LLP

(57) ABSTRACT

The invention provides a method of preventing, inhibiting or reducing a *P. gingivalis* biofilm in a subject comprising administering to the subject a pharmaceutical composition comprising an inhibiting agent of a polypeptide that reduces or inhibits biofilm formation and/or biofilm development. Also provided are compositions useful in the prevention, inhibition or treatment of periodontal disease or *P. gingivalis* infection.

4 Claims, 14 Drawing Sheets

OTHER PUBLICATIONS

International Search Report issued on Sep. 12, 2008 in application No. PCT/AU2008/001017 (corresponding to US 2010/0297179).
Office Action issued on Dec. 27, 2010 by the Examiner in U.S. Appl. No. 12/306,495 (US 2010/0092471).
Office Action issued on Jun. 3, 2010 by the Examiner in U.S. Appl. No. 12/306,495 (US 2010/0092471).
Office Action issued on Mar. 23, 2010 by the Examiner in U.S. Appl. No. 12/306,495 (US 2010/0092471).
Notice of Allowance issued on Dec. 5, 2008 by the Examiner in U.S. Appl. No. 11/589,261 (US 7,544,777).
Office Action issued on May 19, 2008 by the Examiner in U.S. Appl. No. 11/589,261 (US 7,544,777).
Office Action issued on Oct. 30, 2007 by the Examiner in U.S. Appl. No. 11/589,261 (US 7,544,777).
Office Action issued on Apr. 28, 2006 by the Examiner in U.S. Appl. No. 09/581,286.
Office Action issued on Sep. 16, 2005 by the Examiner in U.S. Appl. No. 09/581,286.
Office Action issued on Mar. 24, 2005 by the Examiner in U.S. Appl. No. 09/581,286.
Office Action issued on Aug. 25, 2004 by the Examiner in U.S. Appl. No. 09/581,286.
Office Action issued on Jan. 27, 2004 by the Examiner in U.S. Appl. No. 09/581,286.
Office Action issued on Oct. 1, 2002 by the Examiner in U.S. Appl. No. 09/581,286.
Office Action issued on Nov. 2, 2010 by the Examiner in U.S. Appl. No. 12/382,845 (US 2010/0034908).
Office Action issued on Sep. 17, 2010 by the Examiner in U.S. Appl. No. 11/654,512 (US 2007/0189982).
Office Action issued on Aug. 12, 2009 by the Examiner in U.S. Appl. No. 11/654,512 (US 2007/0189982).
Office Action issued on Oct. 23, 2008 by the Examiner in U.S. Appl. No. 11/654,512 (US 2007/0189982).
Office Action issued on Feb. 7, 2008 by the Examiner in U.S. Appl. No. 11/654,512 (US 2007/0189982).
Office Action issued on Aug. 21, 2007 by the Examiner in U.S. Appl. No. 11/654,512 (US 2007/0189982).
Office Action issued on Oct. 29, 2009 by the Examiner in U.S. Appl. No. 11/729,218 (US 2008/0175867).
Office Action issued on Apr. 10, 2009 by the Examiner in U.S. Appl. No. 11/729,218 (US 2008/0175867).
Office Action issued on Aug. 28, 2008 by the Examiner in U.S. Appl. No. 11/729,218 (US 2008/0175867).
Office Action issued on May 12, 2010 by the Examiner in U.S. Appl. No. 11/663,671 (US 2009/0169568).
Office Action issued on Nov. 4, 2009 by the Examiner in U.S. Appl. No. 11/663,671 (US 2009/0169568).
Office Action issued on Jul. 9, 2010 by the Examiner in U.S. Appl. No. 12/382,845 (US 2010/0034908).
Notice of Allowance issued by the Examiner on Nov. 1, 2011 in U.S. Appl. No. 12/382,845 (US 2010/0034908).
Office Action issued by the Examiner on Nov. 2, 2010 in U.S. Appl. No. 12/382,845 (US 2010/0034908).
Office Action issued by the Examiner on Jul. 9, 2010 in U.S. Appl. No. 12/382,845 (US 2010/0034908).
Rosenstein et al., "Hypothesis: The Humoral Immune Response to Oral Bacteria Provides a Stimulus for the Development of Rheumatoid Arthritis," Inflammation, vol. 28, No. 6, pp. 311-318, 2004.
McGraw et al., "Purification, Characterization, and Sequence Analysis of a Potential Virulence Factor from *Porphyromonas gingivalis*, Peptidylarginine Deiminase," Infection and Immunity, vol. 67, No. 7, pp. 3248-3256, Jul. 1999.
Kyte et al., "A simple method for displaying the hydropathic character of a protein," *Journal of Molecular Biology*, vol. 157, Issue 1, pp. 105-132, May 1982, Abstract.
Aduse Opoku et al., "Characterization, Genetic Analysis, and Expression of a Protease Antigen (PrpRI) of *Porphyromonas gingivalis* W50," *Infection & Immunity*, vol. 63, No. 12, pp. 4744-4754, Dec. 1995.
Barkocy-Gallagher et al., "Analysis of the *prtP* Gene Encoding Porphypain, a Cysteine Proteinase of *Porphyromonas gingivalis*," *J. of Bacteriolgy*, vol. 178, No. 10, May 1996.
Bedi, "Comparative Study of Four Proteases from Spent Culture Media of *Porphyromonas gingivalis* (FAY-19M-1)," *Preparative Biochemistry*, pp. 133-154, Aug. 1995.
Ciborowski, "Purification and Characterization of Two Forms of a High-Molecular-Weight Cysteine Proteinase (Porphypain) from *Porphyromonas gingivalis*," *J. of Bacteriology*, pp. 4549-4557, 1994.
Okamoto et al., "Structural Characterization of Argingipain, a Novel Arginine-Specific Cysteine Proteinase as a Major Periodontal Pathogenic Factor from *Porphyromonas gingivalis*," *Archives of Biochemistry & Biophysics* vol. 316, No. 2, pp. 917-925, Feb. 1, 1995.
Pavloff et al., "Molecular Cloning and Structural Characterization of the Arg-gingipain Proteinase of *Porphyromonas gingivalis*," *J. of Biol. Chem.*, vol. 270, No. 3, pp. 1007-1010, Jan. 20, 1995.
Pike et al., "Lysine- and Arginine-specific Proteinases from *Porphyromonas gingivalis*," *J. of Biol. Chem.*, vol. 269, No. 1, pp. 406-411, Jan. 7, 1994.
Slakeski et al., "Characterization of a *Porphyromnas gingivalis* Gene prtR That Encodes an Arginine-Specific Thiol Porteinase and Multiple Adhesins," *Biochem. & Biophys. Res. Comm.*, vol. 224, pp. 605-610, 1996.
Yoshimura, "Characterization of a Trypsin-Like Protease From the Bacterium Bacteroides *Gingivalis* Isolated From Human Dental Plaque," *Archs. Oral. Biol.*, vol. 29, No. 7, pp. 559-564, 1984.
Albandar et al., Destructive periodontal disease in adults 30 years of age and older in the United States, 1988-1994, Journal of Periodontology, vol. 70, pp. 13- 29, 1999.
Alm et al., The MicrobesOnline Web site for comparative genomics, Genome Research, vol. 15, pp. 1015-1022, 2005.
Bramanti et al. Roles of porphyrins and host iron transport proteins in regulation of growth of *Porphyromonas gingivalis* W50, Journal of Bacteriology, vol. 173, pp. 7330-7339, 1991.
Brochu et al., Acquisition of iron from human transferrin by *Porphyromonas gingivalis*: a role for Arg-and Lys-gingipain activities, Oral Microbiology and Immunology, vol. 16, pp. 79-87, 2001.
Capestany et al., Role of the *Poiphyromonas gingivalis* InlJ Protein in Homotypic and Heterotypic Biofilm Develdpment, Infection and Immunity, vol. 74, pp. 3002-3005, 2006.
Carter et al., Humanization of an Anti-p185HER2 Antibody for Human Cancer Therapy, Proceedings of the National Academy of Science USA, vol. 89, pp. 4285-4289, 1989.
Chen et al., *Porphyromonas gingivalis* gingipains and adhesion to epithelial cells, Infection and Immunity, vol. 69, pp. 3048-3056, 2001.
Cossart et al., Bacterial invasion: the paradigms of enteroinvasive pathogens, Science, vol. 304, pp. 242-248, 2004.
Curtiss et al., A virulent Salmonella typhimurium Acya Acrp oral vaccine strains expressing a *Streptococcal* colonization and virulence antigen, Vaccine, vol. 6, pp. 155-160, 1988.
Dashper et al., Characterization of a novel outer membrane herninbinding protein of *Porphyromonas gingivalis*, Journal of Bacteriololgy., vol. 182, pp. 6456-6462, 2000.
Dashper et al., Sodium ion-driven serine/threonine transport in *Porphyromonas gingivalis*, Journal of Bacteriology, vol. 183, pp. 4142-4148, 2001.
Dashper et al., Hemoglobin hydrolysis and haem acquisition by *Porphyromonas gingivalis*, Oral Microbiology and Immunology, vol. 9,. pp. 50-56, 2004.
Dashper et al., A novel *Porphyromonas gingivalis* FeoB plays a role in manganese accumulation, The Journal of Biological Chemistry, vol. 280, pp. 28095-28102, 2005.
Database Ref. Seq, Accession Nos. NC_002950.2 and N13_904903, Jan. 12, 2009.
Devereaux et al., A comprehensive set of sequence analysis programs for the VAX, Nucleic Acids Research, vol. 12, pp. 387-395, 1984.
Diaz et al., The effect of oxygen on the growth and physiology of *Porphyromonas gingivalis*, Oral Microbiology and Immunology, vol. 19, pp. 88-94, 2004.
Diaz et al., Role of oxyR in the oral anaerobe *Porphyromonas gingivalis*, Journal of Bacteriology, vol. 188, pp. 2454-2462, 2006.

Dramsi et al., Entry of Listeria monocytogenes into hepatoeytes requires expression of in inIB, a surface protein of the internalin multigene family, Molecular Microbiology, vol. 16, pp. 251-261, 1995.

Duran-Pinedo et al., The RprY response regulator of *Porphyromonas gingivalis*, Molecular Microbiology, vol. 64, pp. 1416, 2007.

Eymann et al., A comprehensive proteome map of growing *Bacillus subtilis* cells, Proteomics, vol. 4, pp. 2849-2876, 2004.

Fletcher et al., Virulence of a *Porphyramonas gingivalis* W83 mutant defective in the prtH gene, Infection and Immunity, vol. 63, pp. 1521-1528, 1995.

Genco et al., Characterization of a Tn4351—generated hemin uptake mutant of *Porphyramonas gingivalis*: evidence for the coordinate regulation of virulence factors by hemin, Infection and Immunity, vol. 63, pp. 2459-2466, 1995.

Guina et al., Quantitative proteomic analysis indicates increased synthesis of a quinolone by *Pseudomonas aeruginosa* isolates from cystic fibrosis airways, Proceedings of the National Academy of Science USA, vol. 100, pp. 2771-2776, 2003.

Haffajee et al., Microbial etiological agents of destructive periodontal diseases, Periodontology 2000, vol. 5, pp. 78-111, 1994.

Huse et al., Generation of a large combinatorial library of the immunoglobulin repertoire in phage lambda, Science, vol. 246, pp. 1275-1281, 1989.

Jones et al., Replacing the complementarity-determining regions in a human antibody with those from a mouse, Nature, vol. 321, pp. 522-525, 1986.

Lamont et aL, Interaction of *Porphyromonas gingivalis* with gingival epithelial cells maintained in culture, Oral Microbiology and Immunology, vol. 7, pp. 364-367, 1992.

Lamont et al., *Porphyromonas gingivalis* invasion of gingival epithelial cells, Infection and Immunity, vol. 63, pp. 3878-3885, 1995.

Li et al., Protein profiling with cleavable isotope-coded affinity tag (cICAT) reagents: the yeast salinity stress response, Molecular and Cellular Proteomics, vol. 2, pp. 1198-1204, 2003.

Marino et al., A framework for interpreting the leucine-rich repeats of the Listeria internalins, Proceedings of the National Academy of Science USA, vol. 97, pp. 8784-8788, 2000.

McKee et al., Effect of hemin on the physiology and virulence of *Bacteroides gingivalis* W50, Infection and Immunity, vol. 52, pp. 349-355, 1986.

Moore et al., The bacteria of periodontal diseases, Periodontology 2000, vol. 5, pp. 66-77, 1994.

Needleman et al., A general method applicable to the search for similarities in the amino acid sequence of two proteins, Journal of Molecular Biology, vol. 48, pp. 443-453, 1970.

Okano et al., Proteomics-based analysis of a counter-oxidative stress system in *Porphyromonas gingivalis*, Proteomics, vol. 6, pp. 251-258, 2006.

Park et al., Identification of *Porphyromonas gingivalis* genes specifically expressed in human gingival epithelial cells by using differential display reverse transcription-PCR, Infection and Immunity, vol. 72, pp. 3752-3758, 2004.

Pathirana et al., Flow cytometric analysis of adherence of *Porphyromonas gingivalis* to oral epithelial cells, Infection and Immunity, vol. 75, pp. 2484-2492, 2007.

Peng et al., Evaluation of multidimensional chromatography coupled with tandem mass spectrometry (LC/LC-MS/MS) for large-scale protein analysis: the yeast proteome, Journal of Proteome Research, vol. 2, pp. 43- 50, 2003.

Price et al., A novel method for accurate operon predictions in all sequenced prokaryotes, Nucleic Acids Research, vol. 33, pp. 880-892, 2005.

Reichmann et al., Reshaping human antibodies for therapy, Natu e, vol. 332, pp. 323-327, 1988.

Ross et al., Identification of vaccine candidate antigens from a genomic analysis of *Porphyromonas gingivalis*, Vaccine, vol. 19, pp. 4135-4142, 2001.

Sabet et al., LPXTG protein In1J, a newly identified internalin involved in Listeria monocytogenes' virulence, Infection and Immunity, vol. 73, pp. 6912-6922, 2005.

Schifferle et al., Effect of protoporphyrin DC limitation on *Porphyromonas gingivalis*, Journal of Endodonics, vol. 22, pp. 352-355, 1996.

Schramm et al., Nucleotide sequence of the colicin B activity gene cba: consensus pentapeptide among TonB-dependent colicins and receptors, Journal of Bacteriology, vol. 169, pp. 3350-3357, 1987.

Schubert et al., Structure of internalin, a major invasion protein of Listeria monocytogenes, in complex with its human receptor E-cadherin, Cell, vol. 111, pp. 825-836, 2002.

Seers et al, The RgpB C-terminal domain has a role in attachment of RgpB to the outer membrane and belongs to a novel C-terminal-domain family found in *Porphyromonas gingivalis*, Journal of Bacteriology, vol. 188, pp. 6376-6386, 2006.

Shah et al., The porphyrin pigmentation of subspecies of *Bacteroides melaninogenicus*, Biochemical Journal, vol. 180, pp. 45-50, 1979.

Sharp et al., The codon Adaptation Index-a measure of directional synonymous codon usage bias, and its potential applications, Nucleic Acids Research, vol. 15, pp. 1281-1295, 1987.

Shi et al., Genetic analyses of proteolysis, hemoglobin binding, and hemagglutination of *Porphyromonas gingivalis*. Construction of mutants with a combination of rgpA, rgpl3, kgp, and hagA, The Journal of Biological Chemistry, vol. 274, pp. 17955-17604, 1999.

Shizukuishi et al., Effect of concentration of compounds containing iron on the growth of *Porphyromonas gingivalis*, FEMS Microbiology Letters, vol. 131, pp. 313-317, 1995.

Simpson et al., Characterization and expression of HmuR, a TonI3-dependent hemoglobin receptor of *Porphyromonas gingivalis*, Journal of Bacteriology, vol. 182, pp. 5737-5748, 2000.

Smalley et al. Hacinin-binding proteins of *Porphyromonas gingivalis* W50 grown in a chemostat under haemin-1 imitation. Journal of General Microbiology, 1993, vol. 139, pp. 2145-2150.

Smalley et al., The periodontopathogen *Porphyromonas gingivalis* binds iron protoporphyrin IX in the mu-oxo dimeric form: an oxidative buffer and possible pathogenic mechanism, Biochemical Journal, vol. 331 (Pt3), pp. 681-685, 1998.

Smalley et al., The periodontal pathogen *Porphyromonas gingivalis* harnesses the chemistry of the mu-oxo bishaem of iron protoporphyrin IX to protect against hydrogen peroxide, FEMS Microbiology Letters, vol. 183, pp. 159-164, 2000.

Supek et al., INCA: synonymous codon usage analysis and clustering by means of self-organizing map, Bioinformatics, vol. 20, pp. 2329-2330, 2004.

Thompson et al., Clustal W: improving the sensitivity of progressive multiple sequence alignment through sequence weighting, position-specific gap penalties and weight matrix choice, Nucleic Acids Research, vol. 22, pp. 4673-4680, 1994.

Tribble et al., A *Porphyromonas gingivalis* haloacid dehalogenase family phosphatase interacts with human phosphoproteins and is important for invasion, Proceedings of the National Academy of Science USA, vol. 103, pp. 11027-11032, 2006.

Veith et al., Identification of a novel heterodimeric outer membrane protein of *Porphyromonas gingivalis* by two- dimensional gel electrophoresis and peptide mass fingerprinting, European Journal of Biochemistry, vol. 268, pp. 4748-4757, 2001.

Wang et al., An analysis of the proteomic profile for *Thermoanaerobacter tengcongensis* under optimal culture conditions, Proteomics, vol. 4, pp. 136-150, 2004.

Washburn et al., Large-scale analysis of the yeast proteome by multidimensional protein identification technology, Nature Biotechnology, vol. 19, pp. 242-247, 2001.

Yu et al., Predicting subcellular localization of proteins for Gram-negative bacteria by support vector machines based on n-peptide compositions, Protein Science, vol. 13, pp. 1402-1406, 2004.

Zhang et al., Differential protein expression by *Porphyromonas gingivalis* in response to secreted epithelial cell components, Proteomics, vol. 5, pp. 198-211, 2005.

Houghten et al., "Relative Importance of Position and Individual Amino Acid Residues in Peptide Antigen-Antibody Interactions: Implications in the Mechanism of Antigenic Drift and Antigenic Shift Vaccines," 1986, Fred Brown, Ed.

Lederman et al., "A Single Amino Acid Substitution in a Common African Allele of the CD4 Molecule Ablates Binding of the Monoclonal Antibody, OKT4," Molecular Immunology, vol. 28, pp. 1171-1181, 1991.

Li et al., "β-Endorphin omission analogs: Disssociation of immunoreactivity from other biological activities," Proc. Natl. Acad. Sci. USA, vol. 77, pp. 3211-3214, 1980.

Campbell, "Assay Techniques," Monoclonal Antibody Technology, Chapter 2, 1986.

Bohgal et al., "A cell-associated protein complex of *Porphyromonas gingivalis* W50 composed of Arg- and Lys-specific cysteine proteinases and adhesins," Microbiology, vol. 143, pp. 2485-2495, 1997.

O'Brien-Simpson et al., "RgpA-Kgp Peptide-Based Immunogens Provide Protection Against *Porphyromonas gingivalis* Challenge in Murine Lesion Model," Infection and Immunity, 68(7): 4055-4063, 2000.

Hu et al., "Coptidis rhizome inhibits growth and proteases of oral bacteria," Oral Diseases, vol. 6, No. 5, pp. 297-302, Sep. 1, 2000.

Dashper et al., "Inhibition of *Porphyromonas gingivalis* biofilm by oxante," Antimicrobial Agents and Chemotherapy, vol. 54, No. 3, pp. 1311-1314, Mar. 1, 2010.

Davey et al., "Enhanced Biofilm Formation and Loss of Capsule Synthesis: Deletion of a Putative Glycosyltransferase in *Porphyromonas gingivalis*," J. Bacteriology, (2006), 188(15):5510-5523.

Chung et al., "Indentification of a *Porphyromonas gingivalis* Receptor for the *Streptococcus gordonii* SspB Protein", Infection and Immunity (2000), 68(12) 6758-6762.

Xie, et al., "*Porphyromonas gingivalis* Genes Involved in *fimA* Regulation", Infection and Immunity (2004), 72(2) 651-658.

Daep et al., "Structural Characterization of Peptide-Mediated Inhibition of *Porphyromonas gingivalis* Biofilm Formation," *Infection and Immunity* (2006), 74(10):5756-5762.

Mendz et al., "Fumarate Reductase: A Target for Therapeutic Intervention against *Helicobacter pylori*," Archives of Biochemistry and Biophysics (1995), 321(1):153-159.

Nelson et al., "Complete Genome Sequence of the Oral Pathogenic Bacterium *Porphyromonas gingivalis* Strain W83," *J. Bacteriol.* (2003), 185(18):5591-5601, American Society for Microbiology.

Takahashi, et al., "Metabolic Pathways for Cytotoxic End Product Formation from Glutamate- and Aspartate-Containing Peptides by *Porphyromonas gingivalis*," J. Bacteriol. (2000), 182(17):4704-4710.

(1 : 1)    (2 : 1)    (1 : 5)    (10 : 1)

BIOFILM TREATMENT

CROSS REFERENCE TO RELATED APPLICATIONS

This application is a 35 USC §371 National Stage application of International Application No. PCT/AU2008/001017 filed Jul. 11, 2008, now pending; which claims the benefit under 35 USC §119(a) to Australia Application Serial No. 2007903788 filed Jul. 12, 2007. The disclosure of each of the prior applications is considered part of and is incorporated by reference in the disclosure of this application.

FIELD OF THE INVENTION

The present invention relates to compositions and methods for preventing or altering bacterial biofilm formation and/or development such as those containing *Porphyromonas gingivalis*. In particular the present invention relates to the use and inhibition of polypeptides which are important for growth as a biofilm or under haem-limitation or to modulate biofilm formation and/or development. The present invention also relates to a composition for the modulation of biofilm formation and/or development, including by regulating bacterial enzymes.

BACKGROUND OF THE INVENTION

Many bacterial treatments are directed to bacteria in a planktonic state. However, bacterial pathologies include bacteria in a biofilm state. For example, *Porphyromonas gingivalis* is considered to be the major causative agent of chronic periodontal disease. Tissue damage associated with the disease is caused by a dysregulated host immune response to *P. gingivalis* growing as a part of a polymicrobial bacterial biofilm on the surface of the tooth. Bacterial biofilms are ubiquitous in nature and are defined as matrix-enclosed bacterial populations adherent to each other and/or to surfaces or interfaces (1). These sessile bacterial cells adhering to and growing on a surface as a mature biofilm are able to survive in hostile environments which can include the presence of antimicrobial agents, shear forces and nutrient deprivation.

The Centers for Disease Control and Prevention estimate that 65% of human bacterial infections involve biofilms. Biofilms often complicate treatment of chronic infections by protecting bacteria from the immune system, decreasing antibiotic efficacy and dispersing planktonic cells to distant sites that can aid reinfection (2,3). Dental plaque is a classic example of a bacterial biofilm where a high diversity of species form a heterogeneous polymicrobial biofilm growing on the surface of the tooth. The surface of the tooth is a unique microbial habitat as it is the only hard, permanent, non-shedding surface in the human body. This allows the accretion of a substantial bacterial biofilm over a lengthy time period as opposed to mucosal surfaces where epithelial cell shedding limits development of the biofilm. Therefore, the changes to the *P. gingivalis* proteome that occur between the planktonic and biofilm states are important to our understanding of the progression of chronic periodontal disease.

*P. gingivalis* has been classified into two broad strain groups with strains including W50 and W83 being described as invasive in animal lesion models whilst strains including 381 and ATCC 33277 are described as less invasive (4,5). Griffen et al. (6) found that W83/W50-like strains were more associated with human periodontal disease than other *P. gingivalis* strains, including 381-like strains, whilst Cutler et al. (7) demonstrated that invasive strains of *P. gingivalis* were more resistant to phagocytosis than non-invasive strains. Comparison of the sequenced *P. gingivalis* W83 strain to the type strain ATCC 33277 indicated that 7% of genes were absent or highly divergent in strain 33277 indicating that there are considerable differences between the strains (8). Interestingly *P. gingivalis* strain W50 forms biofilms only poorly under most circumstances compared to strain 33277 which readily forms biofilms (9). As a consequence of this relatively few studies have been conducted on biofilm formation by *P. gingivalis* W50.

Quantitative proteomic studies have been employed to determine proteome changes of human bacterial pathogens such as *Pseudomonas aeruginosa*, *Escherichia coli* and *Streptococcus mutans* from the planktonic to biofilm state using 2D gel electrophoresis approaches, where protein ratios are calculated on the basis of gel staining intensity (10-12). An alternative is to use stable isotope labelling techniques such as ICAT, iTRAQ or heavy water ($H_2^{18}O$) with MS quantification (13). The basis for $H_2^{18}O$ labelling is that during protein hydrolysis endopeptidases such as trypsin have been demonstrated to incorporate two $^{18}O$ atoms into the C-termini of the resulting peptides (14,15). In addition to use in the determination of relative protein abundances (16-19), $^{18}O$ labelling in proteomics has also been used for the identification of the protein C-terminus, identification of N-linked glycosylation after enzymatic removal of the glycan, simplification of MS/MS data interpretation and more recently for validation of phosphorylation sites (20-23). The $^{16}O/^{18}O$ proteolytic labelling method for measuring relative protein abundance involves digesting one sample in $H_2^{16}O$ and the other sample in $H_2^{18}O$. The digests are then combined prior to analysis by LC MS/MS. Peptides eluting from the LC column can be quantified by measuring the relative signal intensities of the peptide ion pairs in the MS mode. The incorporation of two $^{18}O$ atoms into the C-terminus of digested peptides by trypsin results in a mass shift of +4 m/z allowing the identification of the isotope pairs.

Due to the complexity of the proteome, prefractionation steps are advantageous for increasing the number of peptide and protein identifications. Most prefractionation steps involve a 2D LC approach at the peptide level after in-solution digestion (24,25). However due to potential sample loss during the initial dehydration steps of the protein solution, SDS PAGE prefractionation at the protein level followed by $^{16}O/^{18}O$ labelling during in gel digestion has also been carried out successfully, (26-29). The $^{16}O/^{18}O$ proteolytic labelling is a highly specific and versatile methodology but few validation studies on a large scale have been performed (30). An excellent validation study was carried out by Qian et al (18) who labelled two similar aliquots of serum proteins in a 1:1 ratio and obtained an average ratio of 1.02±0.23 from 891 peptides. A more recent study by Lane et al (26) further demonstrated the feasibility of the $^{16}O/^{18}O$ method using a reverse labelling strategy to determine the relative abundance of 17 cytochrome P450 proteins between control and cytochrome P450 inducers treated mice that are grafted with human tumours.

SUMMARY OF THE INVENTION

This invention used a system whereby *P. gingivalis* W50 is grown in continuous culture and a mature biofilm developed on the vertical surfaces in the chemostat vessel over an extended period of time. The final biofilm is similar to that which would be seen under conditions of disease progression, thus allowing a direct comparison between biofilm and planktonic cells. $^{16}O/^{18}O$ proteolytic labelling using a reverse labelling strategy was carried out after SDS-PAGE prefractionation of the *P. gingivalis* cell envelope fraction followed by coupling to off-line LC MALDI TOF-MS/MS for identification and quantification. Of the 116 proteins identified, 81 were consistently found in two independent continuous culture studies. 47 proteins with a variety of functions were found to consistently increase or decrease in abundance in the biofilm cells providing potential targets for biofilm control strategies. Of these 47 proteins the present inventors have selected 24 proteins which they believe are particular useful as targets in treatment and/or prevention of *P. gingivalis* infection. These are listed in Table 4 below.

Accordingly, the present invention provides an isolated, purified, or recombinant bacterial polypeptide that modulates biofilm formation by bacteria. Preferably, the bacteria are anaerobic. In one embodiment, the bacteria are fumarate reductase (Frd) dependent, such as those of genus *Porphyromonas*. A preferred bacterium is *P. gingivalis*.

Polypeptides according to the invention for *P. gingivalis* have an amino acid sequence selected from the group consisting of sequences listed in Table 4. The invention extends to sequences at least 80% identical thereto, preferably 85%, 90%, 95%, 96%, 97%, 98%, or 99%.

Another aspect of the invention is a method of preventing or treating a subject for *P. gingivalis* infection comprising administering to the subject a pharmaceutical composition comprising an inhibiting agent of a polypeptide that modulates biofilm formation, particularly a *P. gingivalis* infection resulting from or associated with bacterial biofilm formation. Also provided is a method of preventing or treating a subject for periodontal disease comprising administering to the subject a pharmaceutical composition comprising an inhibiting agent of a polypeptide that modulates biofilm formation, particularly periodontal disease resulting from or associated with bacterial biofilm formation. Typically, the polypeptide is important or necessary for biofilm development in the sense that inhibition of the activity of the polypeptide reduces or inhibits biofilm formation and/or development.

Also provided is use of an inhibiting agent of a polypeptide that modulates biofilm formation in the manufacture of a medicament for preventing or treating periodontal disease.

Another aspect of the invention is a composition useful in the prevention or treatment of periodontal disease, the composition comprising an inhibiting agent such as an antagonist, or combination of antagonists of the polypeptide of the first aspect of the present invention. Typically, the composition will also include a pharmaceutically acceptable carrier. The composition is administered so that the antagonist(s) inhibits infection.

Optionally, the composition may further include one or more antibiotics that are toxic to or inhibit the growth of Gram negative anaerobic bacteria. Potentially any bacteriostatic or bactericidal antibiotic may be used in a composition of the invention. Preferably, suitable antibiotics include amoxicillin, doxycycline or metronidazole.

Another aspect of the invention is a composition useful in the prevention, inhibition or treatment of periodontal disease or *P. gingivalis* infection for use in the oral cavity.

Another aspect of the invention is a composition useful in the prevention, inhibition or treatment of periodontal disease or *P. gingivalis* infection when used in the oral cavity.

An oral composition may be deposited on teeth or on the gums or both.

The polypeptide may be an enzyme. Preferably the enzyme is involved in organic acid metabolism, more preferably glutamate/aspartate catabolism. In one embodiment, the polypeptide is fumarate reductase.

Another aspect of the invention is a composition for treatment of *P. gingivalis* infection comprising as an active ingredient an inhibiting agent of a polypeptide that modulates biofilm formation or development.

In another aspect of the present invention, there is provided an interfering RNA molecule, the molecule comprising a double stranded region of at least 19 base pairs in each strand wherein one of the strands of the double stranded region is substantially complementary to a region of a polynucleotide encoding a polypeptide as described above. In one embodiment, one of the strands is complementary to a region of polynucleotide encoding a polypeptide of a sequence listed in Table 4.

In one embodiment, the inhibiting agent is an antagonist of the polypeptide. For *P. gingivalis*, the polypeptide may be fumarate reductase and the antagonist is selected from one or more of inhibiting agents of fumarate reductase. Additional suitable inhibiting agents include natural products, that include but are not limited to decursin, verticipyrone, paecilaminol, 5-alkenyl-3,3(2H)-furanones from *Streptomyces* spp., nafuredin, mesaconic acid, rotenone, and natural, semi-synthetic and synthetic analogues thereof. In another aspect, inhibiting agents of the current invention may be synthetic compounds that include but are not limited to; 2-substituted 4,6-dinitrophenols; mercaptopyridine N-oxide; L-092,201 (Merck Sharpe and Dohme); nitro-imidazoles such as fexindazole megazol benznidazole, MK-436, L-634,549, misonidazole; or benzimidazoles such as albendazole, cambendazole mebendazole, oxfendazole, parebendazole and thiabendazole; or oxantel or morantel. Preferred inhibiting agents are oxantel, morantel or thiabendazole. A particularly preferred inhibiting agent is oxantel.

It will be recognised by the skilled addressee that the selection of the inhibiting agent will be dependent upon number of clinical factors which determine whether the inhibiting agent is appropriate for use in a clinical setting.

DETAILED DESCRIPTION OF THE EMBODIMENTS

Figure 1:
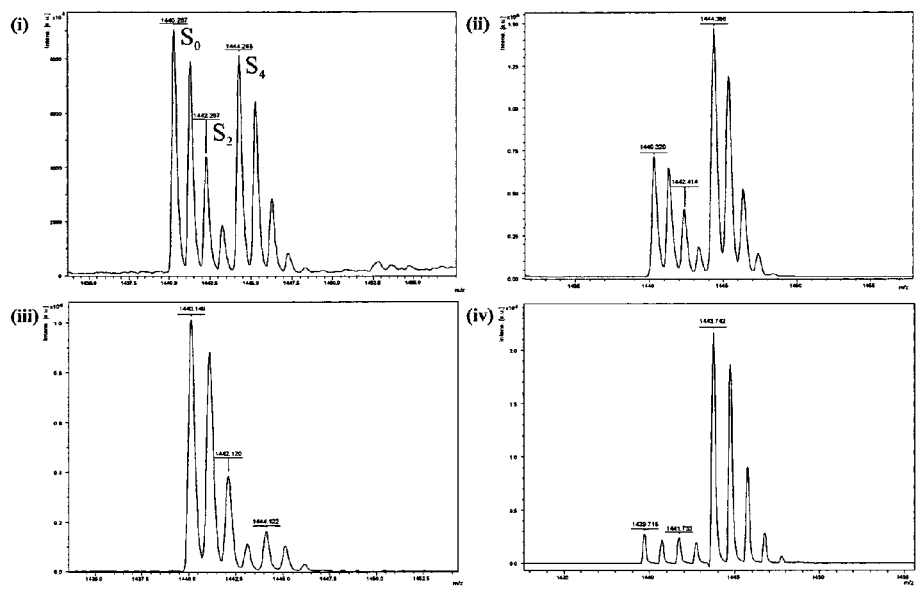
FIG. 1: $^{16}O/^{18}O$ quantification of specific BSA ratios. Quantification of known amounts of BSA was carried out in the same manner as for the biofilm and planktonic samples reported in the experimental procedures to validate the methodology. Briefly pre-determined amounts of BSA were loaded in adjacent lanes of a NuPAGE gel followed by excision of bands of equal size, normal or reverse proteolytic labelling, nanoHPLC and MALDI TOF-MS/MS. (A) MS spectra of BSA tryptic peptide, RHPEYAVSVLLR at known $^{16}O:^{18}O$ labelling ratios 1:1 (i), 2:1 (ii), 1:5 (iii) and 10:1 (iv) showing the characteristic doublet isotopic envelope for $^{16}O$ and $^{18}O$ labelled peptide (S0, S2 and S4 are the measured intensities of the isotopic peaks) (B) SDS PAGE gel of known BSA ratios used for the quantification procedure.
Figure 1:

Using a proteomic strategy the present inventors successfully identified and quantified the changes in abundance of 116 $P.$ $gingivalis$ cell envelope proteins between the biofilm and planktonic states, with the majority of proteins identified by multiple peptide hits. The present inventors demonstrated enhanced expression of a large group of cell-surface located C-Terminal Domain family proteins including RgpA, HagA, CPG70 and PG99. Other proteins that exhibited significant changes in abundance included transport related proteins (HmuY and IhtB), metabolic enzymes (FrdA and FrdB), immunogenic proteins and numerous proteins with as yet unknown functions.

Accordingly, the present invention provides an isolated $P.$ $gingivalis$ polypeptide, the polypeptide having an amino acid sequence selected from the group consisting of sequences corresponding to accession numbers listed in Table 4 and sequences at least 95% identical thereto.

Preferably, the isolated polypeptide is at least 96%, 97%, 98%, 99% or 100% identical to the amino acid sequence of any one of the sequences corresponding to the accession numbers listed in Table 4.

The terms "peptides, proteins, and polypeptides" are used interchangeably herein. The polypeptides of the present invention can include recombinant polypeptides such as fusion polypeptides. Methods for the production of a fusion polypeptide are well-known to those skilled in the art.

As will be well understood by those skilled in the art alterations may be made to the amino acid sequences corresponding to the accession numbers listed in Table 4. These alterations may be deletions, insertions, or substitutions of amino acid residues. The altered polypeptides can be either naturally occurring (that is to say, purified or isolated from a natural source) or synthetic (for example, by site-directed mutagenesis on the encoding DNA). It is intended that such altered polypeptides which have at least 85%, preferably at least 90%, 95%, 96%, 97%, 98% or 99% identity with the sequences corresponding to the accession numbers listed in Table 4 are within the scope of the present invention. Antibodies raised against these altered polypeptides will also bind to the polypeptides having one of the sequences corresponding to the accession numbers listed in Table 4.

Whilst the concept of conservative substitution is well understood by the person skilled in the art, for the sake of clarity conservative substitutions are those set out below.

Gly, Ala, Val, Ile, Leu, Met;
Asp, Glu, Ser;
Asn, Gln;
Ser, Thr;
Lys, Arg, H is;
Phe, Tyr, Trp, H is; and
Pro, Nα-alkalamino acids.

The practice of the invention will employ, unless otherwise indicated, conventional techniques of chemistry, molecular biology, microbiology, recombinant DNA, and immunology well known to those skilled in the art. Such techniques are described and explained throughout the literature in sources such as, J. Perbal, A Practical Guide to Molecular Cloning, John Wiley and Sons (1984), J. Sambrook et Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present). The disclosure of these texts are incorporated herein by reference.

An "isolated polypeptide" as used herein refers to a polypeptide that has been separated from other proteins, lipids, and nucleic acids with which it naturally occurs or the polypeptide or peptide may be synthetically synthesised. Preferably, the polypeptide is also separated from substances, for example, antibodies or gel matrix, for example, polyacrylamide, which are used to purify it. Preferably, the polypeptide constitutes at least 10%, 20%, 50%, 70%, and 80% of dry weight of the purified preparation. Preferably, the preparation contains a sufficient amount of polypeptide to allow for protein sequencing (ie at least 1, 10, or 100 mg).

The isolated polypeptides described herein may be purified by standard techniques, such as column chromatography (using various matrices which interact with the protein products, such as ion exchange matrices, hydrophobic matrices and the like), affinity chromatography utilizing antibodies specific for the protein or other ligands which bind to the protein.

A "contiguous amino acid sequence" as used herein refers to a continuous stretch of amino acids.

A "recombinant polypeptide" is a polypeptide produced by a process that involves the use of recombinant DNA technology.

In determining whether or not two amino acid sequences fall within a specified percentage limit, those skilled in the art will be aware that it is necessary to conduct a side-by-side comparison or multiple alignments of sequences. In such comparisons or alignments, differences will arise in the positioning of non-identical residues, depending upon the algorithm used to perform the alignment. In the present context, reference to a percentage identity or similarity between two or more amino acid sequences shall be taken to refer to the number of identical and similar residues respectively, between said sequences as determined using any standard algorithm known to those skilled in the art. For example, amino acid sequence identities or similarities may be calculated using the GAP programme and/or aligned using the PILEUP programme of the Computer Genetics Group, Inc., University Research Park, Madison, Wis., United States of America (Devereaux et al et al., 1984). The GAP programme utilizes the algorithm of Needleman and Wunsch (1970) to maximise the number of identical/similar residues and to minimise the number and length of sequence gaps in the alignment. Alternatively or in addition, wherein more than two amino acid sequences are being compared, the Clustal W programme of Thompson et al, (1994) is used.

One aspect of the invention is a method of preventing or treating a subject for periodontal disease comprising administering to the subject a pharmaceutical composition according to the present invention.

In one method a subject is treated including prophylactic treatment for periodontal disease. Periodontal diseases range from simple gum inflammation to serious disease that results in major damage to the soft tissue and bone that support the teeth. Periodontal disease includes gingivitis and periodontitis. Bacteria, such as *P. gingivalis* causes inflammation of the gums that is called "gingivitis." In gingivitis, the gums become red, swollen and can bleed easily. When gingivitis is not treated, it can advance to "periodontitis" (which means "inflammation around the tooth."). In periodontitis, gums pull away from the teeth and form "pockets" that are infected. The body's immune system fights the bacteria as the plaque spreads and grows below the gum line. If not treated, the bones, gums, and connective tissue that support the teeth are destroyed. The teeth may eventually become loose and have to be removed.

The present invention also provides a composition useful in the prevention or treatment of periodontal disease, the composition comprising an antagonist of a *P. gingivalis* polypeptide of the first aspect of the present invention and a pharmaceutically acceptable carrier, wherein the antagonist inhibits *P. gingivalis* infection.

An oral composition of this invention which contains the above-mentioned pharmaceutical composition may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. An oral composition according to this invention may further include additional well known ingredients depending on the type and form of a particular oral composition.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 5 to about 9 and typically from about 5.0 to 7.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In other desirable forms of this invention, the pharmaceutical composition may be substantially solid or pasty in character, such as toothpowder, a dental tablet or a toothpaste (dental cream) or gel dentifrice. The vehicle of such solid or pasty oral preparations generally contains dentally acceptable polishing material.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% $MgO$, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a bottle of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

In a further aspect, the present invention provides a kit of parts including (a) a composition of polypeptide inhibitory agent and (b) a pharmaceutically acceptable carrier. Desirably, the kit further includes instructions for their use for inhibiting biofilm formation in a patent in need of such treatment.

Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Comparisons of *P. gingivalis* protein abundances between growth as a biofilm and the planktonic state revealed many changes to the proteome of this pathogenic bacterium, in particular the lower abundance of the fumarate reductase enzymes essential for glutamate/aspartate catabolism. In a separate study involving comparing the proteome changes of haem-limited and excess *P. gingivalis*, there was an observable shift in fermentation patterns during haem-limitation which lead to increased acetate production and was consistent with the co-ordinated changes in abundance of enzymes in the major catabolic pathway of *P. gingivalis*. Of particular interest was the consistent lower abundance of the fumarate reductase enzymes during haem-limitation and biofilm growth. The present inventors subsequently demonstrated the utility of three Frd inhibiting agents (oxantel, morantel and thiabendazole) against *P. gingivalis* survival and sub minimal inhibitory concentrations (subMIC) to disrupt normal development of the biofilm.

As used herein, the term "antagonist" refers to a nucleic acid, peptide, antibody, ligands or other chemical entity which inhibits the biological activity of the polypeptide of interest. A person skilled in the art would be familiar with techniques of testing and selecting suitable antagonists of a specific protein, such techniques would include binding assays.

The antibodies and antagonists of the present invention have a number of applications, for example, they can be used as antimicrobial preservatives, in oral care products (toothpastes and mouth rinses) for the control of dental plaque and suppression of pathogens associated with dental caries and periodontal diseases. The antibodies and antagonists of the present invention may also be used in pharmaceutical preparations (eg, topical and systemic anti-infective medicines).

The present invention also provides interfering RNA molecules which are targeted against the mRNA molecules encoding the polypeptides of the first aspect of the present invention. Accordingly, in a seventh aspect of the present invention there is provided an interfering RNA molecule, the molecule comprising a double stranded region of at least 19 base pairs in each strand wherein one of the strands of the double stranded region is complementary to or capable of hybridizing under normal intracellular conditions with a region of an mRNA molecule encoding a polypeptide of the first aspect of the invention.

So called RNA interference or RNAi is known and further information regarding RNAi is provided in Hannon (2002) *Nature* 418: 244-251, and McManus & Sharp (2002) *Nature Reviews: Genetics* 3(10): 737-747, the disclosures of which are incorporated herein by reference.

The present invention also contemplates chemical modification(s) of siRNAs that enhance siRNA stability and support their use in vivo (see for example, Shen et al. (2006) *Gene Therapy* 13: 225-234). These modifications might include inverted abasic moieties at the 5' and 3' end of the sense strand oligonucleotide, and a single phosphorthioate linkage between the last two nucleotides at the 3' end of the antisense strand.

It is preferred that the double stranded region of the interfering RNA comprises at least 20, preferably at least 25, and most preferably at least 30 base pairs in each strand of the double stranded region. The present invention also provides a method of treating a subject for periodontal disease comprising administering to the subject at least one of the interfering RNA molecules of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. The invention specifically includes all combinations of features described in this specification.

In order that the nature of the present invention may be more clearly understood, preferred aspects of the invention will now be described in more detail with reference to the following tables and examples of compositions.

Growth and Harvesting of *P. gingivalis* for Biofilm v Planktonic Studies

*Porphyromonas gingivalis* W50 (ATCC 53978) was grown in continuous culture using a model C-30 BioFlo chemostat (New Brunswick Scientific) with a working volume of 400 mL. Both the culture vessel and medium reservoir were continuously gassed with 10% $CO_2$ and 90% $N_2$. The growth temperature was 37° C. and the brain heart infusion growth medium (Oxoid) was maintained at pH 7.5. Throughout the entire growth, redox potential maintained at −300 mV. The dilution rate was 0.1 $h^{-1}$, giving a mean generation time (MGT) of 6.9 h. Sterile cysteine-HCl (0.5 g/L) and hemin (5 mg/L) were added. The culture reached steady state approximately 10 days after inoculation and was maintained for a further 30 days until a thick layer of biofilm had developed on the vertical surfaces of the vessel.

All bacterial cell manipulations were carried out on ice or at 4° C. During harvesting, the planktonic cells were decanted into a clean container and the biofilm washed twice gently with PGA buffer (10.0 mM $NaH_2PO_4$, 10.0 mM KCl, 2.0 mM, citric acid, 1.25 mM $MgCl_2$, 20.0 mM $CaCl_2$, 25.0 mM $ZnCl_2$, 50.0 mM $MnCl_2$, 5.0 mM $CuCl_2$, 10.0 mM $CoCl_2$, 5.0 mM $H_3BO_3$, 0.1 mM $Na_2Moa_4$, 10 mM cysteine-HCl with the pH adjusted to 7.5 with 5 M NaOH at 37° C.) followed by harvesting of the biofilm into a 50 mL centrifuge tube.

Planktonic and biofilm cells were then washed 3 times (7000 g) with PGA buffer and both samples resuspended to a final volume of 30 mL with wash buffer (50 mM Tris-HCl, 150 mM NaCl, 5 mM $MgCl_2$, pH 8.0, proteinase inhibitor (Sigma)) and lysed by 3 passages through a French Press Pressure Cell (SLM, AMINCO) at 138 MPa. The lysed cells were centrifuged at 2000 g for 30 min to remove any unbroken cells. The supernatant was further centrifuged at 100000 g for 1 h to separate the lysed cells into their soluble and insoluble (cell envelope) fractions. The cell envelope fraction was further washed 3 times with wash buffer at 100000 g, for 20 min each to remove any soluble contaminations. All samples were then frozen and stored at 80° C.

Growth and Harvesting of *P. gingivalis* for Haem-Limitation and Excess Studies

*P. gingivalis* W50 was grown in continuous culture using a Bioflo 110 fermenter/bioreactor (New Brunswick Scientific) with a 400 mL working volume. The growth medium was 37 g/L brain heart infusion medium (Oxoid) supplemented with 5 mg/mL filter sterilized cysteine hydrochloride, 5.0 µg/mL haemin (haem-excess) or 0.1 µg/mL haemin (haem-limited). Growth was initiated by inoculating the culture vessel with a 24 h batch culture (100 mL) of *P. gingivalis* grown in the same medium (haem-excess). After 24 h of batch culture growth, the medium reservoir pump was turned on and the medium flow adjusted to give a dilution rate of 0.1 $h^{-1}$ (mean generation time (MGT) of 6.9 h). The temperature of the vessel was maintained at 37° C. and the pH at 7.4±0.1. The culture was continuously gassed with 5% $CO_2$ in 95% $N_2$. Cells were harvested during steady state growth, washed three times with wash buffer (50 mM Tris-HCl pH 8.0, 150 mM NaCl, 5 mM $MgCl_2$) at 5000 g for 30 min and disrupted with 3 passes through a French Pressure Cell (SLM, AMINCO) at 138 MPa. The lysed cells were then centrifuged at 2000 g for 30 min to remove unbroken cells followed by ultracentrifugation at 100000 g, producing a soluble (supernatant) and membrane fraction. All fractions were carried out on ice.

Preparation and Analysis of $^{18}O$ Proteolytic Labelled Biofilm and Planktonic Cell Envelope Fraction The cell envelope fraction was first resuspended in 1 mL of ice cold wash buffer containing 2% SDS, then sonication and vortexing were carried out to aid resuspension of the pellet. The final step in resuspension involved use of a 29-gauge-insulin needle to help break up particulates. The mixture was then centrifuged at 40000 g to remove insoluble particles and the protein concentration of the supernatant was determined using the BCA reagent (Pierce) according to the manufacturer's instructions.

The resuspended samples were subjected to precipitation using 5 volumes of ice cold acetone overnight at −20° C. which further helped to inactivate any proteolytic activity. After acetone precipitation, both samples were resuspended to a final concentration of 3 mg/mL with 25 mM Tris pH 8.0 and 1% SDS assisted by intermittent sonication, vortexing and the use of a 29-gauge-insulin needle. A second BCA protein assay was then carried out to standardize the final protein amount.

Gel electrophoresis on a NuPAGE gel was carried out as per manufacturer's protocol using MOPs running buffer (NuPAGE, Invitrogen) except the samples were boiled at 99° C. for 5 min prior to loading onto a 10-well 10% NuPAGE gel with MOPs as the running buffer. The biofilm and planktonic samples (30 µg each) were loaded in adjacent lanes on the gel. SDS-PAGE was then carried out at 126 V (constant) at 4° C. until the dye front was approximately 1 cm from the bottom of the gel. For the biological replicate, the gel used was a 4-12% NUPAGE gradient gel using MOPs as the running buffer to give a similar but not exact pattern of separation so as to overcome the potential variation of a protein band being separated into two fractions. Staining was carried out overnight in Coomassie brilliant blue G-250 (31) followed by overnight destaining in ultrapure $H_2O$.

The two gel lanes were divided into 10 gel bands of equal sizes using a custom made stencil and each section cut into approximately 1 $mm^3$ cubes. Destaining was carried out 3 times in a solution of 50 mM $NH_4HCO_3$/ACN (1:1). After destaining, the gel cubes were dehydrated with 100% ACN, followed by rehydration/reduction with a solution of 10 mM dithiothreitol in ABC buffer (50 mM $NH_4HCO_3$) at 56° C. for 30 min. The excess solution was removed before adding 55 mM iodoacetamide in ABC buffer for 60 min at room temperature in the dark. After the alkylation reaction, the gel cubes were washed 3 times in ABC buffer, followed by dehydration twice in 100% ACN for 10 min. The gel cubes were further dried under centrifugation using a speedvac for 90 min. Digestion was carried out in 60 µL solution per gel section containing 2 µg of sequence grade modified trypsin (Promega) and ½ strength ABC buffer made up in either $H_2^{16}O$ or $H_2^{18}O$ ($H_2^{18}O$, >97% purity, Marshall Isotopes) for 20 h at 37° C. After digestion, the peptides were twice extracted from the gel using a solution of 50% ACN/0.1% TFA in their respective water ($H_2^{16}O/H_2^{18}O$) and 0.1% TFA with the aid of sonication for 5 min each. The pooled extract was boiled at 99° C. for 5 min to inactivate the trypsin followed by freeze drying for 48 h.

The freeze-dried peptides were resuspended in a solution of 5% ACN/0.1% TFA in their respective water ($H_2^{16}O/H_2^{18}O$) just before analysis using nanoHPLC and MALDI TOF-MS/MS analysis. The peptide solution (20 µL) was then loaded onto an Ultimate Nano LC system (LC Packings) using a FAMOS autosampler (LC Packings) in advanced µL pickup mode. The samples were first loaded onto a trapping column (300 µm internal diameter×5 mm) at 200 µL/min for 5 min. Separation was achieved using a reverse phase column (LC Packings, C18 PepMap100, 75 µm i.d.×15 cm, 3 µm, 100 Å) with a flow rate of 300 mL/min, and eluted in 0.1% formic acid with an ACN gradient of 0-5 min (0%), 5-10 min (0-16%), 10-90 min (16-80%), 90-100 min (80-0%).

Eluents were spotted straight onto pre-spotted anchorchip plates (Bruker Daltonics) using the Proteineer Fc robot (Bruker Daltonics) at 30 s intervals. Prior to spotting, each spot position was pre-spotted with 0.2 µL of ultrapure $H_2O$ to reduce the concentration of the acetonitrile during the crystallization process with the matrix.

The plate was washed with 10 mM ammonium phosphate and 0.1% TFA and air-dried before automated analysis using a MALDI-TOF/TOF (Ultraflex with LIFT II upgrade, Bruker Daltonics). MS analysis of the digest was initially carried out in reflectron mode measuring from 800 to 3500 Da using an accelerating voltage of 25 kV. All MS spectra were produced from 8 sets of 30 laser shots, with each set needing to have a signal to noise, S/N>6, Resolution >3000 to be included. Calibration of the instrument was performed externally with [M+H]$^+$ ions of the prespotted internal standards (Angiotensin II, Angiotensin I, Neurotensin, Renin_substrate and ACTH_Clip) for each group of four samples. LIFT mode for MALDI-TOF/TOF was carried out in a fully automated mode using the Flexcontrol and WarpLC software (Bruker Daltonics). In the TOF1 stage, all ions were accelerated to 8 kV and subsequently lifted to 19 kV in the LIFT cell and all MS/MS spectra were produced from accumulating 550 consecutive laser shots.

Selection of parent precursors was carried out using the WarpLC software (ver 1.0) with the LC MALDI SILE (Stable Isotope Labelling Experiment) work flow. Only the most abundant peak of each heavy or light pair separated by 4 Da was selected, providing its S/N was >50. Compounds separated by less than six LC MALDI fractions were considered the same and therefore selected only once.

Peak lists were generated using Flexanalysis 2.4 Build 11 (Bruker Daltonics) with the Apex peak finder algorithm with S/N>6. The MS scan was smoothed once with the Savitzky Golay algorithm using a width of 0.2 m/z and baseline subtraction was achieved using the Median algorithm with flatness of 0.8.

Protein identification was achieved using the MASCOT search engine (MASCOT version 2.1.02, Matrix Science) on MS/MS data queried against the *P. gingivalis* database obtained from The Institute for Genomic Research (TIGR) website (www.tigr.org). MASCOT search parameters were: charge state 1+, trypsin as protease, one missed cleavage allowed and a tolerance of 250 ppm for MS and 0.8 m/z for MS/MS peaks. Fixed modification was set for carbamidomethyl of cysteine and variable modification was C-terminal $^{18}$O labelled lysine and arginine residues.

A reverse database strategy as described previously (32) was employed to determine the minimum peptide MASCOT score required to omit false positives for single peptide identification. Briefly, the database consists of both the sequence of every predicted *P. gingivalis* protein in its normal orientation and the same proteins with their sequence reversed (3880 sequences). The whole MS/MS dataset was then searched against the combined database to determine the lowest Mascot score to give 0% false positives. A false positive was defined as a positive match to the reversed sequence (bold red and above peptide threshold score). A false positive rate for single hit peptides was determined to be 0.5% with Mascot peptide ion scores of >threshold and <25. When the Mascot peptide ion score was >30, there was no match to the reverse database. In order to increase the confidence of identification for single hits peptide, we used a minimum Mascot peptide ion score of >50 which gives a two order of magnitude lower probability of incorrect identification than if a score of 30 was used, according to the Mascot scoring algorithm.

The matched peptides were evaluated using the following criteria, i) at least 2 unique peptides with a probability based score corresponding to a p-value <0.05 were regarded as positively identified (required bold red matches) where the score is $-\log \times 10 \log(P)$ and P is the probability that the observed match is a random event (33), ii) where only one unique peptide was used in the identification of a specific protein (identification of either heavy or light labelled peptide is considered as one) the MASCOT peptide ion score must be above 50 or that peptide is identified in more than one of the four independent experiments (2 biological replicates and 2 technical replicates).

Due to the mixed incorporation of one or two $^{18}$O atoms into the peptides, the contribution of the natural abundance of the $^{18}$O isotope and the H$_2$$^{18}$O purity (a=0.97), the ratios of the peptides R were mathematically corrected using equation:

$$R=(I_1+I_2)/I_0 \quad (1)$$

$I_0$, $I_1$ and $I_2$ were calculated according to the following equations (27), $$I_1 = \frac{aS_2 - [aJ_2 - 2(1-a)J_4]S_0 - 2(1-a)S_4}{a^2 - (2-a-a^2)J_2 + 2(1-a)^2 J_4} \quad (2)$$

$$I_0 = S_0 - (1-a)I_1 \quad (3)$$

$$I_2 = \frac{1}{a^2}(S_4 - J_4 I_0 - J_2 I_1) \quad (4)$$

Where $S_0$, $S_2$ and $S_4$ are the measured intensities of the monoisotopic peak for peptide without $^{18}$O label, the peak with 2 Da higher than the monoisotopic peak, and the peak with 4 Da higher than the monoisotopic peak respectively (FIG. 1A). $J_0$, $J_2$ and $J_4$ are the corresponding theoretical relative intensities of the isotopic envelope of the peptide calculated from MS-Isotope (http://prospector.ucsf.edu). However when the intensity of the second isotopic peaks ($S_1$ and $S_5$) was more intense than the first isotopic peaks ($S_0$ and $S_4$), the ratio was simply calculated as $S_1$ divided by $S_5$. This was true especially for large peptides above 2000 m/z where the contribution of the fifth isotopic peak of the $^{16}$O labelled peptide to the $S_4$ peak becomes significant. Calculation of mixed $^{16}$O$^{18}$O incorporation was determined by the difference in the experimental $S_2$ and theoretical $S_2$ ($J_2$) as a percentage of experimental $S_4$.

Protein abundance ratios were determined by averaging all identified peptides of the same protein, even when the same protein was identified in more than one gel section. The data from each "normal" replicate was combined with the inversed ratios from its respective "reverse" replicate providing an average ratio and standard error for each protein in each biological replicate. Normalization of both the biological replicates was then carried out similarly to that previously reported (34,35). Briefly the averaged ratio for each biological replicate was multiplied by a factor so that the geometric mean of the ratios was equal to one.

Preparation and Analysis of ICAT Labelled Haem-Limited and Excess Cells

Protein labelling and separation were based on the geLC-MS/MS approach (Li et al., 2003) using the cleavable ICAT reagent (Applied Biosystems). Another proteomic approach has been taken in PCT/AU2007/000890 which is herein incorporated by reference. Protein was first precipitated using TCA (16%) and solubilised with 6 M urea, 5 mM EDTA, 0.05% SDS and 50 mM Tris-HCl pH 8.3. Protein concentration was determined using the BCA protein reagent and adjusted to 1 mg/ml. 100 μg of protein from each growth condition was individually reduced using 2 μL of 50 mM Tris(2-carboxy-ethyl)phosphine hydrochloride for 1 h at 37° C. Reduced protein from the haem-limitation growth condition was then alkylated with the ICAT$_{heavy}$ reagent and protein from haem-excess growth condition with the ICAT$_{light}$ reagent. The two samples were then combined and subjected to SDS-PAGE on a precast Novex 10% NUPAGE gel (Invitrogen). The gel was stained for 5 min using SimplyBlue™ SafeStain (Invitrogen) followed by destaining with water. The gel lane was then excised into 20 sections from the top of the gel to the dye front.

The excised sections were further diced into 1 mm³ cubes and in-gel digested overnight and extracted twice according to the above procedure. The pooled supernatant was dried under reduced vacuum to about 50 µL followed by mixing with 500 µL of affinity load buffer before loading onto the affinity column as per manufacturer's instruction (Applied Biosystems). Eluted peptides were dried and the biotin tag cleaved with neat TFA at 37° C. for 2 h followed by drying under reduced vacuum. The dried samples were suspended in 35 µL of 5% acetonitrile in 0.1% TFA.

MS was carried out using an Esquire HCT ion trap mass spectrometer (Bruker Daltonics) coupled to an UltiMate Nano LC system (LC Packings—Dionex). Separation was achieved using a LC Packings reversed phase column (C18 PepMap100, 75 µm i.d.×15 cm, 3 µm, 100 Å), and eluted in 0.1% formic acid with the following acetonitrile gradient: 0-5 min (0%), 5-10 min (0-10%), 10-100 min (10-50%), 100-120 min (50-80%), 120-130 min (80-100%).

The LC output was directly interfaced to the nanospray ion source. MS acquisitions were performed under an ion charge control of 100000 in the m/z range of 300-1500 with maximum accumulation time of 100 ms. When using GPF three additional m/z ranges (300-800, 700-1200 and 1100-1500) were used to select for precursor ions and each m/z range was carried out in duplicate to increase the number of peptides identified. MS/MS acquisition was obtained over a mass range from 100-3000 m/z and was performed on up to 10 precursors for initial complete proteome analysis and 3 for ICAT analysis for the most intense multiply charged ions with an active exclusion time of 2 min.

Peak lists were generated using DataAnalysis 3.2 (Bruker Daltonics) using the Apex peak finder algorithm with a compound detection threshold of 10000 and signal to noise threshold of 5. A global charge limitation of +2 and +3 were set for exported data. Protein identification was achieved using the MASCOT search engine (MASCOT 2.1.02, Matrix Science) on MS/MS data queried against the *P. gingivalis* database obtained from The Institute for Genomic Research (TIGR) website (www.tigr.org). The matched peptides were further evaluated using the following criteria, i) peptides with a probability based Mowse score corresponding to a p-value of at most 0.05 were regarded as positively identified, where the score is $-\log \times 10(\log(P))$ and P is the probability that the observed match is a random event ii) where only one peptide was used in the identification of a specific protein and the MASCOT score was below 30, manual verification of the spectra was performed. To increase confidence in the identification of ICAT-labelled proteins especially for those with single peptide hits, additional filters were applied as follows: i) the heavy and light peptides of an ICAT pair must have exhibited closely eluting peaks as determined from their extracted ion chromatograms ii) for proteins with a single unique peptide, this peptide must have been identified more than once (e.g. in different SDS-PAGE fractions or in both the light and heavy ICAT forms iii) if a single peptide did not meet the criteria of (ii), the MASCOT score must have been $\geq 25$, the expectation value $\leq 0.01$ and the MS/MS spectrum must have exhibited a contiguous series of 'b' or 'y'-type ions with the intense ions being accounted. Determinations of false positives were as described above.

The ratio of isotopically heavy $^{13}C$ to light $^{12}C$ ICAT labelled peptides was determined using a script from DataAnalysis (Bruker Daltonics) and verified manually based on measurement of the monoisotopic peak intensity (signal intensity and peak area) in a single MS spectrum. The minimum ion count of parent ions used for quantification was 2000 although >96% of both heavy and light precursor ions were >10000. In the case of poorly resolved spectra, the ratio was determined from the area of the reconstructed extracted ion chromatograms (EIC) of the parent ions. Averages were calculated for multiple peptides derived from a single parent protein and outliers were removed using the Grubb's test with $\alpha=0.05$.

The cellular localization of *P. gingivalis* proteins was predicted using CELLO (http://cello.life.nctu.edu.tw (36)). Extracellular, outer membrane, inner membrane and periplasmic predictions were considered to be from the envelope fraction.

The concentrations of short-chain fatty acids (SCFA) in cell-free culture supernatants (uninoculated, haem-excess and haem-limited) were determined by capillary gas chromatography based on the derivatization method of Richardson et al. (37).

The correlation coefficient (r) between both biological replicates was evaluated using the Pearson correlation coefficient function from Microsoft Excel. The coefficient of variance (CV) was calculated by the standard deviation of the peptide abundance ratios divided by the mean, expressed as a percentage.

Extraction of Nucleic Acids for Transcriptomic Analysis

RNA was extracted from 5 mL samples of *P. gingivalis* cells harvested directly from the chemostat. To each sample 0.2 volumes of RNA Stabilisation Reagent (5% v/v phenol in absolute ethanol) were added. Cells were pelleted by centrifugation (9000 g, 5 min, 25° C.), immediately frozen in liquid nitrogen and stored at −70° C. for later processing. Frozen cells were suspended in 1 mL of TRIzol reagent (Invitrogen) per $1 \times 10^{10}$ cells and then disrupted using Lysing Matrix B glass beads (MP Biomedicals) and the Precellys 24 homogeniser (Bertin Technologies, France). The glass beads were removed by centrifugation and the RNA fraction purified according to the TRIzol manufacturer's (Invitrogen) protocol, except that ethanol (at a final concentration of 35%) rather than isopropanol was added at the RNA precipitation stage and samples were then transferred to the spin-columns from the Illustra RNAspin Mini RNA Isolation kit (GE Healthcare). RNA was purified according to the manufacturer's instructions from the binding step onwards, including on-column DNAse treatment to remove any residual DNA. RNA integrity was determined using the Experion automated electrophoresis station (Bio-Rad).

Genomic DNA was extracted from *P. gingivalis* cells growing in continuous culture using the DNeasy Blood & Tissue Kit (Qiagen) in accordance with the manufacturer's instructions.

Microarray Design, Hybridization and Analysis

Microarray slides were printed by the Australian Genome Research Facility and consisted of 1977 custom designed 60-mer oligonucleotide probes for the predicted protein coding regions of the *P. gingivalis* W83 genome including additional protein coding regions predicted by the Los Alamos National Laboratory Oralgen project. Microarray Sample Pool (MSP) control probes were included to aid intensity-dependent normalisation. The full complement of probes was printed 3 times per microarray slide onto Corning UltraGAPS coated slides.

Slides were hybridised using either heme-excess or heme-limited samples labelled with Cy3, combined with a universal genomic DNA reference labelled with Cy5 (GE Lifesciences). cDNA was synthesized from 10 µg of total RNA using the SuperScript plus indirect cDNA labelling system (Invitrogen), with 5 µg of random hexamers (Invitrogen) for priming of the cDNA synthesis reaction. cDNA was labelled with Cy3 using the Amersham CyDye post-labelling reactive dye pack (GE Lifesciences) and purified using the purification module of the Invitrogen labelling system. Cy5-dUTP labelled genomic cDNA was synthesized in a similar manner from 400 ng of DNA, using the BioPrime Plus Array CGH Indirect Genomic Labelling System (Invitrogen).

Prior to hybridisation, microarray slides were immersed for 1 h in blocking solution (35% formamide, 1% BSA, 0.1% SDS, 5×SSPE [1×SSPE is 150 mM NaCl, 10 mM $NaH_2PO_4$, 1 mM EDTA]) at 42° C. After blocking slides were briefly washed in $H_2O$ followed by 99% ethanol and then dried by centrifugation. Labelled cDNAs were resuspended in 55 μL of hybridization buffer (35% formamide, 5×SSPE, 0.1% SDS, 0.1 mg $mL^{-1}$ Salmon Sperm DNA) denatured at 95° C. for 5 min then applied to slides and covered with LifterSlips (Erie Scientific). Hybridisation was performed at 42° C. for 16 h. Following hybridisation slides were successively washed in 0.1% SDS plus 2×SSC [1×SSC is 150 mM NaCl 15 mM sodium citrate] (5 min at 42° C., all further washes performed at room temperature), 0.1% SDS plus 0.1×SSC (10 min), 0.1×SSC (4 washes, 1 min each), and then quickly immersing in 0.01×SSC, then 99% ethanol and using centrifugation to dry the slides.

Slides were scanned using a GenePix 4000B microarray scanner and images analysed using GenePix Pro 6.0 software (Molecular Devices). Three slides were used for each treatment (heme-limitation or heme-excess) representing three biological replicates.

Image analysis was performed using the GenePix Pro 6.0 software (Molecular Devices), and "morph" background values were used as the background estimates in further analysis. To identify differentially expressed genes the LIMMA software package was used with a cut off of P<0.005. Within array normalisation was performed by fitting a global loess curve through the MSP control spots and applying the curve to all other spots. The Benjamini Hochberg method was used to control the false discovery rate to correct for multiple testing.

Gene predictions were based on the P. gingvalis W83 genome annotation from the The Institute for Genomic Research (TIGR, www.tigr.org). Operon prediction was carried out from the Microbesonline website (http://microbesonline.org)

Response of P. gingivalis to Heme-Limitation as Determined Using DNA Microarray Analysis A DNA microarray analysis of the effect of heme-limited growth on P. gingivalis global gene expression was carried out under identical growth conditions employed for the proteomic analysis. Analysis of data from three biological replicates identified a total of 160 genes that showed statistically significant differential regulation between heme-excess and heme-limitation, with the majority of these genes showing increased levels of expression under conditions of heme-limitation and only 8 genes being down-regulated. Many of the up-regulated genes were predicted to be in operons and the majority of these showed similar changes in transcript levels (Table 3 and 5). There was broad agreement between the transcriptomic and proteomic data with a significant correlation between the two data sets where differential regulation upon heme-limitation was observed [Spearman's correlation 0.6364, p<0.05]. However for some of the proteins showing differences in abundance from the proteomic analysis, the transcriptomic analysis of the corresponding genes did not detect any statistically significant differences in the abundance of the mRNA. The microarray analyses tended to identify only those genes encoding proteins that had large changes in abundance as determined by the proteomic analysis (Tables 3 and 5). Where protein and transcript from the same gene were found to be significantly regulated by heme-limitation the majority showed the same direction of regulation. The exceptions were two gene products, PG0026 a CTD family putative cell surface proteinase and PG2132 a fimbrillin (FimA). These proteins decreased in abundance in the proteomic analysis under heme-limitation but were predicted to be up-regulated by the transcriptomic analysis. Both these proteins are cell surface located and it is quite possible that they are either released from the cell surface or post-translationally modified which could preclude them from being identified as up-regulated in the proteomic analysis.

Susceptibility of P. gingivalis to Frd Inhibiting Agents

The effect of Frd inhibiting agents on P. gingivalis was carried out in liquid cultures. Briefly W50 was cultured in 200 mL BHI medium until OD of 0.6 (~2.9×$10^8$ cfu/mL). The cells were then resuspended in fresh growth medium to a final concentration of 2.5×$10^7$ cfu/mL. Oxantel pamonate, morantel citrate and thiabendazole (Sigma) were dissolved in DMSO to achieve stock concentrations of 250 mM. 4 μL of the test solution was then mixed with 196 μL of cell suspension and transferred into 96 well flat bottom plates followed by incubation at 37° C. under anaerobic conditions and monitored hourly over a 50 h period by measuring the optical density of the culture at 620 nm using an iEMS microplate reader (Labsystems OY Research Technologies Division). Mean generation times of P. gingivalis in the presence of different inhibiting agents were calculated by dividing the doubling time $[(Log_{10} N_t–Log_{10} N_0)/Log_{10} 2]$ by the time $(N_t–N_0)$ where $N_t$ and $N_0$ are cells population at time t and time zero, respectively.

Effects of Frd Inhibiting Agents on P. gingivalis Biofilm

P. gingivalis biofilm formation over 48 h in a static 96 well model was determined as described previously. Briefly P. gingivalis ATCC 33277 cells were resuspended to a final cell density of 2.5×$10^7$ before mixing with the test substances followed by transferring into 96 well flat bottom plates and incubated anaerobically at 37° C. Assessment of the biofilm mass was carried out at 24 h and 48 h by washing the cells twice with 250 μL of ultra pure water to remove loosely adhered cells followed by drying at 37° C. for 3 h. The dried biofilm was then stained in a solution of 0.1% crystal violet for 15 min and washed 2 times with 250 μL ultra pure water. The crystal violet stain was then dissolved from the biofilm using a solution of 80% ethanol and 20% acetone for 2 min through repeated pipetting before transferring to a new 96 well plate for measurement of the optical density at 620 nm.

Flowcell Biofilm Culture and CSLM Analysis

The biofilm culture of P. gingivalis ATCC 33277 in flow cells was similar to that previously described with several modifications. A 3-channel flow cell system (Stovall Life Science, USA) was set up in an anaerobic chamber (MK3 Anaerobic workstation; Don Whitley Scientific Ltd.) and was modified with silicon pump tubing (Gilson, France) and stopcocks for inoculation, testing and staining of the bacterial biofilms. All parts were assembled and 0.5% sodium hypochlorite was pumped into the system and left overnight to sterilise the system. Sterile water (200 mL) was then used to flush the system before growth medium addition. The system was inoculated with 1 mL of an exponentially growing P. gingivalis diluted to 0.1 $OD_{600}$. The system was incubated for 1 h prior to constant flow (0.2 mL/min) of 5× diluted BHI (Oxoid) supplemented with 0.1 g/L cysteine, 1 mg/L heamin and 1 mg/L vitamin K. After 18 h, 1 mL of 125 μM or 12.5 μM of Oxantel or sterile water was injected into each channel of the system and incubated for 30 min. The flow of medium was resumed for another 10 min to wash off any unbound cells due to testing. BacLight stain (Molecular Probes) was then used to stain the biofilm in situ (see below).

Confocal laser scanning microscopy (CLSM) of the bacterial biofilms was carried out on a Meta 510 Confocal Microscope with an inverted stage (Zeiss). Horizontal (xy) opto-digital sections, each 2 µm thick over the entire thickness of the biofilm (z) were imaged using a 63× objective at 512×512 pixel (0.28 µm per pixel), with each frame at 143.86 µm (x)×143.86 µm (y). To determine reproducibility across the biofilm 5 images at random positions from each of two biological replicates were obtained at wavelengths of 488 nm and 568 nm for each channel. All images obtained were analysed using COMSTAT software. Microcolonies were defined as cluster of cells with >500 pixel counts.

Viability of Cells Dispersed by Oxantel Treatment

To test the viability of cells dispersed by Oxantel treatment, a static biofilm assay was performed as described above but with slight modifications. Briefly *P. gingivalis* (ATCC 33277) was allowed to form biofilm in 24 well microplates after 18 h incubation. The free floating planktonic cells were first removed and the biofilm washed once with PBS. 1 mL of 125 uM or 12.5 uM of Oxantel or sterile water (positive control) was added to each well and incubated for 30 min. The number of dispersed *P. gingivalis* cells that are still viable was determined by cultural analysis on horse blood agar plates after serial dilution in BHI.

Statistical Analysis

The correlation coefficient (r) between both biological replicates was evaluated using the Pearson correlation coefficient function from Microsoft Excel. The coefficient of variance (CV) was calculated by the standard deviation of the peptide abundance ratios divided by the mean, expressed as a percentage.

Continuous Culture and Biofilm Formation

*P. gingivalis* W50 was cultured in continuous culture over a 40 day period during which the cell density of the culture remained constant after the first 10 days with an $OD_{650}$ of 2.69±0.21 and 2.80±0.52 for biological replicates 1 and 2 respectively. This equates to a cell density of ~3 mg cellular dry weight/mL. Over this time period a biofilm of *P. gingivalis* cells developed on the vertical glass wall of the fermenter vessel. This biofilm was ~2 mm thick at the time of harvest.

Validation of $^{16}O/^{18}O$ Quantification Method Using BSA

To determine the accuracy and reproducibility of the $^{16}O/^{18}O$ quantification method, known amounts of BSA were loaded onto adjacent gel lanes to give ratios of 1:1, 1:2, 1:5 and 10:1 (FIG. 1B). The bands were subjected to in-gel tryptic digestion in the presence of either $H_2^{16}O$ or $H_2^{18}O$, mixed and then analyzed by LC MALDI-MS/MS. A typical set of spectra for a single BSA tryptic peptide across the four ratios shows the preferential incorporation of two $^{18}O$ atoms, which is seen most clearly by the predominance of the +4 Da peak in the 10:1 BSA ratio, and by the almost symmetrical doublet in the 1:1 spectrum, simplifying both quantification and identification (FIG. 1A). The average incorporation of a single $^{18}O$ atom was estimated to be <7% based on the 1:1 labelling (Supplementary Table). The calculated average ratios for all identified BSA peptides were 0.98±0.12, 2.22±0.26, 4.90±0.75 and 10.74±2.04 for ratios of 1:1 (triplicate), 2:1 (and 1:2), 1:5 and 10:1, respectively indicating a good dynamic range, high accuracy of ±2-11% and a low CV ranging from 11.75% to 18.95% (Table 1). The reproducible accuracy of the 1:1 mixture (performed in triplicate) implies that labelling bias was very low. This was further confirmed by comparing normal and reverse labelled BSA at a 2:1 ratio, using only peptides that were identified in both experiments. The normal ratio was determined to be 2.11±0.33 while the reverse was 2.30±0.20 (Table 1).

Experimental Design for Quantitative Analysis of Biofilm and Planktonic Samples

The design of this study involved the use of two biological replicates, that is two independent continuous cultures, each one split into a biofilm sample obtained from the walls of the vessel, and a planktonic sample obtained from the fluid contents of the vessel. Two technical replicates for each biological replicate were performed, and although we had established that there was no significant labelling bias with BSA, we chose to utilize the reverse labelling strategy as there is a lack of $^{16}O/^{18}O$ labelling validation studies that have been conducted on complex biological samples (30). Therefore in total there were four experiments, each consisting of 10 LC-MALDI MS/MS runs stemming from 2×10 gel segments.

Figure 2:
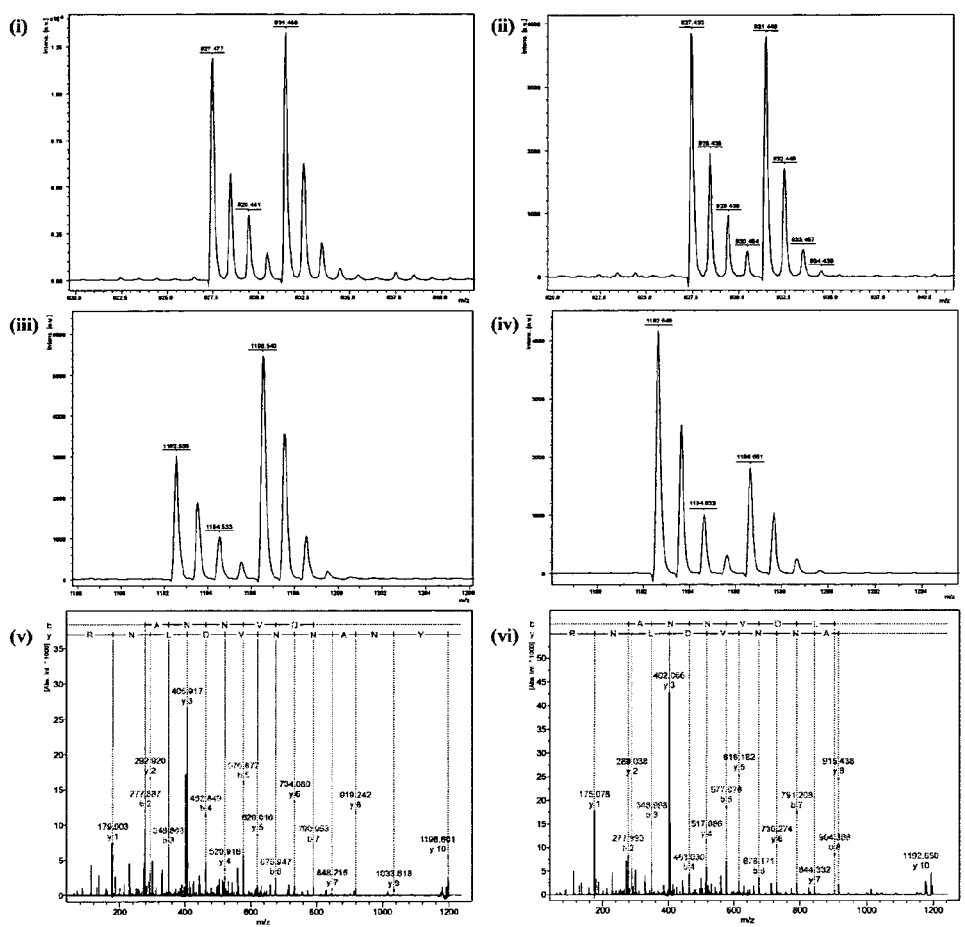
FIG. 2: Typical forward and reverse MS and MS/MS spectra from *P. gingivalis* sample. (i,ii) Zoomed portion of mass spectra showing the [M+H]+ parent precursor ion of the normal and reverse labelled peptide GNLQALVGR belonging to PG2082 and showing the typical 4 Da mass difference in a 1:1 ratio (iii,iv) mass spectrum showing the [M+H]+ parent precursor ion of the normal and reverse labelled peptide YNANNVDLNR belonging to PG0232 and showing the typical 4 Da mass difference in a 2:1 ratio (v, vi) MS/MS spectrum of heavy labelled (+2 18O) YNANNVDLNR and unlabelled YNANNVDLNR peptide characterized by the 4 Da shift of all Y ions.

FIG. 2 shows typical MS and MS/MS spectra of two normal and reverse labelled peptides from the biofilm/planktonic samples illustrating the typical reverse labelling pattern. As with the BSA data, it could be seen that there was a high level of double $^{18}O$ incorporation with the average mixed incorporation calculated to be <15% for all peptides, confirming that the $^{16}R\ O/^{18}O$ proteolytic labelling method was also effective with complex samples (data not shown). The predominance of doubly labelled peptides was further confirmed by the relatively few Mascot hits to the +2 Da species. MS/MS spectra of the heavy labelled peptides further revealed the expected +4 Da shifts in the Y ions (FIG. 2).

Correlation Between Technical Replicates

Figure 3:
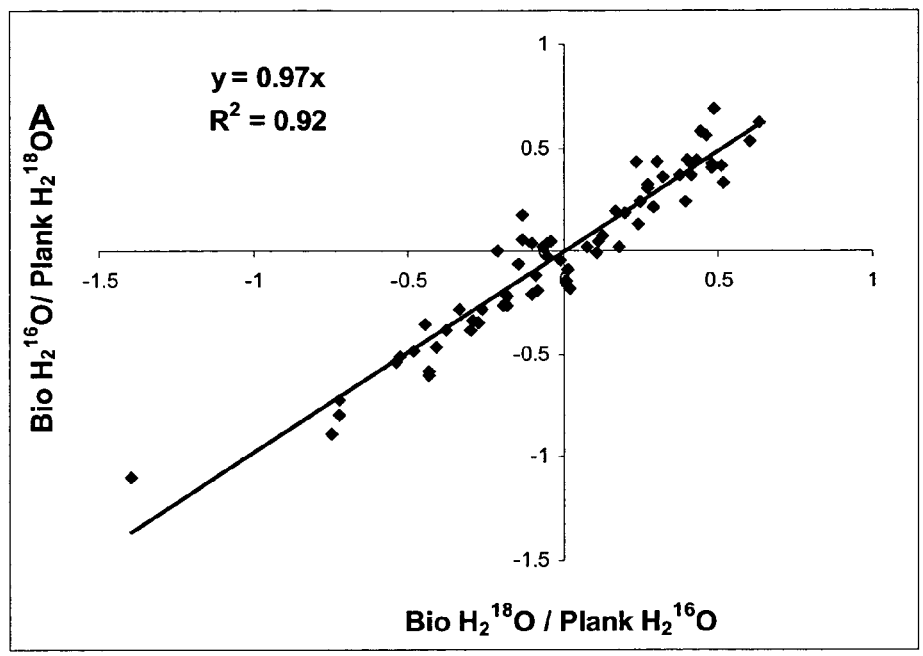
FIG. 3: Correlation of normal/reverse labelled technical replicates. Log 10 transformed scatter plot comparison of peptide abundance ratio of the normal (Bio18, Plank16) and reverse (Plank18, Bio16) labelling for both biological replicates. The abundance ratios of the reverse labelled peptides have been inversed for a direct comparison. (A) Biological replicate 1 (B) Biological replicate 2
Figure 3:
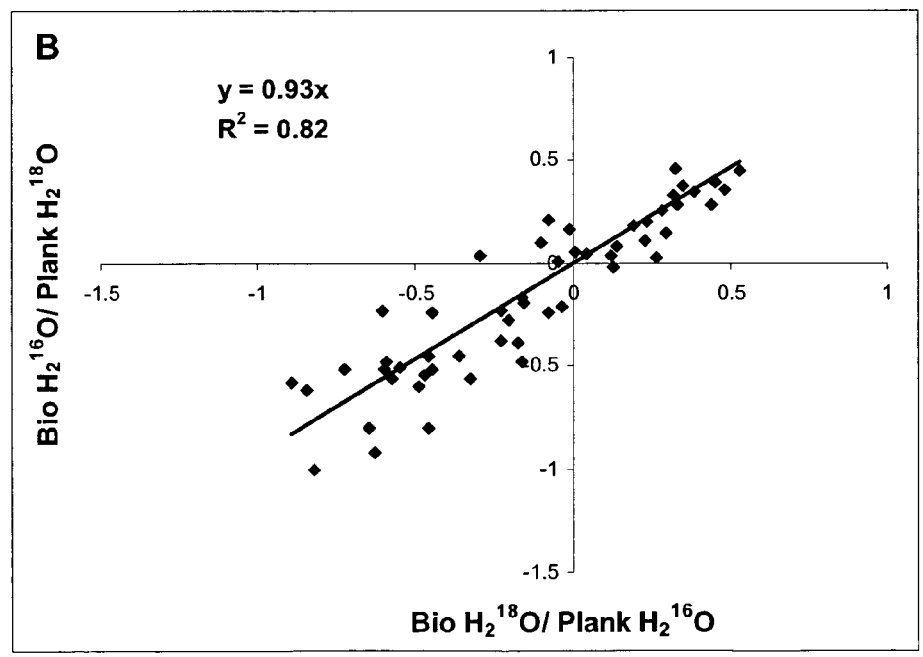

To compare technical replicates of the biological data, the $Log_{10}$ transformed protein abundance ratios of each pair of normal and reverse labelled experiments were plotted against each other (FIG. 3). Linear regression of these plots indicated that each pair is highly correlated with $R^2$ values of 0.92 and 0.82 for biological replicate 1 and 2, respectively. The slope of each linear fit was also similar to the expected value of 1.0 at 0.97 and 0.93 for biological replicate 1 and 2, respectively indicating no labelling bias between the technical replicates (FIG. 3). The protein abundance ratios from the technical replicates were averaged to give a single ratio for each biological replicate.

Correlation of Biological Replicates

Figure 4:
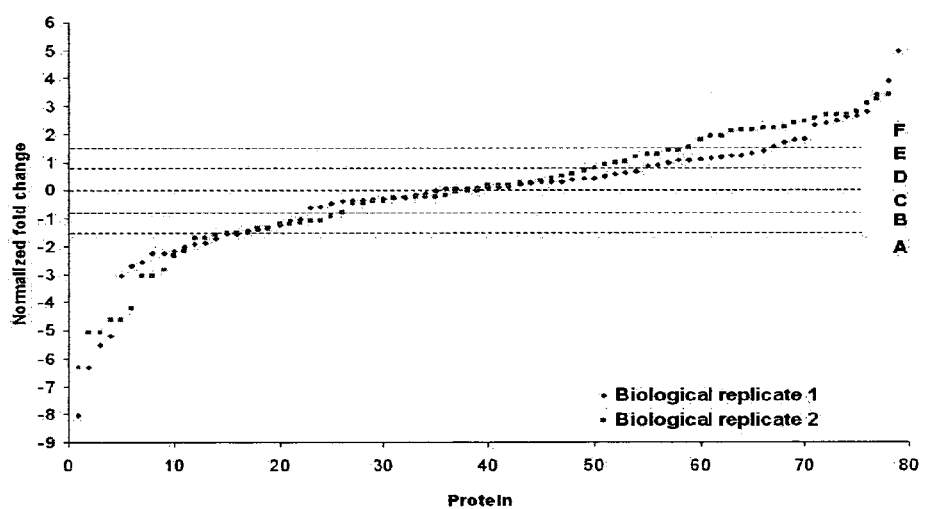
FIG. 4: Distribution and correlation of protein abundances of biological replicates. (A) Normalized average fold change for the 81 quantifiable proteins identified in both biological replicates displayed a Gaussian-like distribution. The abundance ratio of each protein was further normalized to zero (R−1) and ratios smaller than 1 were inverted and calculated as (1−(1/R)) (18). All 81 quantifiable proteins from each biological replicate were sorted by increasing ratios (Biofilm/Planktonic) and divided equally into six groups with equal number of proteins (A-F). Groups C and D represents proteins not significantly regulated (<3 SD from 1.0). (B) Distribution of proteins based on rankings. Insert: ranking table for the determination of similarity between both biological replicates. Proteins were ranked in descending order with 1 having the highest similarity when both biological replicates fell within the same group and 6 having the least similarity.
Figure 4:
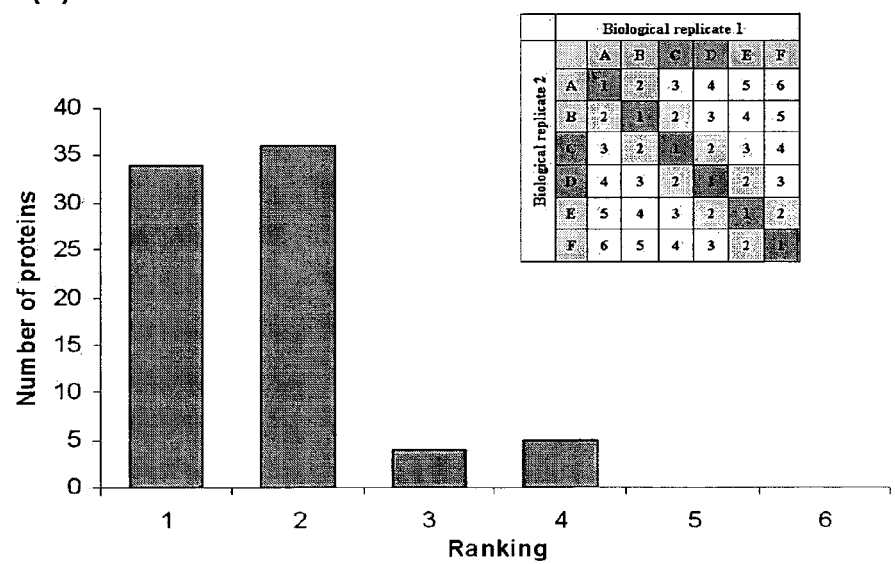
Figure 5:
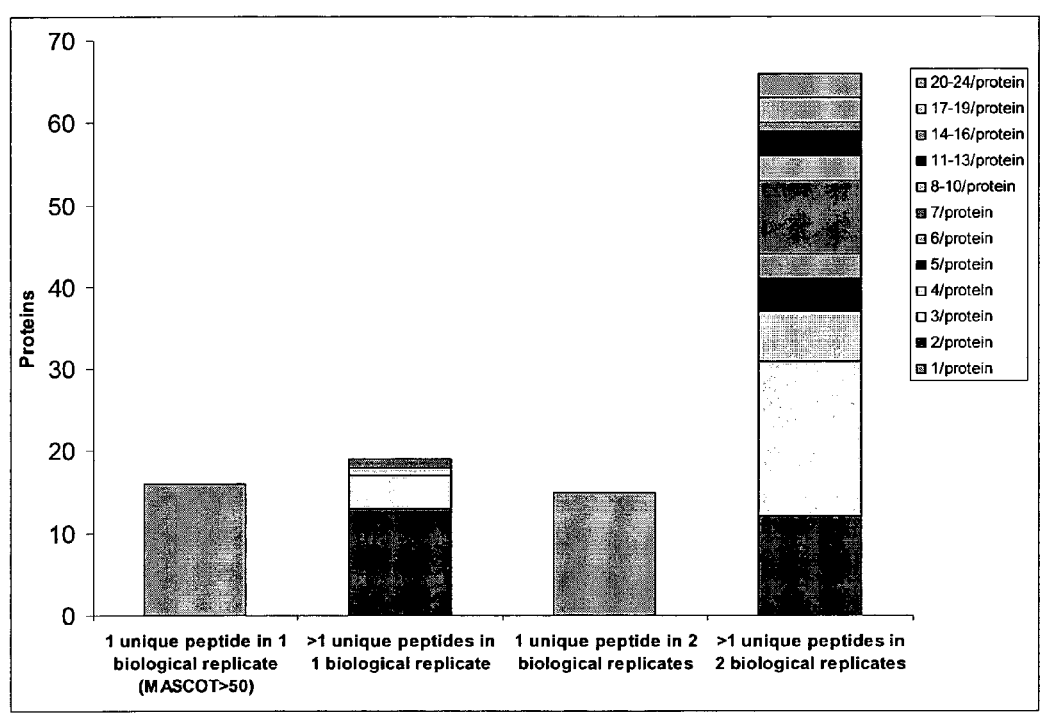
FIG. 5: Breakdown of the 116 proteins identified in this study based on identification in one or both biological replicates and number of unique peptides identified. The proteins identified from both biological replicates (81) are presented in table 2. Legend shows number of unique peptides identified per protein.

Before comparing the average data for the two biological replicates, the protein abundance ratios of each biological replicate were normalized to give an average mean ratio of 1.0. A plot of the normalized protein abundance ratios from both the biological replicates exhibits a Gaussian-like distribution closely centered at zero (FIG. 4A) similar to that described by others (40,41). There was a significant positive correlation between the two biological replicates (Pearson's correlation coefficient r=0.701, p<0.0001) indicating that the growth of the biofilm/planktonic cultures and all downstream processing of the samples could be reproduced to a satisfactory level. To determine which proteins were consistently regulated in the two biological replicates, a simple ranking chart was constructed where proteins were divided into 6 groups (A-F) according to their abundance ratio and then ranked 1-6 according to group-based correlation, with those ranked 1 having the highest similarity when a protein from both biological replicates fell within the same group (FIG. 4B). Using the ranking chart, we were able to determine that 34 out of 81 (42%) of the proteins identified from both replicates were ranked number one, considerably higher than the value expected for a random correlation which would be 17% (or ⅙). The majority of the remaining proteins were ranked number two, and therefore in total, 70 proteins (86.4%) were considered to be similarly regulated between the two experiments (ranked 1 or 2; Table 2).

Based on the measured standard deviation (±0.26) of the 2:1 BSA labelling experiment (Table 1), protein abundance changes were deemed to be biologically significant when they differed from 1.0 by >3 standard deviations (either >1.78 or <0.56) (18,42). Using this criteria, the abundance of 47 out of the 81 proteins identified in both replicates were significantly changed (based on the average ratios), and of these, 42 were ranked either 1 or 2 (Table 2). Of the 42 proteins ranked 1 and 2, 24 had significantly increased in abundance and 18 had decreased in abundance.

Enzymes of Metabolic Pathways Showing Co-Ordinated Regulation

Figure 6:
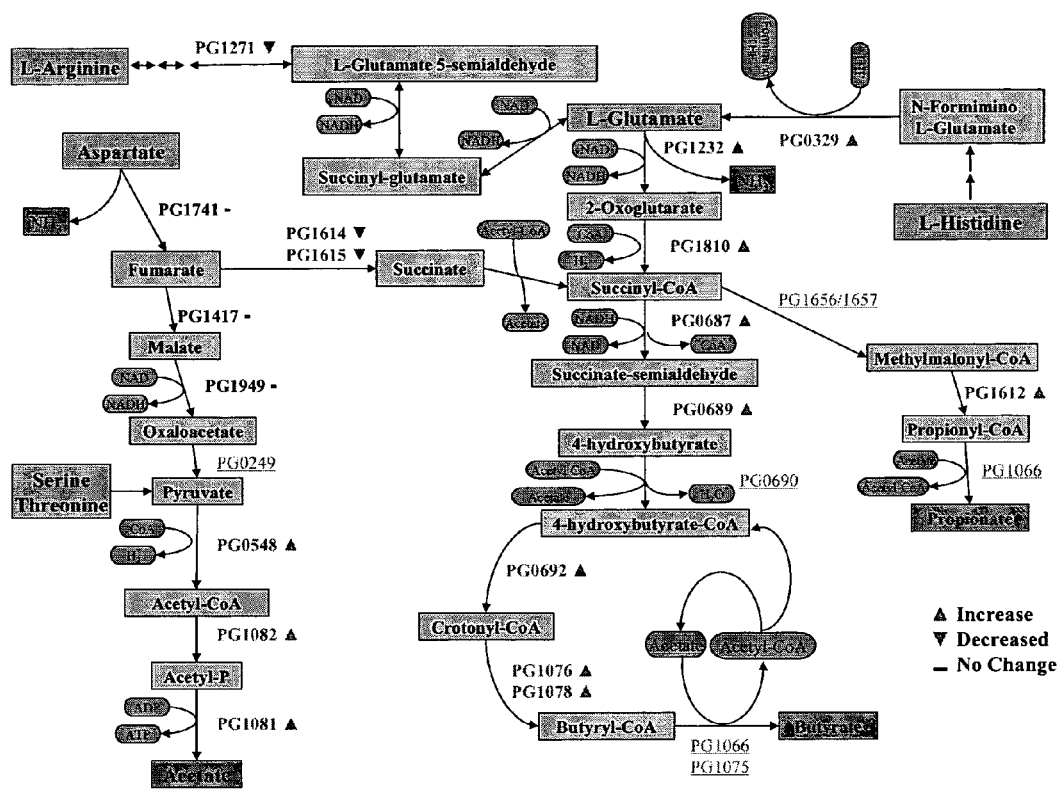
FIG. 6: The catabolic pathways for glutamate and aspartate fermentation in $P.$ $gingivalis$. Identified enzymes catalysing each step are represented by their TIGR accession number as seen in Table 3. Underlined accession number indicates enzymes that were detected in the another proteomic analysis but not in the ICAT studies.

Twenty proteins involved in the glutamate/aspartate catabolism were identified in the haem-limited vs haem-excess study using ICAT labelling strategies (Table 3). Of those, enzymes catalyzing six of the eight steps directly involved in the catabolism of glutamate to butyrate were identified and found to have increased 1.8 to 4 fold under haem-limitation (FIG. 6, Table 3). Although the other two catalytic enzymes (PG0690, 4-hydroxybutyrate CoA-transferase and PG1066, butyrate-acetoacetate CoA-transferase) were not detected using ICAT, they were found to be present in a separate qualitative study at comparable high ion intensities to those proteins reported in Table 3 and belong to operons shown to be upregulated. On the other hand, the effect of haem-limitation on the abundances of the enzymes of the aspartate catabolic pathway was mixed, with the enzymes catalyzing the breakdown of aspartate to oxaloacetate in the oxidative degradation pathway being unchanged and the enzymes involved in the conversion of pyruvate to acetate showing an increase of 2 to 4.4 fold.

The abundance of two iron containing fumarate reductase enzymes, FrdA (PG1615) and FrdB (PG1614) that together catalyse the conversion of fumarate to succinate via the reductive pathway from aspartate, was significantly reduced in cells cultured in haem-limitation (FIG. 6, Table 3). These two proteins, that are encoded in an operon (Baughn et al., 2003), show similar changes in abundance in response to haem-limitation (FrdA L/E=0.35; FrdB L/E=0.25).

Analysis of Organic Acid End Products

The amounts of acetate, butyrate and propionate in the spent culture medium of $P.$ $gingivalis$ grown under haem limitation were 13.09±1.82, 7.77±0.40 and 0.71±0.05 mmole/g cellular dry weight, respectively. Levels of acetate, butyrate and propionate in the spent culture medium of $P.$ $gingivalis$ grown in haem excess were 6.00±0.36, 6.51±0.04 and 0.66±0.07 mmole/g cellular dry weight, respectively.

Effects of Frd Inhibiting Agents on $P.$ $gingivalis$ Growth

Figure 7:
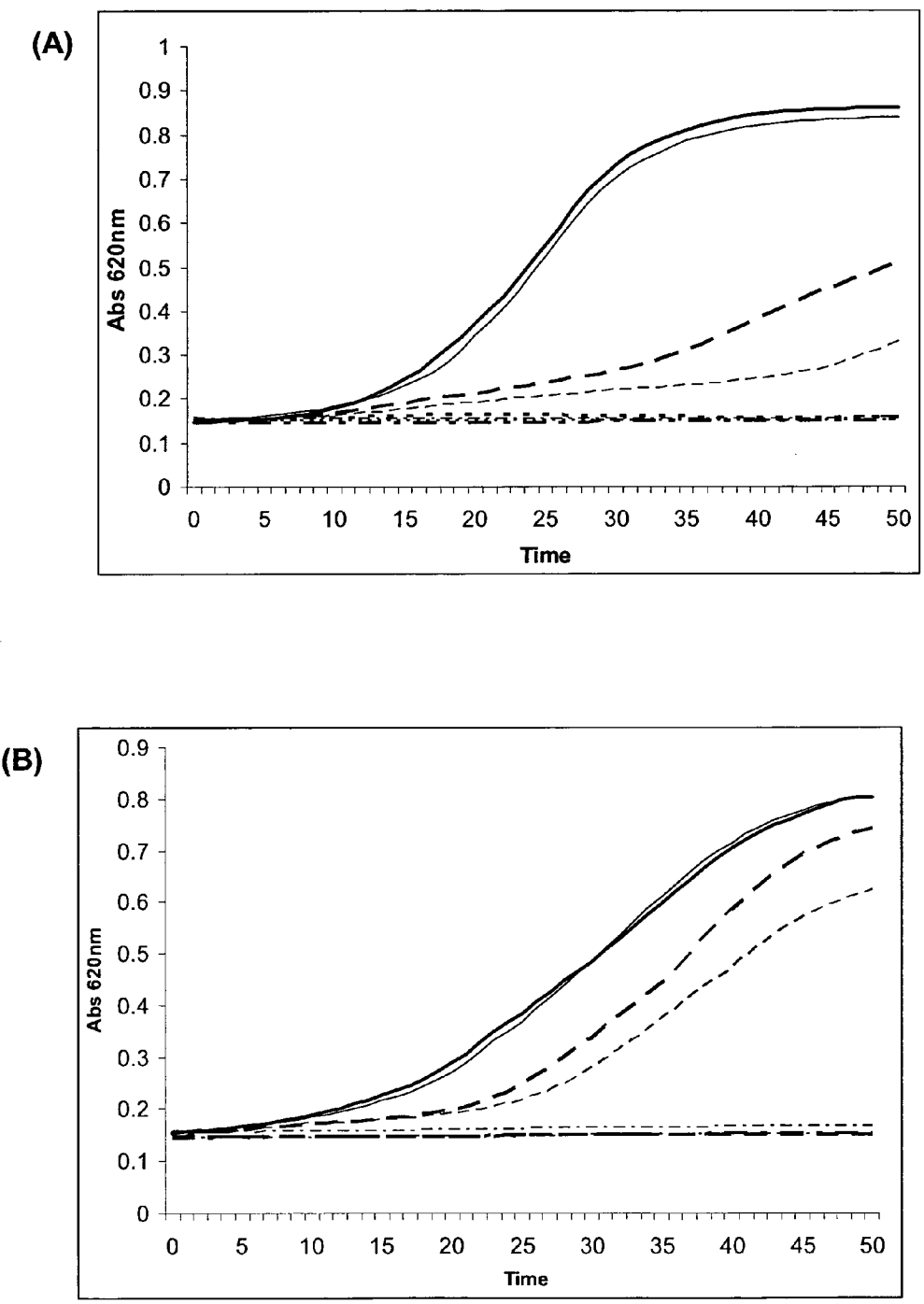
FIG. 7: Effect of oxantel on cell growth of $P.$ $gingivalis$ W50 (A) and ATCC 33277 (B) over 50 h. The concentrations used were from 15.625 to 1000 µM. Negative control used was 4 µL DMSO. MIC and MGT of $P.$ $ginvigalis$ was as noted in Table 7 and 8. Result shows mean of two biological replicates carried out on different days (n=10). (———— DMSO, - 15.625 µM, — —31.25 µM, — — — — 62.5 µM, ▪ ▪ ▪ ▪ 125 µM, ▪ ▪ ▪ ▪ ▪ ▪ ▪ 250 µM, — ▪ ▪ 500 µM, — ▪ — ▪ — 1000 µM)
Figure 8:
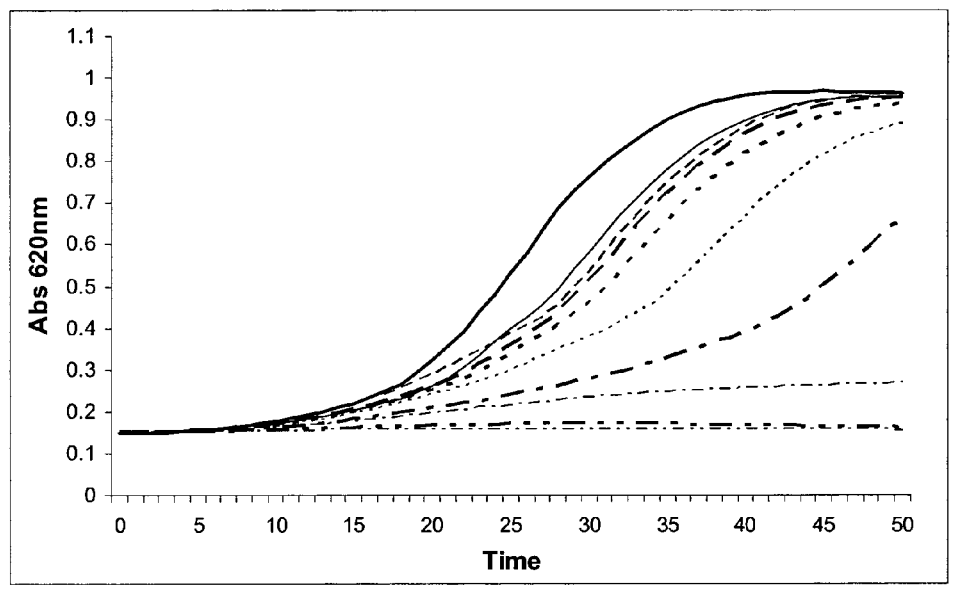
FIG. 8: Effect of morantel on cell growth of $P.$ $gingivalis$ over 50 h. The concentrations used were from 15.625 to 1000 µM. Negative control used was 4 µL DMSO. MIC and MGT of $P.$ $gingivalis$ was as noted in Table 7. (———— DMSO, - 19.53 µM, — —39.06 µM, — — — — 78.13 µM, ▪ ▪ ▪ ▪ 156.25 µM, ▪ ▪ ▪ ▪ ▪ ▪ ▪ 312.5 µM, — ▪ ▪ 625 µM, — ▪ — ▪ — 1250 µM, — ▪ ▪ 2500 µM, — — — ▪ 5000 µM)
Figure 9:
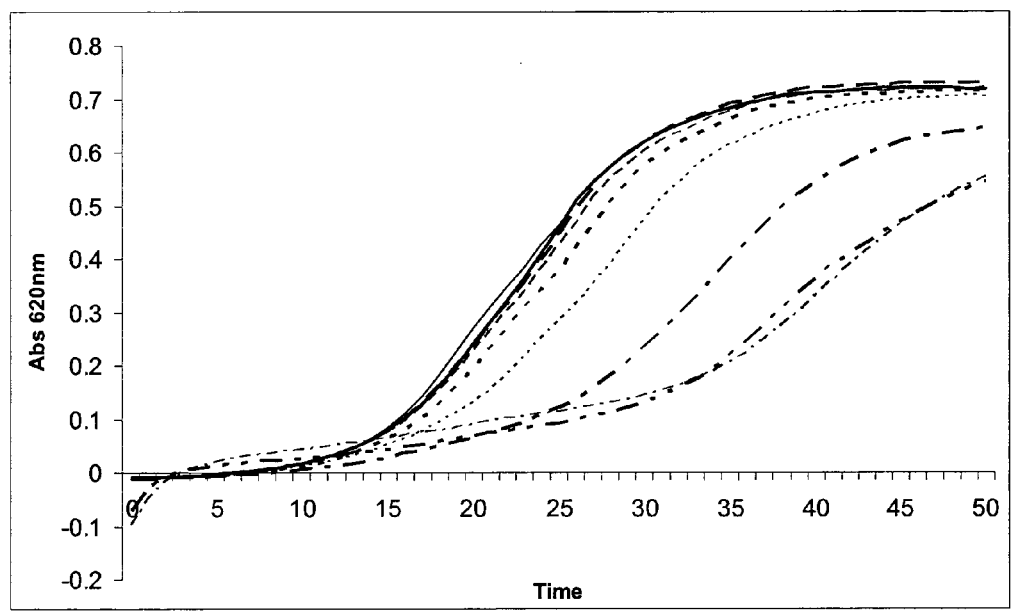
FIG. 9: Effect of thiabendazole on cell growth of $P.$ $gingivalis$ over 50 h. The concentrations used were from 31.25 to 4000 µM. Negative control used was 4 µL DMSO. MIC and MGT of $P.$ $gingivalis$ was as noted in Table 7. (———— DMSO, - 31.25 µM, — —62.5 µM, — — — — 125 µM, ▪ ▪ ▪ ▪ 250 µM, ▪ ▪ ▪ ▪ ▪ ▪ ▪ 500 µM, — ▪ ▪ 1000 µM, — ▪ — ▪ — 2000 µM, — ▪ ▪ 4000 µM)

The effect of different concentrations of the three anthelmintics oxantel, morantel and thiabendazole on the growth of $P.$ $gingivalis$ W50 over 50 hrs was shown in FIGS. 7, 8 and 9. The effect of DMSO on growth was negligible as seen in the similar MGT of $P.$ $gingivalis$ with previous reported studies and the W50 alone (43,44). The most profound effect of these three inhibiting agents on the growth of $P.$ $gingivalis$ is oxantel (FIG. 7). From the growth curves, it is clear that there is positive inhibition of oxantel on the growth of $P.$ $gingivalis$ at concentrations of more than 15 µM. Minimal inhibitory concentrations (MIC) of oxantel was determined as previously described (45) to be 112 µM. There was also significantly correlation of increasing concentration of oxantel with higher MGT as seen for subMICs of oxantel (FIG. 7A). The bactericidal effect of morantel was comparably lower than oxantel with MIC of ~3 mM but still shows significant inhibitory effects at subMICs (FIG. 8). Thiabendazole appears not to have very significant inhibitory effects on the growth of $P.$ $gingivalis$ and apparently requiring more than 1 mM for slight inhibitory effects on the growth (FIG. 9). In conclusion, the inhibitory effects of the different Frd inhibiting agents were estimated to be in the order of oxantel>>morantel>thiabendazole.

Figure 10:
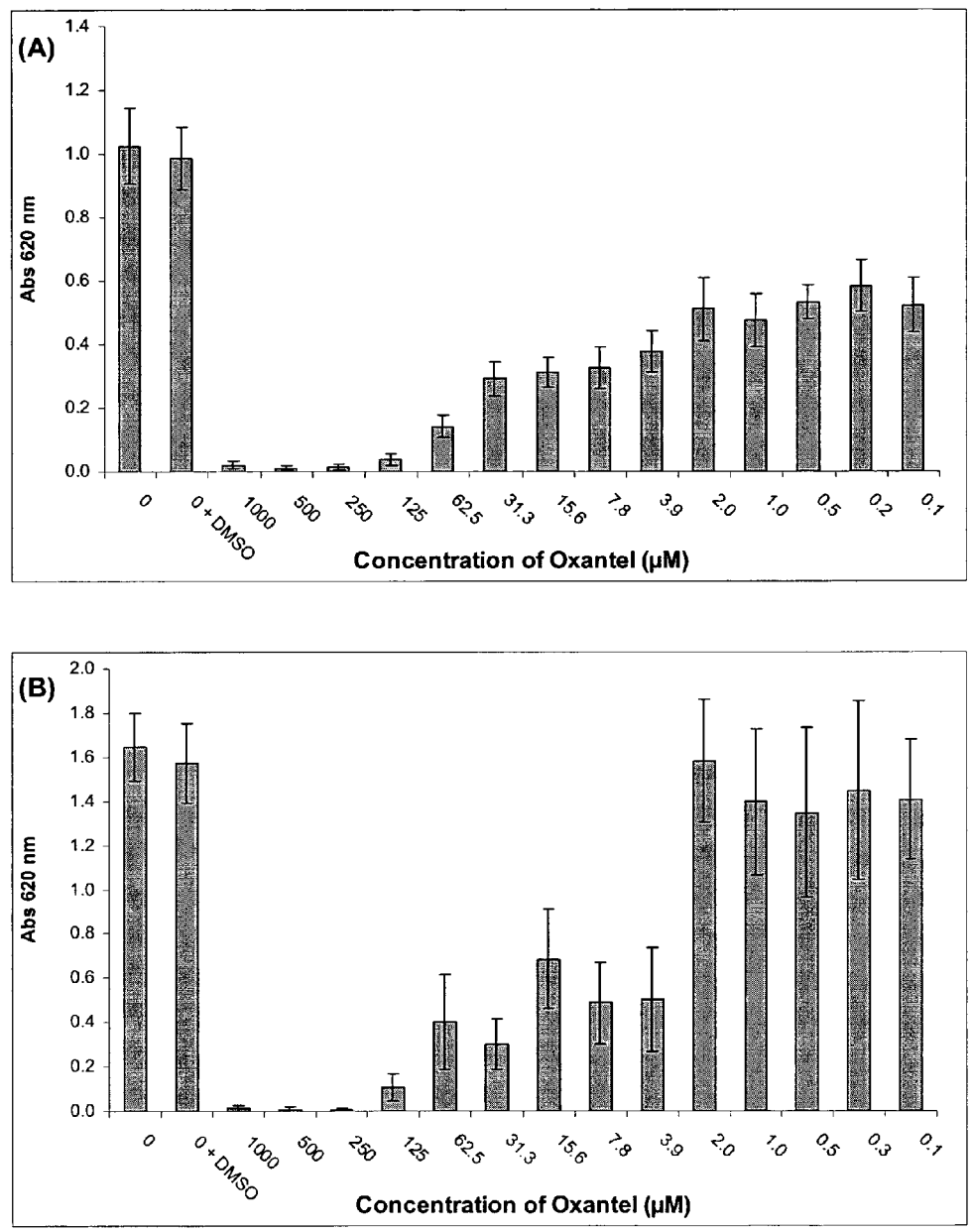
FIG. 10: Effects of oxantel on biofilm formation by $P.$ $gingivalis$ strain 33277 (A) 24 h biofilm (B) 48 h biofilm. Biological replicates of the assay were carried out and error bars representing the standard deviations of both biological replications (n=12).

Effects of Sub Minimal Inhibitory Concentrations of Oxantel on Biofilm Formation Oxantel, having the most profound effects on $P.$ $gingivalis$ growth was used to study its effects on biofilm formation In the biofilm test, $P.$ $gingivalis$ strain ATCC 33277 was used in place of W50 since the latter forms biofilms only poorly under most circumstances. As the growth inhibitory effect of oxantel on strain ATCC 33277 is similar to W50 in planktonic assays at 125 µM (FIG. 7B), it therefore represents a good model to study the effects of oxantel on biofilm formation. Oxantel at sub minimal inhibitory concentrations (SubMIC) of as low as 0.1 µM significantly reduced the biofilm mass at 24 h (FIG. 10A) although concentrations of 3.9 µM or higher were necessary to have an inhibitory effect on the biofilm mass at 48 h (FIG. 10B).

Effect of Oxantel on Biofilm Dispersal

Figure 11:
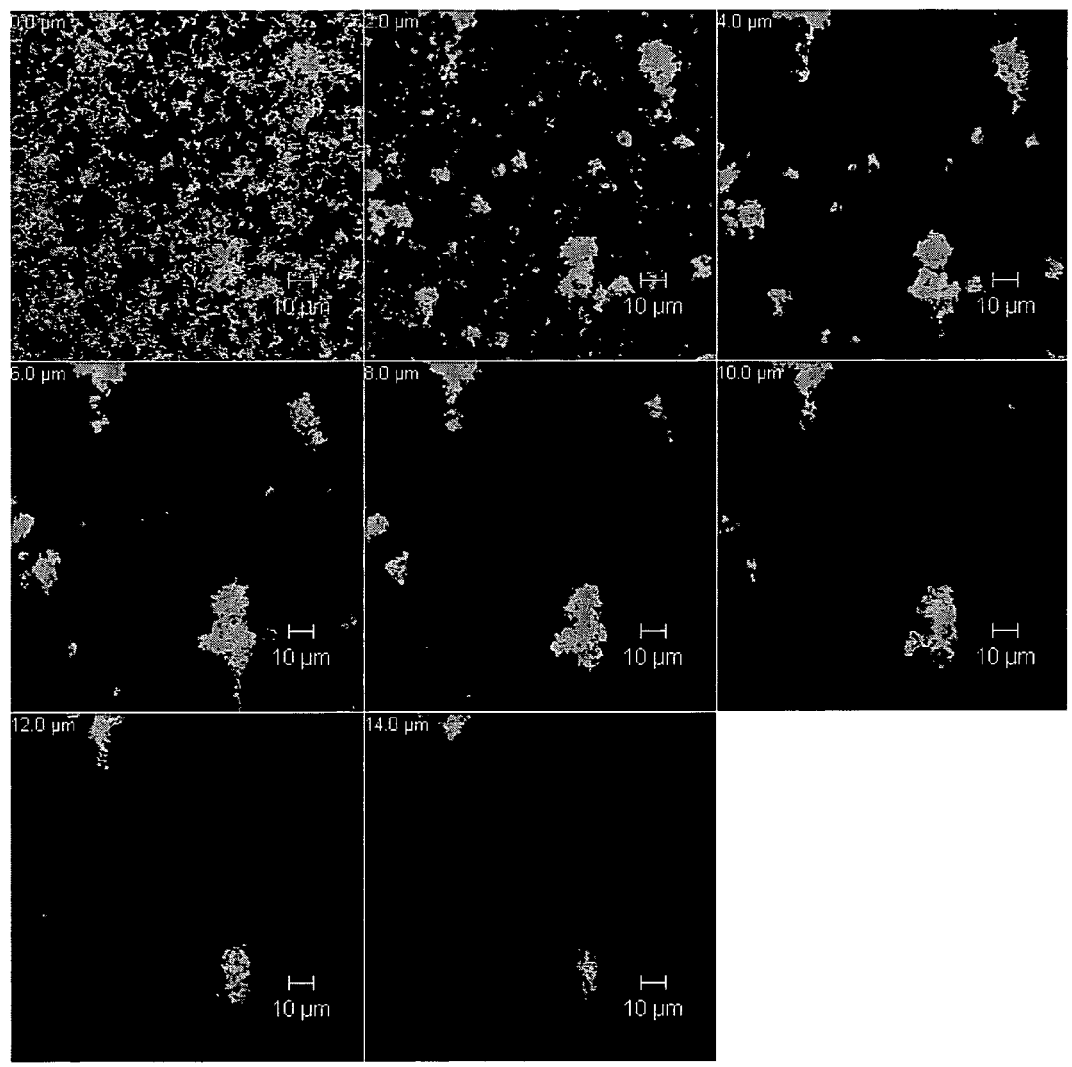
FIG. 11: CLSM image of the control ATCC 33277 treated with only water and stained with Baclight. Images are maximum projections of the entire z-stack obtained at 2 µm intervals. Scale bar (white)=10 µm.
Figure 12:
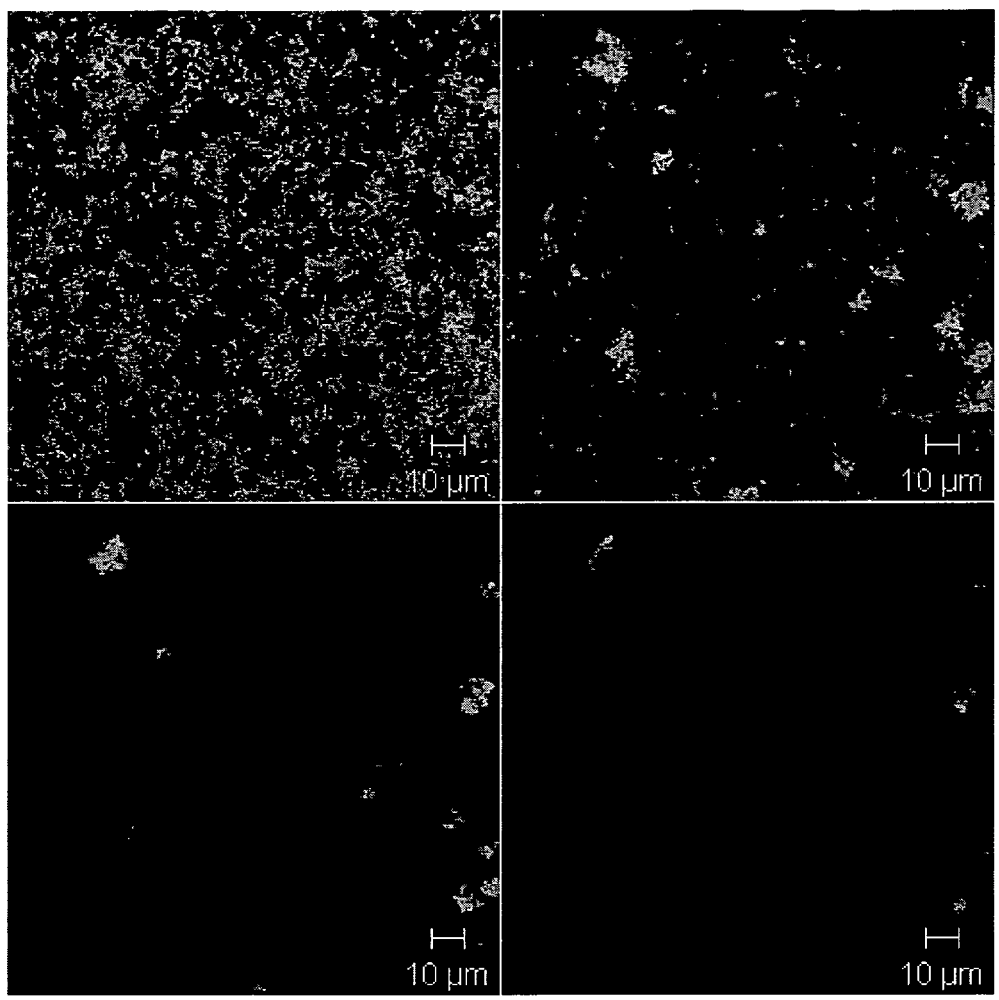
FIG. 12: CLSM image of ATCC 33277 treated with 125 µM Oxantel and stained with Baclight. Images are maximum projections of the entire z-stack obtained at 2 µm intervals. Scale bar (white)=10 µm
Figure 13:
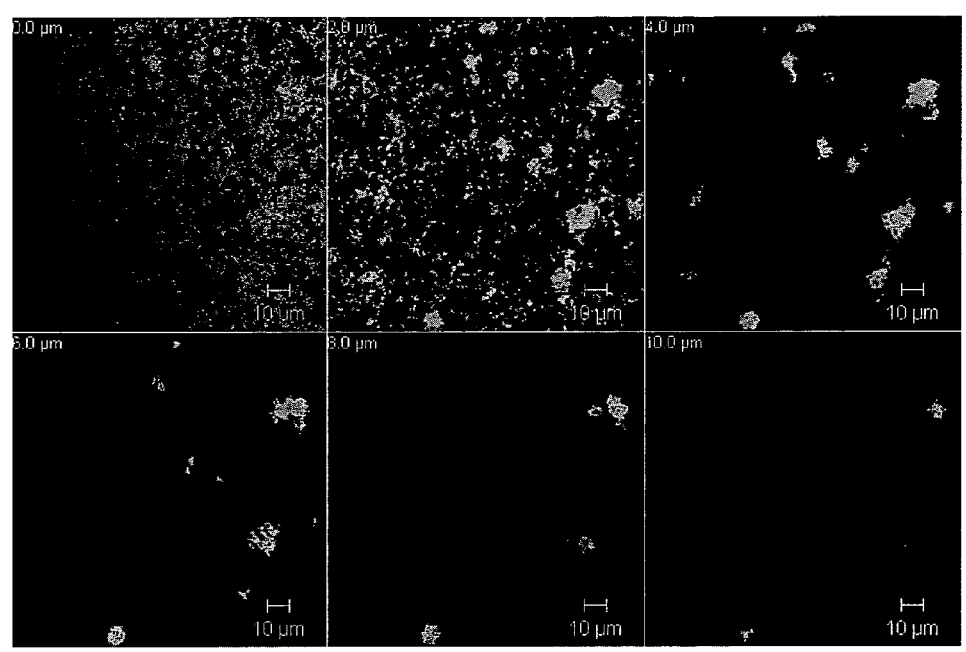
FIG. 13: CLSM image of the ATCC 33277 treated with 12.5 µM Oxantel and stained with Baclight. Images are maximum projections of the entire z-stack obtained at 2 µm intervals. Scale bar (white)=10 µm

To more closely study the effects of SubMIC of Oxantel, on $P.$ $gingivalis$ biofilms a flowcell culture system was used. There was a significant reduction in the biofilm depth and size of microcolonies when the mature biofilm was treated with Oxantel (P<0.01) whereas there was no significant difference in the number of microcolonies between the control and treated samples (FIGS. 11-13, Table 6).

Figure 14:
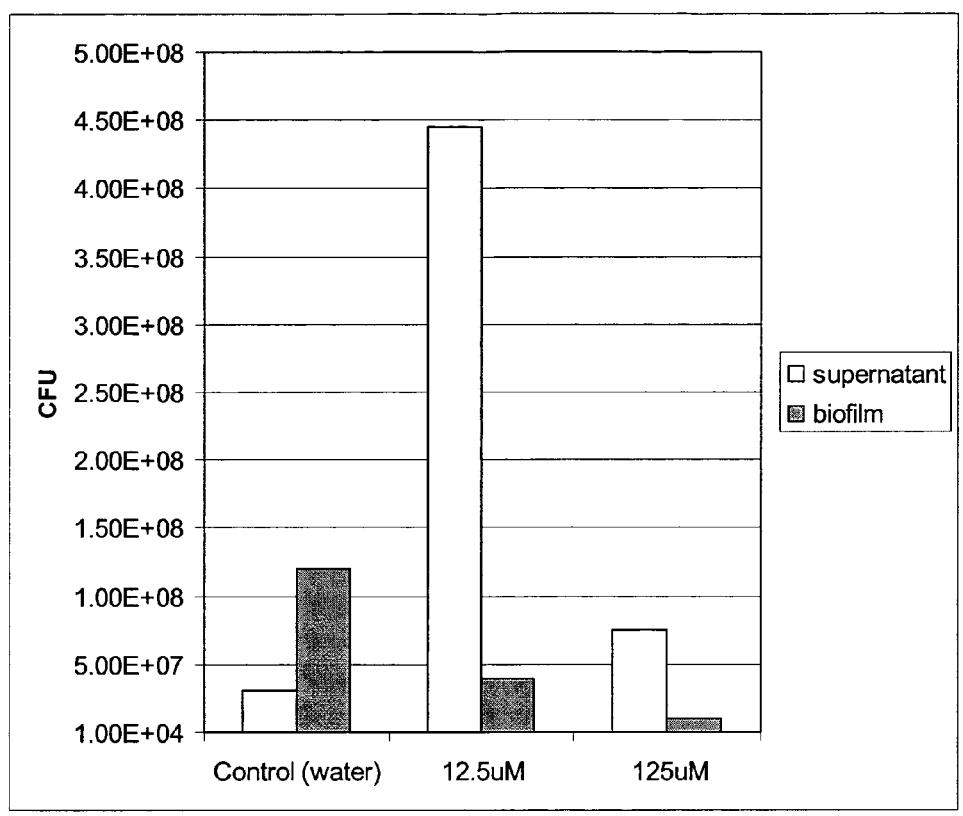
FIG. 14: Colony forming units of $P.$ $gingivalis$ after Oxantel treatment based on a static 24 well assay.

$P.$ $gingivalis$ cells released from the biofilm remained viable especially for the 12.5 µM Oxantel treated biofilm (FIG. 14). The non treated control cells appeared more resistant to dispersal as compared to Oxantel treated cells. The number of recovered cells from the biofilm is also consistent with that seen under the CLSM (FIGS. 11-13) with significantly higher number of cells in the control sample.

The above results illustrate the changes in protein abundance that occur when planktonic $P.$ $gingivalis$ cells adhere to a solid surface and grow as part of a mature monospecies biofilm. It is the first comparative study of bacterial biofilm versus planktonic growth to utilize either the geLC MS approach of Gygi's group (46) or the $^{16}O/^{18}O$ proteolytic labelling method to determine changes in protein abundances as all other such studies published to date have utilized 2D gel electrophoresis based methods (10-12). A two technical replicate and two biological replicate 16O/$^{18}O$ reverse labelling approach was successfully employed to quantitate and validate the changes in protein abundance.

Continuous Culture of $P.$ $gingivalis$

In this study $P.$ $gingivalis$ W50 was cultured in continuous culture as opposed to the more traditional methodology of batch culture. Batch culture introduces a large range and degree of variation into bacterial analyses due to interbatch variables such as: size and viability of the inoculum, exact growth stage of the bacterium when harvested, levels of available nutrients in the medium and redox potential of the medium, amongst other factors. In continuous culture the bacterium is grown for many generations under strictly controlled conditions that include growth rate, cell density, nutrient concentrations, temperature, pH and redox potential. (44, 47,48). A previous study has demonstrated a high level of reproducibility of $Saccharomyces$ $cerevisiae$ transcriptomic analyses continuously cultured in chemostats in different laboratories (49). Furthermore in our study the growth of both biofilm and planktonic cells was carried out in a single fermentation vessel, reducing variability as compared to separate cultivations. The consistent changes in $P.$ $gingivalis$ cell envelope protein abundances between biological replicates of 86.4% of the identified proteins (ranked 1 and 2) seen in this study illustrate the applicability of the continuous culture system and the $^{16}O/^{18}O$ proteolytic labelling strategy to the analysis of the effect of biofilm growth on the *P. gingivalis* proteome.

Efficiency of $^{18}O$ Labelling

The basic proteomic method employed in this study was the geLC MS method (46,50) due to the high resolution and solubility of membrane proteins that the SDS-PAGE method affords. This method was combined with a single $^{18}O$ labelling reaction during the in-gel digestion procedure similar to that described by others (26-29). Efficient labelling should result in the incorporation of two $^{18}O$ atoms into the C-terminus of each peptide and should be resistant to back-exchange with $^{16}O$. This was found to be the case in our study with BSA where the level of single $^{18}O$ atom incorporation was estimated to be <7% and the mean ratios obtained for various BSA experiments were found not to significantly favor $^{16}O$ (Table 1) suggesting that back exchange with normal water was not a problem. Similar results were also obtained for the biological samples. A crucial step for efficient $^{18}O$ labelling was the need for the complete removal of the natural $H_2^{16}O$ followed by resolubilization of the protein in $H_2^{18}O$ before tryptic digestion employing a "single-digestion" method. Although a number of studies have used a "double digestion" method (51,52), the single digestion method has the advantage of giving a higher efficiency of $^{18}O$ labelling as in the double digestion method some tryptic peptides were unable to exchange either of their C-terminal $^{16}O$ atoms for an $^{18}O$ atom after the initial digestion (53). We further utilized an in-gel digestion method where the protein is retained in the gel matrix during the initial dehydration step using organic solvents as in any standard in-gel digestion protocol. Complete removal of any trace natural $H_2^{16}O$ was achieved through lyophilization by centrifugation under vacuum while the protein was still within the gel matrix to prevent further adsorptive losses during the initial lyophylization step. Rehydration and in-gel digestion was carried out in $H_2^{18}O$ containing a large excess of trypsin which was also reconstituted in $H_2^{18}O$. During the digestion procedure, tryptic peptides liberated from the gel after the incorporation of the first $^{18}O$ atom can undergo the second carbonyl oxygen exchange process mediated by the excess trypsin. This should promote the replacement of the second carbonyl oxygen since peptides liberated would have higher solubility than proteins thereby resulting in a higher level of doubly $^{18}O$ labelled tryptic peptides (FIGS. 1 and 2; (54)). In order to prevent back exchange with normal water, trypsin was deactivated by boiling which has been previously shown to be effective (51,54). In addition, the dried, deactivated mix was only resuspended and mixed immediately prior to injection onto a nanoLC to minimize spontaneous exchange, although this spontaneous exchange has been shown to be low (15,40).

Reverse Labelling

In the case of stable isotope labelling and quantification using MS, errors are potentially introduced during the labelling and ionization process. These errors include the potential different affinity of the label and the possible suppression effect of the heavy or light labelled peptides during the MALDI process (13,55). Traditional technical replicates which involve repeating the same labelling could result in an uncorrected bias towards a particular label or increased random error of specific peptides due to contaminating peaks. Our normal and reverse labelled technical replicates demonstrated a high degree of correlation with scatter plot gradients of 0.97 ($R^2$=0.92) and 0.93 ($R^2$=0.82) for biological replicates 1 and 2, respectively (FIG. 3) which is close to the expected ratio of 1.0 for no labelling bias. These gradients also indicate that the method was reproducible with respect to protein estimation, gel loading, gel excision and in-gel digestion. The lack of bias suggests normalization routines like dye swap or LOWESS data normalization routinely used in microarray experiments (35) might be unnecessary. However samples that are considerably more complex than the bacterial cell envelopes used in this study may still require reverse labelling validation as when one considers the influence of minor contaminating peptides on the calculation of the 18O/$^{16}O$ ratios and the need to verify peptides with extreme changes. The reverse-label design in addition to providing an estimate and means for correcting systematic errors had the further benefit of allowing both the heavy and light labelled peptides to be readily identified since the MS/MS acquisition method selected only the most intense peptide in each heavy/light pair to fragment. In this way the possibility of incorrect assignment is reduced. To our knowledge, this is the first report of reverse $^{16}O/18O$ labelling in a complex biological sample other than the recent quantitation of seventeen cytochrome P450 proteins (26,30).

Biofilm vs Planktonic Culture

We have demonstrated a strong positive correlation between the biological replicates (r=0.701, p<0.0001) indicating that there was reproducibility in biofilm formation and development. This was also seen by the finding that 70 out of 81 quantifiable proteins were observed to exhibit similar ratios in both biological replicates (Table 2, ranked 1 or 2). More than three quarters of the *P. gingivalis* proteins identified in this study were identified by >2 unique peptides, further increasing the confidence of identification and quantification of this labelling procedure. Of the 81 proteins consistently identified from both biological replicates, 47 significantly changed in abundance from the planktonic to biofilm state. The change in abundance of a percentage of the detected proteome, especially in the cell envelope, is consistent with other studies on biofilm forming bacteria such as *Pseudomonas aeruginosa*, where over 50% of the detected proteome was shown to exhibit significant changes in abundance between planktonic and mature biofilm growth phases. (12). We further observed a wide range of responses in the cell envelope proteome of *P. gingivalis* to growth as a biofilm. A number of proteins previously demonstrated to be altered in abundance in response to biofilm culture were also found to have changed in abundance in our study. Remarkably some proteins were observed to have changed in abundance by up to fivefold (Table 2) suggesting some major shifts in the proteome in response to biofilm culture.

Metabolism

The principal source of energy for *P. gingivalis* is derived from the fermentation of amino acids which are obtained in peptide form by the proteolytic hydrolysis of host proteins (47,80,81). The major catabolic pathways of *P. gingivalis* are the fermentation of glutamate and aspartate where glutamate is metabolized to butyrate, propionate and ammonia, and aspartate metabolized to butyrate, propionate, acetate and ammonia (FIG. 6). Previous reports have shown that *P. gingivalis* preferentially utilizes aspartate/asparagine, glutamate/glutamine, threonine, serine, leucine and valine from the culture medium (47,81,82).

Two *P. gingivalis* proteins involved in glutamate catabolism, PG1076 (L/E=1.8) and PG1078 (L/E=2.0) significantly increased in abundance during haem-limitation. These proteins are encoded by genes arranged in a predicted large operon of 15 genes. Upstream of these genes are two genes encoding a hypothetical protein and a conserved hypothetical protein whose abundance also increased during haem-limitation (PG1067, L/E=2.4 and PG1068, L/E=1.7, respectively). Analysis of this large operon further revealed the presence of a putative Fur consensus binding region characteristic of many iron-regulated genes (83), which suggests that expression might be controlled by iron availability. Although we expected the fold change of all encoded proteins in an operon to be the same, this is not necessarily the case in all instances as the level of transcript sometimes does not correlate with the protein levels (84). This could be due to posttranslational modifications or stability of the transcript, allowing a substantial regulation of cellular events to occur at the protein level with no apparent change in the mRNA abundance.

The conversion of fumarate to succinate via the pathway from aspartate is catalysed by a heterotrimeric succinate-quinone oxidoreductase (SQOR) complex consisting of two cytoplasmic enzymes FrdA (1615) and FrdB (1614) and a transmembrane FrdC (1616). The abundance of the two cytoplasmic fumarate reductase enzymes, FrdA (PG1615) and FrdB (PG1614) was significantly reduced in cells cultured in haem-limitation (3 and 4 fold, respectively) and biofilm growth (17 and 5.9 fold, respectively). These two proteins, that are encoded in an operon (85), show similar changes in abundance in response to haem-limitation (FrdA L/E=0.35; FrdB L/E=0.25) and biofilm growth (FrdA B/P=0.06; FrdB B/P=0.17). Previous studies in *Bacteroides fragilis* have suggested that haem is required for the synthesis of the cytochrome-b-dependent Frd complex (86). It is therefore not surprising to see lower levels of Frd during haem-limitation growth conditions in *P. gingivalis* considering that it is unable to synthesize PPIX de novo. Growth studies of both *B. fragilis* and *P. gingivalis* have shown that they require haem for growth and that this requirement can be partially substituted by exogenous succinate (87,88). This observation was confirmed using *B. fragilis* Frd deficient mutants whose growth was not stimulated by haem but was stimulated by addition of succinate (85). Molar growth yield studies further showed that the *B. fragilis* Frd deficient mutants have a similar ATP yield to that of a haem-restricted wild-type strain. During optimum growth, succinate is converted to succinyl-CoA either for entry into energy producing pathways or for biosynthesis of essential amino acids (lysine and methionine). These studies demonstrate the importance of the conversion of aspartate to succinate for balanced growth. Under haem-excess conditions a portion of the aspartate catabolized by *P. gingivalis* is initially reduced via the fumarate reductase enzymes (FrdA and FrdB) to succinate and then catabolized via the glutamate pathway to produce butyrate (FIG. 6). The 3-4 fold decrease in abundance of these fumarate reductase enzymes during haem-limitation indicates that less of the aspartate would enter the glutamate catabolic pathway and as a consequence of this most of the aspartate catabolized would be converted via the oxidative pathway to acetate (FIG. 6). To test this hypothesis we carried out organic acid analysis on the spent culture media from *P. gingivalis* grown in continuous culture. This showed there was a two-fold higher level of acetate produced under haem-limitation (13.09±1.82 mmole/g cellular dry weight) compared with the level produced under haem-excess (6.00±0.36 mmole/g cellular dry weight), whilst the levels of the other major end products, butyrate and propionate were similar under both growth conditions. This is consistent with our hypothesis of a shift in the pathway used for aspartate fermentation. The increase in the abundance of the enzymes that catalyse the conversion of pyruvate to acetate (Acetate kinase PG1081, Phosphotransacetylase PG1082 and Pyruvate ferredoxin PG0548) is also consistent with the increased amounts of acetate found in the spent culture medium (Table 2; FIG. 6).

These results thus prompted us to investigate into ways to control the bacterium through inhibition of this delicate metabolic regulatory pathway.

Effects of Fumarate Reductase Inhibiting Agents on Growth

We have shown a 17.0 and 5.9 fold reduction in the abundance of the Frd complex (FrdA and FrdB, respectively) during biofilm growth of *P. gingivalis* which is even greater than the 3 and 4 fold reductions in FrdA and FrdB during haem-limitation growth. The consistent lower abundance of the Frd complex correlates with the diminished growth of the bacterium associated with the limitation of haem during both biofilm and haem-limited growth conditions. Smith et al. (89) have previously demonstrated that Frd activities of *Campylobacter* spp to be higher in cultures growing exponentially but decreased as it entered the stationary phase. It therefore suggests that Frd activity limits growth rate which highlights it to be an attractive new therapeutic target. Fumarate respiration is the most widespread type of anaerobic respiration and is the only metabolic intermediate known to serve as an electron acceptor yielding ~0.5 ATP/electron to form succinate as the end product (90). Shah and William (91) reported that *P. gingivalis* produced succinate from aspartate and Takahashi et al. (81) proposed that the succinate produced was converted to succinyl-CoA which was then converted into butyrate or propionate.

Anthelmintics usually used to cure helminthic infection in animals and humans were demonstrated to have inhibitory and bacteriocidal effects against *Helicobacter pylori* and *Campylobacter jejuni* (89,94). One of these drugs, oxantel has been shown to be an inhibitor of the fumarate reductase enzyme in *H. pylori* and *C. jejuni* presumably on the hydrophilic subunits of the Frd complex through unknown mechanisms (94-96).

Interestingly not all anaerobic bacteria possess Frd and some bacteria that possess Frd have alternative biochemical pathways for survival when Frd is inhibited (97,98). Therefore the discovery that the viability of *P. gingivalis* is severely affected in the presence of Frd inhibiting agents (FIG. 7-10) suggests the enzyme being absolute essential for growth and ATP contribution from the aspartate pathway could play a crucial role in the survival of *P. gingivalis*. As the Frd complex is absent in humans and other animals (92,93), Frd inhibiting agent provide a target against diseases caused by pathogens, especially those having an essential requirement for Frd.

Effects of Fumarate Reductase Inhibiting Agents on Biofilm Formation

The following illustrates the effect of Frd inhibiting agents on the ability of *P. gingivalis* to form biofilms. The reduction of biofilm mass at subMIC oxantel concentrations is very interesting as it suggests there is a minimal amount of Frd or energy required for optimum biofilm formation.

The partial inhibition of Frd by subMIC concentrations of Frd inhibiting agents could be translated as similar signals such in a nutrient poor environment. For example carbon regulated biofilm formation is well documented in a number of bacteria including *Pseudomonas aeruginosa* and *E. coli* and us mediated by transcriptional regulators such as RpoS, Crc and CsrA in during nutrient limitation (99-101). In *E. coli* the csrA gene encodes a global regulatory protein, CsrA (carbon storage regulator) which represses certain metabolic pathways such as glycogen synthesis and gluconeogenesis (101,102). Disruption of csrA in *E. coli* resulted in enhanced biofilm formation (101,103) and interestingly, activation of the CsrA homologue in *Salmonella enterica* serovar Typhimurium resulted in increased epithelial cell invasion due to the effects of CsrA on other targets (104,105). It is therefore very tempting to speculate that haem-limited *P. gingivalis* are less likely to form biofilms due to the lower ATP levels as a result of reduced Frd activity as such host cell invasion proteins including internalins are upregulated to promote escape into epithelial cells till end of nutrient deprivation.

There is a higher abundance of the glycolytic enzyme glyceraldehyde 3-phosphate dehydrogenase (GAPDH) during the biofilm state compared to the planktonic which is consistent with previous results obtained for *Listeria monocytogenes* and *Pseudomonas aeruginosa* (12,106). Although GAPDH is classified as a tetrameric NAD-binding enzyme involved in glycolysis and gluconeogenesis, there have been numerous reports of this protein being multifunctional and when expressed at the cell surface of Gram-positive bacteria, it appeared to be involved in binding of plasmin, plasminogen and transferrin (107,108). Interestingly coaggregation between *Streptococcus oralis* and *P. gingivalis* 33277 has been shown to be mediated by the interaction of *P. gingivalis* fimbriae and *S. oralis* GAPDH (109). The exact role, if any, of GAPDH in substrate binding in *P. gingivalis* however remains to be answered.

Biofilm Formation

There was a significantly higher abundance of the universal stress protein (UspA) in the planktonic cells as compared to the biofilm cells. The production of UspA) in various bacteria was found to be stimulated by a large variety of conditions, such as entry into stationary phase, starvation of certain nutrients, oxidants and other stimulants (110,111). The increased abundance in planktonic phase cells is consistent with the fact that *P. gingivalis* has evolved to grow as part of a biofilm and that planktonic phases are likely to be more stressful. Expression of UspA in *P. gingivalis* is thought to be related to biofilm formation as inactivation of uspA resulted in the attenuation of early biofilm formation by planktonic cells (112). In this study the biofilm has been established and reached maturation, it therefore appears to have lesser need for UspA as compared to free floating planktonic cells.

A homologue of the internalin family protein InlJ (PG0350) was observed to be higher in abundance during the biofilm state. PG0350 has been shown to be important for biofilm formation in *P. gingivalis* 33277 as gene inactivation resulted in reduced biofilm formation (39). Higher levels of PG0350 in the biofilm could suggest that this protein might be required not just for initial biofilm formation but acts an adhesin that binds *P. gingivalis* to each other or extracellular substrates within the biofilm.

Proteins with Unknown Functions

The largest group of proteins identified in this study was 41 proteins with unknown functions including four proteins that were identified for the first time in this study (Table 2). Of the 41 proteins identified, 37 were predicted to be from the cell envelope and within this group 17 proteins show significant changes between the biofilm and planktonic cells. The majority of these proteins have homology to GenBank proteins with defined names but not well-defined functions. Of particular interest are several proteins that were consistently found to substantially increase in abundance in the biofilm state, namely PG0181, PG0613, PG1304, PG2167 and PG2168.

The above results represent a large scale validation of the $^{16}O/^{18}O$ proteolytic labelling method as applied to a complex mixture, and are the first to use this approach for the comparison of bacterial biofilm and planktonic growth states. A substantial number of proteins with a variety of functions were found to consistently increase or decrease in abundance in the biofilm cells, indicating how the cells adapt to biofilm conditions and also providing potential targets for biofilm control strategies.

EXAMPLES

To help illustrate compositions embodying an aspect of the invention directed to treatment, the following sample formulations are provided.

The following is an example of a toothpaste formulation.

| Ingredient | % w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Biofilm inhibitor (Oxantel pamoate) | 0.2 |
| Water | balance |

The following is an example of a toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Biofilm inhibitor (Oxantel pamoate) | 0.2 |
| Water | balance |

The following is an example of a toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Biofilm inhibitor (Oxantel pamoate) | 0.1 |
| Water | balance |

The following is an example of a toothpaste formulation.

| Ingredient | % w/w |
|---|---|
| Sorbitol | 22.0 |
| Irish moss | 1.0 |

| Ingredient | % w/w |
| --- | --- |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| Biofilm inhibitor (Oxantel pamoate) | 0.3 |
| sodium lauryl sulphate | 2.00 |

The following is an example of a liquid toothpaste formulation.

| Ingredient | % w/w |
| --- | --- |
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Biofilm inhibitor (Oxantel pamoate) | 0.2 |
| Linolic acid | 0.05 |
| Water | balance |

The following is an example of a mouthwash formulation.

| Ingredient | % w/w |
| --- | --- |
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Biofilm inhibitor (Oxantel pamoate) | 0.2 |
| Water | balance |

The following is an example of a mouthwash formulation.

| Ingredient | % w/w |
| --- | --- |
| Gantrez ® S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Biofilm inhibitor (Oxantel pamoate) | 0.3 |
| Water | balance |

The following is an example of a lozenge formulation.

| Ingredient | % w/w |
| --- | --- |
| Sugar | 75-80 |
| Corn syrup | 1-20 |
| Flavour oil | 1-2 |
| NaF | 0.01-0.05 |
| Biofilm inhibitor (Oxantel pamoate) | 0.3 |
| Mg stearate | 1-5 |
| Water | balance |

The following is an example of a gingival massage cream formulation.

| Ingredient | % w/w |
| --- | --- |
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorhexidine gluconate | 0.1 |
| Biofilm inhibitor (Oxantel pamoate) | 0.3 |
| Water | balance |

The following is an example of a periodontal gel formulation.

| Ingredient | % w/w |
| --- | --- |
| Pluronic F127 (from BASF) | 20.0 |
| Stearyl alcohol | 8.0 |
| Oxantel pamoate | 3.0 |
| Colloidal silicon dioxide (such as Aerosil ® 200 ™) | 1.0 |
| Chlorhexidine gluconate | 0.1 |
| Water | balance |

The following is an example of a chewing gum formulation.

| Ingredient | % w/w |
| --- | --- |
| Gum base | 30.0 |
| Calcium carbonate | 2.0 |
| Crystalline sorbitol | 53.0 |
| Glycerine | 0.5 |
| Flavour oil | 0.1 |
| Biofilm inhibitor (Oxantel pamoate) | 0.3 |
| Water | balance |

TABLE 1

Quantification of predetermined BSA ratios using $^{16}O/^{18}O$ proteolytic labelling

| Expected ratio 1:1a) | Triplicate analysis | | | Mean ration (±SD) |
| --- | --- | --- | --- | --- |
| CCTESLVNR | 0.83 | 0.84 | 0.88 | 0.85 ± 0.03 |
| DLGEEHFK | 0.95 | 1.06 | 0.85 | 0.95 ± 0.10 |

TABLE 1-continued

Quantification of predetermined BSA ratios using $^{16}O/^{18}O$ proteolytic labelling

| | | | | |
|---|---|---|---|---|
| EACFKVEGPK | 1.09 | 1.12 | 1.09 | 1.10 ± 0.02 |
| ECCDKPLLEK | 1.01 | 0.96 | 0.87 | 0.94 ± 0.07 |
| EYEATLEECCAK | 1.05 | 1.01 | 1.05 | 1.04 ± 0.02 |
| LVTDLTKVHK | 0.86 | 0.91 | 1.02 | 0.93 ± 0.08 |
| RHPEYAVSVLLR | 1.07 | 0.96 | 0.94 | 0.99 ± 0.07 |
| YICDNQDTISSK | 1.00 | 1.15 | 1.03 | 1.06 ± 0.08 |
| Average | | 0.98 ± 0.10 | 1.00 ± 0.10 0.97 ± 0.09 | 0.98 ± 0.08 |
| Average of all peptidew ID** | | | | 0.98 ± 0.08 |
| CV of all peptides ID | | | | 13.1% |

| | Expected ratio 2:1 b) (18O/16O) | Expected ratio 1:2 b) (18O/16O) | |
|---|---|---|---|
| QTALVELLK | 1.92 | 0.44 (2.27) | 2.10 |
| LVNELTEFAK | 2.45 | 0.46 (2.17) | 2.31 |
| RHPEYAVSVLLR | 1.82 | 0.42 (2.36) | 2.09 |
| LGEYGFQNALIVR | 2.21 | 0.43 (2.31) | 2.26 |
| MPCTEDYLSLILNR | 2.59 | 0.40 (2.50) | 2.55 |
| KVPQVSTPTLVEVSR | 2.35 | 0.39 (2.57) | 2.46 |
| LFTFHADICTLPDTEK | 1.72 | 0.44 (2.27) | 2.00 |
| RPCFSALTPDETYVPK | 1.82 | 0.52 (1.92) | 1.87 |
| Average | 2.11 ± 0.33 | 2.30 ± 0.20 | 2.24 ± 0.24 |
| Average of all peptides ID*** | | | 2.22 ± 0.26 |
| CV of all peptides ID | | | 11.75% |

| Expected ratio 1:5 | | Expected ratio 10:1 | |
|---|---|---|---|
| (18O/16O) | | (18O/16O) | |
| AEFVEVTK | 0.232 (4.32) | AEFVEVTK | 12.38 |
| CCTESLVNR | 0.184 (5.42) | QTAALVELLK | 10.40 |
| SHCIAEVEK | 0.176 (5.67) | LVNELTEFAK | 14.17 |
| ECCDKPLLEK | 0.169 (5.91) | FKDLGEEHFK | 9.41 |
| HPEYAVSVLLR | 0.218 (4.58) | HPEYAVSVLLR | 11.76 |
| YICDNQDTISSK | 0.187 (5.36) | YICDNQDTISSK | 10.16 |
| LKECCDKPLLEK | 0.252 (3.97) | RHPEYAVSVLLR | 10.14 |
| SLHTLFGDELCK | 0.183 (5.45) | SLHTLFGDELCK | 7.58 |
| RHPEYAVSVLLR | 0.201 (4.97) | EYEATLEECCAK | 14.07 |
| VPQVSTPTLVEVSR | 0.206 (4.86) | ETYGDMADCCEK | 12.67 |
| ECCHGDLLECADDR | 0.298 (3.35) | LGEYGFQNALIVR | 9.36 |
| LFTFHADICTLPDTEK | 0.210 (4.76) | VPQVSTPTLVEVSR | 8.34 |
| | | KVPQVSTPTLVEVSR | 8.86 |
| | | LFTFHADICTLPDTEK | 11.08 |
| | | RPCFSALTPDETYVPK | 10.26 |

TABLE 1-continued

Quantification of predetermined BSA ratios using $^{16}O/^{18}O$ proteolytic labelling

| | | |
|---|---|---|
| Average | 0.21 ± 0.04 (4.90 ± 0.75) | 10.74 ± 2.04 |
| CV of all pepides ID | 15.26% | 18.95% | a) For expected ratio of 1:1, only peptides that were identified in all three separate experiments are included in this table
b) For expected ratio of 2:1 and 1:2, only peptides that were identified in both experiments are included in this table
 n = 55  * n = 24

TABLE 2

List of the 81 proteins identified from both biological replicates of the *P. gingivalis* cell envelope fraction. An abundance ratio >1 indicates a higher abundance of the protein in the biofilm with respect to the planktonic state. If the ratio differs from one with more than 3-fold SD (0.26) from the predetermined BSA ratios (>1.78 or <0.56), the proteins were considered to have significantly changed. Based on their mean ratios, proteins highlighted in grey represent significant changes.

| Tigr # | Protein | Loca | Biological replicate 1 | | | | Biological replicate 2 | | | | Total unique peptides | Rank (Group) e |
|---|---|---|---|---|---|---|---|---|---|---|---|---|
| | | | # peptide for quant | Mascot scoreb | Norm Ratio (B/P)c | SEd | # peptide for quant | Mascot score | Norm Ratio (B/P) | SE | | |
| CTD family proteins | | | | | | | | | | | | |
| Proteinases | | | | | | | | | | | | |
| PG0232 | Zinc carboxypeptidase, CPG70 | OM | 13 | 71/20 | 1.67 | 0.08 | 26 | 74/21 | 2.53 | 0.08 | 15 | 3 (DF) |
| PG0553 | Extracellular protease, lysyl endopeptidase precursor (API) | OM/EX | 1 | 65/23 | 3.33 | | 2 | 62/19 | 3.45 | | 2 | 1 (FF) |
| PG1424 | Peptidylarginine deiminase | PP | 9 | 86/22 | 0.49 | 0.05 | 15 | 89/20 | 3.16 | 0.33 | 10 | 4 (BF) |
| PG1837 | Hemagglutinin protein HagA | OM | 3 (15)* | 59/20 | 2.73 | 0.44 | 3 (15)* | 42/21 | 4.21 | 0.36 | 3 | 1 (FF) |
| PG1844 | Lysine-specific cysteine proteinase | OM | 3 (13)* | 78/20 | 0.43 | 0.04 | 9 (24)* | 77/18 | 0.40 | 0.04 | 10 | 1 (BB) |
| PG2024 | Arginine-specific protease ArgI polyprotein (RgpA) | OM | 3 (12)* | 76/22 | 1.63 | 0.10 | 3 (22)* | 72/20 | 3.78 | 0.61 | 4 | 3 (DE) |
| Haem binding | | | | | | | | | | | | |
| PG0616 | Thioredoxin, putative | PP/CY | 14 | 96/20 | 2.23 | 0.20 | 14 | 96/20 | 3.69 | 0.20 | 6 | 2 (EF) |
| Biofilm related | | | | | | | | | | | | |
| PG0350 | Internalin-related protein | OM/EX | 2 | 42/21 | 1.99 | | 2 | 53/21 | 4.27 | | 3 | 2 (EF) |
| Protein with unknown functions | | | | | | | | | | | | |
| PG1798 | Immunoreactive 46 kDa antigen PG99 | PP/EX | 1 | 36/20 | 5.94 | | 1 | 30/21 | 4.07 | | 1 | 1 (FF) |
| PG2216 | Unnamed protein (conserved) | OM/EX | 2 | 36/22 | 0.72 | NA | 4 | 51/21 | 0.68 | 0.06 | 3 | 1 (CC) |
| Transport | | | | | | | | | | | | |
| PG0669 | Haem-binding protein IhtB | OM | 16 | 120/21 | 0.25 | 0.03 | 14 | 69/20 | 0.16 | 0.02 | 6 | 1 (AA) |
| PG0707 | TonB-dependent receptor, P92 | OM | 5 | 110/21 | 0.14 | 0.02 | 30 | 117/20 | 0.31 | 0.04 | 17 | 1 (AA) |
| PG0782 | MotA/TolQ/ExbB proton channel family protein | IM | 7 | 80/19 | 0.86 | 0.14 | 4 | 78/19 | 0.92 | 0.12 | 7 | 1 (CC) |
| PG1006 | Putative TonB dependent receptor | OM/EX | 6 | 59/21 | 1.42 | 0.12 | 9 | 90/20 | 1.50 | 0.11 | 7 | 1 (DD) |
| PG1414 | TonB linked outer membrane receptor, PG47 | OM | 11 | 88/21 | 3.81 | 0.43 | 3 | 49/19 | 3.69 | NA! | 7 | 1 (FF) |
| PG1551 | HmuY protein | UN | 4 | 75/20 | 2.57 | 0.71 | 4 | 74/20 | 2.78 | 0.21 | 1 | 1 (DD) |
| PG1626 | Possible outer membrane-associated protein P58 (putative haem receptor protein) | OM | 41 | 113/21 | 2.37 | 0.22 | 37 | 122/19 | 3.68 | 0.26 | 17 | 2 (EF) |
| PG2008 | TonB-dependent receptor, P90 | OM | 24 | 68/21 | 2.08 | 0.17 | 26 | 112/20 | 3.12 | 0.21 | 20 | 2 (EF) |
| PG0185 | RagA protein | OM | 58 | 89/21 | 0.42 | 0.02 | 109 | 126/20 | 0.79 | 0.04 | 24 | 2 (BC) |
| PG0186 | Lipoprotein RagB | OM | 51 | 142/22 | 0.34 | 0.04 | 56 | 142/19 | 0.26 | 0.02 | 24 | 1 (AA) |
| PG1010 | ABC transporter, ATP-binding protein | IM | 1 | 69/21 | 1.41 | | 2 | 60/19 | 1.26 | | 2 | 1 (DD) |
| PG1762 | Protein-export membrane protein SecD/protein-export membrane protein SecF | IM | 14 | 91/22 | 0.76 | 0.07 | 4 | 99/20 | 0.48 | 0.09 | 10 | 2 (CB) |
| PG2082 | POT family protein | IM | 13 | 75/23 | 0.80 | 0.06 | 6 | 48/22 | 0.52 | 0.10 | 4 | 1 (CC) |
| Iron/haem storage and oxidative stress response | | | | | | | | | | | | |

TABLE 2-continued

List of the 81 proteins identified from both biological replicates of the *P. gingivalis* cell envelope fraction. An abundance ratio >1 indicates a higher abundance of the protein in the biofilm with respect to the planktonic state. If the ratio differs from one with more than 3-fold SD (0.26) from the predetermined BSA ratios (>1.78 or <0.56), the proteins were considered to have significantly changed. Based on their mean ratios, proteins highlighted in grey represent significant changes.

| | | | | | | | | | | |
|---|---|---|---|---|---|---|---|---|---|---|
| PG0090 | Dps family protein | CY | 3 | 72/19 | 1.37 | 0.15 | 1 | 40/21 | 1.27 | | 2 | 1 (DD) |
| PG1286 | Ferritin | CY | 5 | 73/22 | 1.50 | 0.04 | 7 | 124/19 | 2.42 | 0.14 | 3 | 2 (DE) |
| Biofilm and invasion related | | | | | | | | | | | | |
| PG0159 | Endopeptidase PepO | PP/CY | 8 | 122/20 | 0.35 | 0.08 | 3 | 60/19 | 0.18 | NA! | 3 | 2 (BA) |
| PG0245 | Universal stress protein family | CY | 1 | 67/22 | 0.41 | | 2 | 64/20 | 0.25 | | 1 | 2 (BA) |
| PG2132 | Fimbrilin | EX | 1 | 31/22 | 1.14 | | 2 | 66/20 | 0.85 | | 3 | 2 (DC) |
| Energy Metabolism | | | | | | | | | | | | |
| PG0249 | Oxaloacetate decarboxylase, putative | CY | 1 | 44/22 | 3.50 | | 1 | 37/21 | 2.00 | | 1 | 2 (FE) |
| PG0306 | Electron transport complex, RnfABCDGE type, G subunit | PP | 2 | 108/22 | 1.08 | | 1 | 61/19 | 0.72 | | 1 | 2 (DC) |
| PG1084 | Thioredoxin family protein | CY | 2 | 87/22 | 1.07 | | 1 | 132/20 | 0.14 | | 1 | 4 (DA) |
| PG1612 | Methylmalonyl-CoA decarboxylase, alpha subunit (mmdA) | CY | 1 | 65/21 | 0.73 | | 2 | 55/21 | 0.42 | | 1 | 2 (CB) |
| PG1614 | Fumarate reductase, iron-sulfur protein (frdB) | UN | 2 | 60/20 | 0.15 | | 2 | 53/21 | 0.19 | | 2 | 1 (AA) |
| PG1615 | Fumarate reductase, flavoprotein subunit (frdA) | UN | 3 | 58/19 | 0.06 | NA! | 1 | 43/20 | NA** | | 3 | NA |
| PG1704 | Thiol:disulfide interchange protein dsbD, putative | IM | 3 | 64/23 | 2.14 | | 3 | 68/20 | 0.46 | 0.08 | 1 | 4 (EB) |
| PG2181 | NADH:ubiquinone oxidoreductase, Na translocating, B subunit (nqrB) | IM | 1 | 91/21 | 1.32 | | 1 | 69/20 | 0.38 | | 1 | 3 (DB) |
| PG2124 | Glyceraldehyde 3-phosphate dehydrogenase | CY | 3 | 105/22 | 3.39 | 0.62 | 2 | 94/19 | 2.45 | | 3 | 2 (FE) |
| PG2157 | Glutamine cyclotransferase-related protein | PP/EX | 2 | 70/21 | 0.11 | | 3 | 53/20 | 0.45 | NA! | 3 | 2 (AB) |
| Ribosomal proteins | | | | | | | | | | | | |
| PG0167 | Ribosomal protein L25 | CY | 4 | 57/20 | 0.27 | 0.05 | 2 | 50/21 | 0.30 | | 3 | 1 (AA) |
| PG0375 | Ribosomal protein L13 (rpIM) | CY | 2 | 69/21 | 0.28 | | 1 | 116/20 | 0.18 | | 2 | 1 (AA) |
| PG0392 | Ribosomal protein L10 (rpIJ) | CY | 2 | 97/21 | 0.33 | | 5 | 68/22 | 0.37 | 0.02 | 3 | 2 (AB) |
| PG0393 | Ribosomal protein L7/L12 | CY | 6 | 81/20 | 0.68 | 0.03 | 4 | 79/21 | 0.56 | 0.03 | 4 | 2 (CB) |
| Proteins with unknown functions | | | | | | | | | | | | |
| | Integral outer membrane proteins | | | | | | | | | | |
| PG0027 | Probable integral outer membrane protein P40 | OM | 11 | 143/21 | 0.74 | 0.06 | 23 | 111/20 | 0.81 | 0.02 | 11 | 1 (CC) |
| PG0613 | Possible outer membrane associated protein P23 | EX | 3 | 55/19 | 4.41 | | 1 | 43/20 | 3.24 | | 2 | 1 (FF) |
| PG0694 | Outer membrane protein 40 | OM | 37 | 116/20 | 3.62 | 0.56 | 77 | 86/20 | 3.39 | 0.24 | 13 | 1 (FF) |
| PG0695 | Outer membrane protein 41 | OM | 100 | 110/21 | 2.31 | 0.37 | 53 | 124/19 | 3.18 | 0.20 | 19 | 2 (EF) |
| PG1652 | Probable integral outer membrane protein P64 | OM | 2 | 53/20 | 1.04 | 0.21 | 14 | 67/20 | 1.70 | 0.27 | 5 | 2 (CD) |
| PG1786 | Probable integral outer membrane protein P30 | EX/OM | 5 | 56/21 | 0.99 | 0.17 | 5 | 56/26 | 1.33 | 0.08 | 3 | 2 (CD) |
| PG1823 | Probable integral outer membrane protein P20 | PP/OM | 26 | 117/21 | 0.39 | 0.03 | 18 | 91/20 | 0.98 | 0.10 | 7 | 2 (BC) |
| PG2106 | Probable integral outer membrane protein P22 | IM/OM | 15 | 73/20 | 0.31 | 0.04 | 13 | 103/17 | 0.45 | 0.04 | 7 | 2 (AB) |
| | Lipoproteins | | | | | | | | | | |
| PG0188 | Lipoprotein, putative | PP/EX | 7 | 72/23 | 0.92 | 0.09 | 4 | 40/20 | 1.18 | 0.11 | 5 | 2 (CD) |
| PG0241 | Lipoprotein, putative | OM/EX | 4 | 93/20 | 0.45 | 0.08 | 2 | 44/20 | 0.16 | | 3 | 2 (BA) |
| PG0906 | Lipoprotein, putative | PP/CY | 1 | 42/22 | 0.48 | | 5 | 97/20 | 0.40 | 0.05 | 5 | 1 (BB) |

TABLE 2-continued

List of the 81 proteins identified from both biological replicates of the *P. gingivalis* cell envelope fraction. An abundance ratio >1 indicates a higher abundance of the protein in the biofilm with respect to the planktonic state. If the ratio differs from one with more than 3-fold SD (0.26) from the predetermined BSA ratios (>1.78 or <0.56), the proteins were considered to have significantly changed. Based on their mean ratios, proteins highlighted in grey represent significant changes.

| PG2173 | Outer membrane lipoprotein Omp28 | PP/OM | 8 | 109/22 | 0.77 | 0.1 | 12 | 89/18 | 0.71 | 0.04 | 7 | 1 (CC) |
|---|---|---|---|---|---|---|---|---|---|---|---|---|
| | Others proteins | | | | | | | | | | | |
| PG0179 | Unnamed protein (conserved) | PP/EX | 1 | 64/22 | 1.23 | | 1 | 61/19 | 3.55 | | 1 | 3 (DF) |
| PG0181 | Immunoreactive 32 kDa antigen PG49 | PP/OM | 4 | 46/20 | 2.08 | 0.84 | 1 | 31/21 | 3.14 | | 3 | 2 (EF) |
| PG0217f | Unnamed protein | OM | 4 | 74/21 | 1.58 | 0.34 | 7 | 79/18 | 1.78 | 0.07 | 5 | 2 (DE) |
| PG0218 | Unnamed protein | OM | 4 | 61/20 | 2.10 | 0.55 | 11 | 55/20 | 1.59 | 0.17 | 4 | 2 (ED) |
| PG0278f | Unnamed protein | IM/OM | 3 | 77/21 | 1.32 | 0.06 | 7 | 53/20 | 1.90 | 0.21 | 5 | 2 (DE) |
| PG0409 | Unnamed protein (conserved) | PP | 4 | 82/22 | 2.20 | 0.38 | 2 | 69/19 | 2.28 | | 2 | 1 (EE) |
| PG0423 | Unnamed protein (conserved) | CY | 2 | 90/23 | 3.62 | | 1 | 72/21 | 0.68 | | 1 | 4 (FB) |
| PG0452 | Unnamed protein (conserved) | OM | 1 | 53/20 | 0.39 | | 3 | 81/20 | 0.40 | 0.11 | 2 | 1 (BB) |
| PG0448 | Unnamed protein (conserved) | OM | 11 | 74/22 | 1.05 | 0.11 | 10 | 58/20 | 1.44 | 0.08 | 7 | 1 (DD) |
| PG0449 | TPR domain protein | PP | 2 | 68/23 | 1.28 | | 1 | 64/18 | 1.19 | | 1 | 1 (DD) |
| PG0602 | Unnamed protein (conserved) | OM | 3 | 63/21 | 0.65 | 0.07 | 1 | 37/21 | NA** | | 2 | NA |
| PG0914 | Unnamed protein | OM | 1 | 66/21 | 2.23 | | 1 | 27/22 | 2.91 | | 2 | 2 (EF) |
| PG1028 | TPR domain protein | PP | 2 | 78/21 | 0.37 | | 5 | 70/19 | 0.48 | 0.08 | 4 | 1 (BB) |
| PG1035 | Unnamed protein (conserved) | OM | 1 | 42/21 | 0.31 | | 5 | 62/21 | 1.16 | 0.16 | 3 | 4 (AD) |
| PG1304 | Unnamed protein (conserved) | OM | 3 | 52/20 | 2.80 | 1.00 | 1 | 34/20 | 2.93 | | 1 | 2 (EF) |
| PG1356 | Unnamed protein (conserved) | CY | 2 | 60/21 | 0.31 | | 1 | 43/21 | 0.12 | | 2 | 1 (AA) |
| PG1382 | Unnamed protein (conserved) | OM | 3 | 63/21 | 1.89 | 0.29 | 1 | 51/21 | 4.43 | | 2 | 2 (EF) |
| PG1493 | Unnamed protein (conserved) | OM | 6 | 67/22 | 1.85 | 0.15 | 8 | 79/17 | 2.20 | 0.17 | 13 | 1 (EE) |
| PG1621 | Unnamed protein (conserved) | OM | 2 | 51/21 | 1.10 | | 4 | 60/21 | 0.42 | 0.05 | 2 | 2 (CB) |
| PG1648f | Unnamed protein | EX/IM | 1 | 58/22 | 1.25 | | 1 | 73/20 | 0.79 | | 1 | 2 (DC) |
| PG1715 | Unnamed protein (conserved) | OM | 4 | 51/20 | 1.10 | 0.04 | 13 | 71/20 | 0.97 | 0.14 | 3 | 2 (DC) |
| PG1881 | Unnamed protein (conserved) | OM | 2 | 49/22 | 0.61 | | 4 | 48/19 | 0.82 | 0.16 | 3 | 1 (CC) |
| PG1889f | Unnamed protein | CY | 12 | 99/20 | 0.16 | 0.02 | 8 | 85/20 | 0.25 | 0.03 | 6 | 1 (AA) |
| PG2049 | Unnamed protein | IM/CY | 3 | 48/21 | 0.63 | 0.06 | 1 | 27/21 | 0.82 | | 1 | 1 (CC) |
| PG2167 | Immunoreactive 53 kDa antigen PG123 | OM | 7 | 64/20 | 2.84 | 0.73 | 4 | 45/20 | 2.26 | 0.06 | 3 | 1 (EE) |
| PG2168 | Unnamed protein (conserved) | UN | 3 | 47/21 | 4.90 | 1.97 | 4 | 74/21 | 2.04 | 0.14 | 4 | 2 (FE) |
| PG2174 | Unnamed protein (conserved) | OM | 5 | 58/21 | 0.78 | 0.06 | 15 | 102/21 | 0.37 | 0.04 | 7 | 2 (CB) |

[a]Locations as determined by the CELLO program; EX: Extracellular, OM: Outer membrane, IM: Inner membrane, PP: Periplasm, CY: Cytoplasm; UN: Unknown

[b]Maximum Mascot peptide ion score/identity threshold

[c]Normalized ratio; B = biofilm, P = Planktonic, Normalization process as described in experimental procedures

[d]SE = Standard error of the mean

[e]Ranking and grouping as decribed in FIG. 4B

[f]Proteins identified only in this study

!SE measurements not carried out due to unresolved/overlapping of one of the 3 peptides

*Due to presence of identical peptides between these proteins, ratios derived were from peptides that were unique to these proteins only. Values in parenthesis are total number of peptides matched.

**Due to unresolved/overlapping peaks

TABLE 3

Proteomic and transcriptomic analyses of genes products involved in glutamate/aspartate catabolism in *P. gingivalis* during growth in heme-limitation compared to heme-excess. Shading indicates proteins that are predicted to be encoded in operons.

| No | Tigr Acc# | Protein and peptide sequence identified | Score[1] | N[2] | n-ICAT[3] | Protein Fold change[4] | SD(±) | Transcriptomics Fold Change | Transcriptomics P-value |
|---|---|---|---|---|---|---|---|---|---|
| 1 | PG0329 | Formiminotransferase-cyclodeaminase-related protein | 30/14 | 2 | 1 | 2.9 | - | NS[5] | |
| | | • IMEX*VPNFSEGR | | | | | | | |
| 2 | PG0548 | Pyruvate ferredoxin/flavodoxin oxidoreductase family protein | 33/15 | 1 | 1 | 2.0 | - | NS | |
| | | • IAGELLPC*VFHVSAR | | | | | | | |
| 3 | PG0687 | Succinate-semialdehyde dehydrogenase | | 27 | 6 | 4.0 | 1.6 | 1.77 | 0.066 |
| | | • AFDNGIIC*SGEQSIIYNEADK | 37/18 | | | | | | |
| | | • C*SAHAVR | 22/16 | | | | | | |
| | | • EYQATHNQEAVDNIC*R | 18/13 | | | | | | |
| | | • GVGAEDVIC*K | 43/13 | | | | | | |
| | | • NHGAYFC*DEAEGDR | 53/14 | | | | | | |
| | | • TC*NAIIIAPHPR | 66/13 | | | | | | |
| 4 | PG0689 | NAD-dependent 4-hydroxy-butyrated dehydrogenase | | 12 | 3 | 2.8 | 0.8 | 1.93 | 8.892 E-05 |
| | | • ELIIVPTTC*GTGSEVTNISIAEIK | 35/19 | | | | | | |
| | | • ILNC*QPEYVYPK | 41/18 | | | | | | |
| | | • LDELLGC*LLTK | 35/14 | | | | | | |
| 5 | PG0690 | [6] 4-hydroxybutyrate CoA transferase | | | | | | 3.31 | 0.03 |
| 6 | PG0691 | [6] NifU-like protein | | | | | | 1.60 | 0.0002 |
| 7 | PG0692 | 4-hydroxybutyryl-CoA dehydratase | | 5 | 2 | 2.9 | 0.7 | 1.65 | 0.054 |
| | | • AGNYMIDLLLANVC*K | 42/15 | | | | | | |
| | | • TASC*FQR | 20/15 | | | | | | |
| 8 | PG1067 | Hypothetical protein | | 2 | 2 | 1.7 | 0.1 | NS | |
| | | • TDISESAADVLDEPIVVC*R | 64/14 | | | | | | |
| 9 | PG1068 | Conserved hypothetical protein | | 3 | 2 | 1.7 | 0.1 | NS | |
| | | • MIITAAIC*GAEVLK | 40/12 | | | | | | |
| | | • AVC*PDVIIQPSTGGAVGMTNDER | 38/15 | | | | | | |
| 10 | PG1075 | [6] Butyrate-acetoacetate CoA transferase | | | | | | 1.4 | 0.05 |
| 11 | PG1076 | Acyl-CoA dehydrogenase short-chain specific | | 3 | 2 | 1.8 | 0.2 | NS | |
| | | • LYC*AETAMDMTTK | 26/14 | | | | | | |
| | | • SIAQFQNTQFQLADLQC*R | 23/19 | | | | | | |
| 12 | PG1078 | Electron transfer flavoprotein, alpha subunit | | 5 | 2 | 2.0 | 0.4 | NS | |
| | | • VTAILC*GYK | 22/15 | | | | | | |
| | | • TGLTADC*TSLEIGDER | 55/15 | | | | | | |

TABLE 3-continued

Proteomic and transcriptomic analyses of genes products involved in glutamate/aspartate catabolism in *P. gingivalis* during growth in heme-limitation compared to heme-excess. Shading indicates proteins that are predicted to be encoded in operons.

| # | Gene | Protein/Peptide | Score | [2] | [3] | [4] | | [5] |
|---|------|-----------------|-------|-----|-----|-----|---|-----|
| 13 | PG1079[6] | Enoyl-CoA | | | | 1.3 | | 0.04 |
| 14 | PG1081 | Acetate kinase | | 9 | 3 | 3.5 | 0.9 | NS |
| | | •VLVLNC*GSSSVK | 42/14 | | | | | |
| | | •AC*EILGLDYDK | 29/15 | | | | | |
| | | •VEEC*IPLAPLHNPANIK | 42/14 | | | | | |
| 15 | PG1082 | Phosphotransacetylase | | 5 | 2 | 4.4 | 1.6 | NS |
| | | •AAELVENPLYLGC*LIVK | 52/15 | | | | | |
| | | •GC*SVEDIYR | 45/15 | | | | | |
| 16 | PG1232 | Glutamate dehydrogenase, NAD-specific | | 10 | 2 | 2.3 | 1.2 | NS |
| | | •C*MLDLR | 28/14 | | | | | |
| | | •LRPESTGFGAVYFVQNMC*K | 54/15 | | | | | |
| 17 | PG1271 | Ornithine aminotransferase | | 3 | 2 | 0.09 | - | NS |
| | | •AVIIVC*DGNFHGR | 42/19 | | | | | |
| | | •YFDFLSAYSAVNQGHC*HPK | 32/19 | | | | | |
| 18 | PG1417 | Fumarate hydratase class I, anaerobic | | 3 | 2 | 1.0 | 0.2 | NS |
| | | •GQLPFC*QDTGTAIILGK | 57/15 | | | | | |
| | | •HGASC*PVGMGVSC*SADR | 18/16 | | | | | |
| 19 | PG1612 | Methylmalonyl-CoA decarboxylase, alpha subunit | | 2 | 2 | 2.4 | - | NS |
| | | •FNGQSVGIVANQPQVMAGC*LDSNASR | 28/14 | | | | | |
| | | •C*TNFGIDK | 21/15 | | | | | |
| 20 | PG1614 | Fumarate reductase, iron-sulfur protein (FrdB) | | 6 | 2 | 0.25 | 0.1 | NS |
| | | •MDELGFGNC*TNTR | 45/15 | | | | | |
| | | •APVVFDHDC*R | 36/13 | | | | | |
| 21 | PG1615 | Fumarate reductase, flavoprotein subunit (FrdA) | | 1 | 1 | 0.35 | - | NS |
| | | •LAEVSNAIIDQC*VAQGVPFAR | 29/14 | | | | | |
| 22 | PG1741 | Aspartate ammonia-lyase | | 4 | 2 | 1.0 | 0.2 | NS |
| | | •C*GLHEFNLPAMQPGSSIMPGK | 24/14 | | | | | |
| | | •VNPVIPEVMNQIC*YK | 20/15 | | | | | |
| 23 | PG1810 | 2-oxoglutarate oxidoreductase, beta subunit | | 5 | 2 | 2.0 | 0.4 | NS |
| | | •IADMLALLDGTC*LVTR | 54/16 | | | | | |
| 24 | PG1949 | Malate dehydrogenase | | 3 | 1 | 1.0 | 0.2 | NS |
| | | •LTPNLC*LYDPFAVGLEGVAEEIR | 35/15 | | | | | |

[1]Highest scoring peptide score/threshold score (P = 0.05)
[2]Total number of independent peptide identification events for each protein
[3]Number of unique ICAT-labelled peptides identified for each protein
[4]Average ratios of all quantified peptides for each protein in fold change (Heme-limitation/excess)
[5]NS no statistically significant change detected
[6]Only identified in the microarray analysis
C* Denotes ICAT-modified cysteine

TABLE 4

The 24 *P. gingivalis* polypeptides selected as targets for inhibition of biofilm formation.

| Tigr # | Protein | Predicted location | Ratio (B/P) Biol Rep 1 | Ratio (B/P) Biol Rep 2 | Rank (Group) | Accession Number* | Accession Number Version |
|---|---|---|---|---|---|---|---|
| CTD family proteins | | | | | | | |
| PG0232 | Zinc carboxypeptidase, CPG70 | OM | 1.67 | 2.53 | 3 (DF) | AAQ65462 | AAQ65462.1 |
| PG0553 | Extracellular protease, lysyl endopeptidase precursor (API) | OM/EX | 3.33 | 3.45 | 1 (FF) | AAQ65742 | AAQ65742.1 |
| PG2024 | Arginine-specific protease ArgI polyprotein (RgpA) | OM | 1.63 | 3.78 | 3 (DE) | AAQ66991 | AAQ66991.1 |
| Haem binding | | | | | | | |
| PG0616 | Thioredoxin, putative | PP/CY | 2.23 | 3.69 | 2 (EF) | AAQ65800 | AAQ65800.1 |
| Biofilm related | | | | | | | |
| PG0350 | Internalin-related protein | OM/EX | 1.99 | 4.27 | 2 (EF) | AAQ65561 | AAQ65561.1 |
| Adhesins | | | | | | | |
| PG1837 | Hemagglutinin protein HagA | OM | 2.73 | 4.21 | 1 (FF) | AAQ66831 | AAQ66831.1 |
| Proteins with unknown functions | | | | | | | |
| PG1798 | Immunoreactive 46 kDa antigen PG99 | PP/EX | 5.94 | 4.07 | 1 (FF) | AAQ66797 | AAQ66797.1 |
| Transport | | | | | | | |
| PG1414 | TonB linked outer membrane receptor, PG47 | OM | 3.81 | 3.69 | 1 (FF) | AAQ66469 | AAQ66469.1 |
| PG1551 | HmuY protein | OM | 2.57 | 2.78 | 1 (DD) | AAQ66587 | AAQ66587.1 |
| PG1626 | Possible outer membrane-associated protein P58 (putative haem receptor protein) | OM | 2.37 | 3.68 | 2 (EF) | AAQ66654 | AAQ66654.1 |
| PG2008 | TonB-dependent receptor, P90 | OM | 2.08 | 3.12 | 2 (EF) | AAQ66977 | AAQ66977.1 |
| Proteins with unknown functions | | | | | | | |
| Integral outer membrane proteins | | | | | | | |
| PG0613 | Possible outer membrane associated protein P23 | EX | 4.41 | 3.24 | 1 (FF) | AAQ65797 | AAQ65797.1 |
| PG0694 | Outer membrane protein 40 | OM | 3.62 | 3.39 | 1 (FF) | AAQ65867 | AAQ65867.1 |
| PG0695 | Outer membrane protein 41 | OM | 2.31 | 3.18 | 2 (EF) | AAQ65868 | AAQ65868.1 |
| Others proteins | | | | | | | |
| PG0181 | Immunoreactive 32 kDa antigen PG49 | PP/OM | 2.08 | 3.14 | 2 (EF) | AAQ65416 | AAQ65416.1 |
| PG0218 | Unnamed protein | OM | 2.10 | 1.59 | 2 (ED) | AAQ65449 | AAQ65449.1 |
| PG0914 | Unnamed protein | OM | 2.23 | 2.91 | 2 (EF) | AAQ66051 | AAQ66051.1 |
| PG1304 | Unnamed protein (conserved) | OM | 2.80 | 2.93 | 2 (EF) | AAQ66377 | AAQ66377.1 |
| PG1382 | Unnamed protein (conserved) | OM | 1.89 | 4.43 | 2 (EF) | AAQ66444 | AAQ66444.1 |
| PG1493 | Unnamed protein (conserved) | OM | 1.85 | 2.20 | 1 (EE) | AAQ66538 | AAQ66538.1 |
| PG2167 | Immunoreactive 53 kDa antigen PG123 | OM | 2.84 | 2.26 | 1 (EE) | AAQ67117 | AAQ67117.1 |
| PG2168 | Unnamed protein (conserved) | UN | 4.90 | 2.04 | 2 (FE) | AAQ67118 | AAQ67118.1 |
| Energy Metabolism | | | | | | | |
| PG1614 | Fumarate reductase, iron-sulfur protein (frdB) | UN | 0.15 | 0.19 | 1 (AA) | AAQ66642 | AAQ66642.1 |
| PG1615 | Fumarate reductase, flavoprotein subunit (frdA) | UN | 0.06 | | NA | AAQ66643 | AAQ66643.1 |

*These accession numbers provide a sequence for the *P. gingivalis* proteins referred to in the specification. Sequences corresponding to the accession numbers are incorporated by reference.

TABLE 5

Proteomic and transcriptomic analyses of *P. gingivalis* grown in heme-limitation compared to heme-excess.
Shading indicates proteins that are predicted to be encoded in operons.

| No | Tigr Acc# | Protein and peptide sequence identified | Score[1] | N[2] | n-ICAT[3] | Proteomics Fold change[4] | SD(±) | Transcriptomics Fold Change | Transcriptomics P-value |
|---|---|---|---|---|---|---|---|---|---|
| Iron transport and related proteins | | | | | | | | | |
| 13 | PG0644[6] | HtrE (tia) TonB-linked receptor | | | | | | 2.05 | 1.54E-04 |
| 18 | PG1552 | HmuR | | 1 | 1 | 4.0 | - | 3.13 | 0.003 |
| | | •MNSDELFEEITYPGYTIC*R | 25/15 | | | | | | |
| 21 | PG1019 | Hypothetical protein | | 2 | 1 | 25.0 | - | 2.57 | 0.003 |
| | | •TYMIDTNDSENDC*IAR | 70/14 | | | | | | |
| 22 | PG1020[6] | Conserved hypothetical protein; possible outer membrane receptor protein | | | | | | 3.36 | 3.0E-04 |
| Others | | | | | | | | | |
| 33 | PG1874[6] | Conserved hypothetical protein | | 1 | 1 | 4.0 | - | 1.52 | 0.05 |
| 34 | PG1875[6] | Hemolysin A | | | | | | 1.40 | 0.05 |

[1] Highest scoring peptide score/threshold score (P = 0.05)
[2] Total number of independent peptide identification events for each protein
[3] Number of unique ICAT-labelled peptides identified for each protein
[4] Average ratios of all quantified peptides for each protein in fold change (Heme-limitation/excess)
[5] NS no statistically significant change detected
[6] Only identified in the microarray analysis
C* Denotes ICAT-modified cysteine

TABLE 6

Effect of adding Oxantel to 16 h *P. gingivalis* biofilm as determined using COMSTAT on a 3-channel flow cell system.

| | Biological Replicate 1 | | | | Biological Replicate 2 | | | |
|---|---|---|---|---|---|---|---|---|
| | Control | 12.5 µM | % reduction | 125 µM | % reduction | Control | 12.5 µM | 12.5 µM | % reduction |
| Total biomass (µm³/µm²) | 1.80 | 1.26[a] | 30.1 | 1.00[a] | 44.4 | 2.68 | 1.451[a] | 1.621[a] | 42.8 |
| Surface to biovolume ratio (µm²/µm³) | 1.50 | 2.04[a] | | 2.27[b] | | 1.86 | 2.331[a] | 2.541[a] | |
| Average thickness (µm) | 1.16 | 0.70[a] | 39.7 | 0.43[a] | 63.2 | 1.80 | 0.911[a] | 0.81[a] | 49.9 |
| Ave microcolonies (by pixel, minimum 500) | 21.2 | 17.4 | | 20.8 | | 24.8 | 18.4 | 19.2 | |
| Average microcolony area (µm²) | 235.26 | 147.65[a] | 37.2 | 115.42[a] | 50.94 | 180.62 | 119.571[a] | 104.881[a] | 37.9 |

[1] Percentage reduction based on average of both replicates over the control sample.
[a] P <0.01 compared to Control
[b] P <0.05 compared to Control

TABLE 7

Effect of oxantel, morantel or Thiabendazole on growth of *P. gingivalis* W50 over 50 h

| | MIC | MGT h⁻¹ (DMSO) | MGT h⁻¹ (31.25 µM) | MGT h⁻¹ (62.5 µM) |
|---|---|---|---|---|
| Oxantel | 112 µM | 6.62 | 19.28 | 23.77 |
| Morantel | 2800 µM | 6.85 | 10.97 | 11.28 |
| Thiabendazole | >3 mM* | 6.25 | 6.80 | 6.22 |

*MIC at higher concentrations were not able to be determined due to the insolubility of thiabendazole at >3 mM.

TABLE 8

Effect of Oxantel on growth of *P. gingivalis* ATCC 33277 over 50 h

| | MIC | MGT h⁻¹ (DMSO) | MGT h⁻¹ (31.25 µM) | MGT h⁻¹ (62.5 µM) |
|---|---|---|---|---|
| Oxantel | 125 µM | 6.62 | 10.0 | 24.0 |

REFERENCES

1. Costerton, J. W., Lewandowski, Z., Caldwell, D. E., Korber, D. R., and Lappin-Scott, H. M. (1995) *Annu. Rev. Microbiol.* 49, 711-745
2. Cvitkovitch, D. G., Li, Y. H., and Ellen, R. P. (2003) *J. Clin. Invest.* 112(11), 1626-1632
3. Cochrane, D. M., Brown, M. R., Anwar, H., Weller, P. H., Lam, K., and Costerton, J. W. (1988) *J. Med. Microbiol.* 27(4), 255-261
4. van Steenbergen, T. J., Kastelein, P., Touw, J. J., and de Graaff, J. (1982) *J. Periodontal Res.* 17(1), 41-49
5. Neiders, M. E., Chen, P. B., Suido, H., Reynolds, H. S., Zambon, J. J., Shlossman, M., and Genco, R. J. (1989) *J. Periodontal Res.* 24(3), 192-198
6. Griffen, A. L., Becker, M. R., Lyons, S. R., Moeschberger, M. L., and Leys, E. J. (1998) *J. Clin. Microbiol.* 36(11), 3239-3242
7. Cutler, C. W., Arnold, R. R., and Schenkein, H. A. (1993) *J. Immunol.* 151(12), 7016-7029

8. Chen, T., Hosogi, Y., Nishikawa, K., Abbey, K., Fleischmann, R. D., Walling, J., and Duncan, M. J. (2004) *J. Bacteriol.* 186(16), 5473-5479
9. Davey, M. E. (2006) *Periodontol.* 2000 42, 27-35
10. Orme, R., Douglas, C. W., Rimmer, S., and Webb, M. (2006) *Proteomics* 6(15), 4269-4277
11. Rathsam, C., Eaton, R. E., Simpson, C. L., Browne, G. V., Valova, V. A., Harty, D. W., and Jacques, N. A. (2005) *J Proteome Res* 4(6), 2161-2173
12. Sauer, K., Camper, A. K., Ehrlich, G. D., Costerton, J. W., and Davies, D. G. *J. Bacteriol.* 184(4), 1140-1154
13. Ong, S. E., and Mann, M. (2005) *Nat. Chem. Biol.* 1(5), 252-262
14. Bender, M. L., and Kemp, K. C. (1957) *J. Am. Chem. Soc* 79, 116
15. Schnolzer, M., Jedrzejewski, P., and Lehmann, W. D. (1996) *Electrophoresis* 17(5), 945-953
16. Yao, X., Freas, A., Ramirez, J., Demirev, P. A., and Fenselau, C. (2001) *Anal Chem* 73(13), 2836-2842
17. Blonder, J., Hale, M. L., Chan, K. C., Yu, L. R., Lucas, D. A., Conrads, T. P., Zhou, M., Popoff, M. R., Issaq, H. J., Stiles, B. G., and Veenstra, T. D. (2005) *J. Proteome Res* 4(2), 523-531
18. Qian, W. J., Monroe, M. E., Liu, T., Jacobs, J. M., Anderson, G. A., Shen, Y., Moore, R. J., Anderson, D. J., Zhang, R., Calvano, S. E., Lowry, S. F., Xiao, W., Moldawer, L. L., Davis, R. W., Tompkins, R. G., Camp, D. G., 2nd, and Smith, R. D. (2005) *Mol. Cell. Proteomics* 4(5), 700-709
19. Zang, L., Palmer Toy, D., Hancock, W. S., Sgroi, D. C., and Karger, B. L. (2004) *J. Proteome Res.* 3(3), 604-612
20. Kuster, B., and Mann, M. (1999) *Anal. Chem.* 71(7), 1431-1440
21. Takao, T., Hori, H., Okamoto, K., Harada, A., Kamachi, M., and Shimonishi, Y. *Rapid Commun. Mass Spectrom.* 5(7), 312-315
22. Shevchenko, A., Chernushevich, I., Ens, W., Standing, K. G., Thomson, B., Wilm, M., and Mann, M. (1997) *Rapid Commun. Mass Spectrom.* 11(9), 1015-1024
23. Gevaert, K., Staes, A., Van Damme, J., De Groot, S., Hugelier, K., Demol, H., Martens, L., Goethals, M., and Vandekerckhove, J. (2005) *Proteomics* 5(14), 3589-3599
24. Chen, X., Cushman, S. W., Pannell, L. K., and Hess, S. (2005) *J. Proteome Res.* 4(2), 570-577
25. Stockwin, L. H., Blonder, J., Bumke, M. A., Lucas, D. A., Chan, K. C., Conrads, T. P., Issaq, H. J., Veenstra, T. D., Newton, D. L., and Rybak, S. M. (2006) *J. Proteome Res.* 5(11), 2996-3007
26. Lane, C. S., Wang, Y., Betts, R., Griffiths, W. J., and Patterson, L. H. (2007) *Mol. Cell Proteomics*
27. Korbel, S., Schumann, M., Bittorf, T., and Krause, E. (2005) *Rapid Comm. Mass Spectrom.* 19(16), 2259-2271
28. Bantscheff, M., Dumpelfeld, B., and Kuster, B. (2004) *Rapid Commun. Mass. Spectrom.* 18(8), 869-876
29. Jia, J. Y., Lamer, S., Schumann, M., Schmidt, M. R., Krause, E., and Haucke, V. (2006) *Mol. Cell Proteomics* 5(11), 2060-2071
30. Miyagi, M., and Rao, K. C. (2007) *Mass Spectrom. Rev* 26(1), 121-136
31. Veith, P. D., Talbo, G. H., Slakeski, N., Dashper, S. G., Moore, C., Paolini, R. A., and Reynolds, E. C. (2002) *Biochem. J.* 363(Pt 1), 105-115
32. Qian, W. J., Liu, T., Monroe, M. E., Strittmatter, E. F., Jacobs, J. M., Kangas, L. J., Petritis, K., Camp, D. G., 2nd, and Smith, R. D. (2005) *J. Proteome Res* 4(1), 53-62
33. Perkins, D. N., Pappin, D. J., Creasy, D. M., and Cottrell, J. S. (1999) *Electrophoresis* 20(18), 3551-3567
34. Xia, Q., Hendrickson, E. L., Zhang, Y., Wang, T., Taub, F., Moore, B. C., Porat, I., Whitman, W. B., Hackett, M., and Leigh, J. A. (2006) *Mol. Cell. Proteomics* 5(5), 868-881
35. Quackenbush, J. (2001) *Nat. Rev. Genet.* 2(6), 418-427
36. Yu, C. S., Chen, Y. C., Lu, C. H., and Hwang, J. K. (2006) *Proteins* 64(3), 643-651
37. Richardson, A. J., Calder, A. G., and Stewart, C. S. (1989) *Letters in Applied Microbiology* 9, 5-8
38. O'Toole, G. A., and Kolter, R. (1998) *Mol Microbiol* 28(3), 449-461
39. Capestany, C. A., Kuboniwa, M., Jung, I. Y., Park, Y., Tribble, G. D., and Lamont, R. J. (2006) *Infect. Immun.* 74(5), 3002-3005
40. Lopez-Ferrer, D., Ramos-Fernandez, A., Martinez-Bartolome, S., Garcia-Ruiz, P., and Vazquez, J. (2006) *Proteomics* 6 Suppl 1, S4-S11
41. Staes, A., Demol, H., Van Damme, J., Martens, L., Vandekerckhove, J., and Gevaert, K. (2004) *J Proteome Res* 3(4), 786-791
42. Patwardhan, A. J., Strittmatter, E. F., Camp, D. G., 2nd, Smith, R. D., and Pallavicini, M. G. (2006) *Proteomics* 6(9), 2903-2915
43. Smalley, J. W., Birss, A. J., McKee, A. S., and Marsh, P. D. (1993) *J Gen Microbiol* 139(9), 2145-2150
44. McKee, A. S., McDermid, A. S., Baskerville, A., Dowsett, A. B., Ellwood, D. C., and Marsh, P. D. (1986) *Infect. Immun.* 52(2), 349-355
45. Dashper, S. G., Butler, C. A., Lissel, J. P., Paolini, R. A., Hoffmann, B., Veith, P. D., O'Brien-Simpson, N. M., Snelgrove, S. L., Tsiros, J. T., and Reynolds, E. C. *J. Biol. Chem.* 280(30), 28095-28102
46. Li, J., Steen, H., and Gygi, S. P. (2003) *Mol. Cell. Proteomics* 2(11), 1198-1204
47. Dashper, S. G., Brownfield, L., Slakeski, N., Zilm, P. S., Rogers, A. H., and Reynolds, E. C. (2001) *J. Bacteriol.* 183(14), 4142-4148
48. Hoskisson, P. A., and Hobbs, G. (2005) *Microbiology* 151(Pt 10), 3153-3159
49. Piper, M. D., Daran-Lapujade, P., Bro, C., Regenberg, B., Knudsen, S., Nielsen, J., and Pronk, J. T. (2002) *J. Biol. Chem.* 277(40), 37001-37008
50. Siroy, A., Cosette, P., Seyer, D., Lemaitre-Guillier, C., Vallenet, D., Van Dorsselaer, A., Boyer-Mariotte, S., Jouenne, T., and De, E. (2006) *J. Proteome Res.* 5(12), 3385-3398
51. Hood, B. L., Lucas, D. A., Kim, G., Chan, K. C., Blonder, J., Issaq, H. J., Veenstra, T. D., Conrads, T. P., Pollet, I., and Karsan, A. (2005) *J Am Soc Mass Spectrom* 16(8), 1221-1230
52. Yao, X., Afonso, C., and Fenselau, C. (2003) *J Proteome Res* 2(2), 147-152
53. Eckel-Passow, J. E., Oberg, A. L., Therneau, T. M., Mason, C. J., Mahoney, D. W., Johnson, K. L., Olson, J. E., and Bergen, H. R., 3rd. (2006) *Bioinformatics* 22(22), 2739-2745
54. Storms, H. F., van der Heijden, R., Tjaden, U. R., and van der Greet J. (2006) *Rapid Commun. Mass Spectrom.* 20(23), 3491-3497
55. Zenobi, R., and Knochenmuss, R. (1998) *Mass Spectrom. Rev.* 17(5), 337-366
56. Seers, C. A., Slakeski, N., Veith, P. D., Nikolof, T., Chen, Y. Y., Dashper, S. G., and Reynolds, E. C. (2006) *J. Bacteriol.* 188(17), 6376-6386
57. Curtis, M. A., Kuramitsu, H. K., Lantz, M., Macrina, F. L., Nakayama, K., Potempa, J., Reynolds, E. C., and Aduse-Opoku, J. (1999) *J. Periodontal Res.* 34(8), 464-472

58. O'Brien-Simpson, N. M., Paolini, R. A., Hoffmann, B., Slakeski, N., Dashper, S. G., and Reynolds, E. C. (2001) *Infect. Immun.* 69(12), 7527-7534
59. O'Brien-Simpson, N. M., Veith, P. D., Dashper, S. G., and Reynolds, E. C. (2003) *Curr. Protein Pept. Sci.* 4(6), 409-426
60. Abe, N., Kadowaki, T., Okamoto, K., Nakayama, K., Ohishi, M., and Yamamoto, K. (1998) *J. Biochem.* (Tokyo) 123(2), 305-312
61. Potempa, J., Pike, R., and Travis, J. (1995) *Infect. Immun.* 63(4), 1176-1182
62. Pathirana, R. D., O'Brien-Simpson, N. M., Brammar, G. C., Slakeski, N., and Reynolds, E. C. (2007) *Infect. Immun.* 75(3), 1436-1442
63. Chen, Y. Y., Cross, K. J., Paolini, R. A., Fielding, J. E., Slakeski, N., and Reynolds, E. C. (2002) *J. Biol. Chem.* 277(26), 23433-23440
64. Zhang, Y., Wang, T., Chen, W., Yilmaz, O., Park, Y., Jung, I. Y., Hackett, M., and Lamont, R. J. (2005) *Proteomics* 5(1), 198-211
65. Sato, K., Sakai, E., Veith, P. D., Shoji, M., Kikuchi, Y., Yukitake, H., Ohara, N., Naito, M., Okamoto, K., Reynolds, E. C., and Nakayama, K. (2005) *J. Biol. Chem.* 280(10), 8668-8677
66. Nguyen, K. A., Travis, J., and Potempa, J. (2007) *J. Bacteriol.* 189(3), 833-843
67. Dashper, S. G., Cross, K. J., Slakeski, N., Lissel, P., Aulakh, P., Moore, C., and Reynolds, E. C. (2004) *Oral Microbiol. Immunol.* 19(1), 50-56
68. Lewis, J. P., Dawson, J. A., Hannis, J. C., Muddiman, D., and Macrina, F. L. (1999) *J. Bacteriol.* 181(16), 4905-4913
69. Shi, Y., Ratnayake, D. B., Okamoto, K., Abe, N., Yamamoto, K., and Nakayama, K. (1999) *J. Biol. Chem.* 274(25), 17955-17960
70. Sroka, A., Sztukowska, M., Potempa, J., Travis, J., and Genco, C. A. (2001) *J. Bacteriol.* 183(19), 5609-5616
71. Simpson, W., Olczak, T., and Genco, C. A. (2000) *J Bacteriol* 182(20), 5737-5748
72. Lewis, J. P., Plata, K., Yu, F., Rosato, A., and Anaya, C. (2006) *Microbiology* 152(Pt 11), 3367-3382
73. Olczak, T., Siudeja, K., and Olczak, M. (2006) *Protein Expr. Purif.* 49(2), 299-306
74. Olczak, T., Simpson, W., Liu, X., and Genco, C. A. (2005) *FEMS Microbiol. Rev.* 29(1), 119-144
75. Veith, P. D., Chen, Y. Y., and Reynolds, E. C. (2004) *Infect. Immun.* 72(6), 3655-3657
76. Shibata, Y., Hiratsuka, K., Hayakawa, M., Shiroza, T., Takiguchi, H., Nagatsuka, Y., and Abiko, Y. (2003) *Biochem. Biophys. Res. Commun.* 300(2), 351-356
77. Tatusov, R. L., Fedorova, N. D., Jackson, J. D., Jacobs, A. R., Kiryutin, B., Koonin, E. V., Krylov, D. M., Mazumder, R., Mekhedov, S. L., Nikolskaya, A. N., Rao, B. S., Smirnov, S., Sverdlov, A. V., Vasudevan, S., Wolf, Y. I., Yin, J. J., and Natale, D. A. (2003) *BMC Bioinformatics* 4, 41
78. Ratnayake, D. B., Wai, S, N., Shi, Y., Amako, K., Nakayama, H., and Nakayama, K. (2000) *Microbiology* 146 1119-1127
79. Smalley, J. W., Birss, A. J., McKee, A. S., and Marsh, P. D. (1991) *FEMS Microbiol. Lett.* 69(1), 63-67
80. Dashper, S. G., Hendtlass, A., Slakeski, N., Jackson, C., Cross, K. J., Brownfield, L., Hamilton, R., Barr, I., and Reynolds, E. C. (2000) *J Bacteriol* 182(22), 6456-6462
81. Takahashi, N., Sato, T., and Yamada, T. (2000) *J. Bacteriol.* 182(17), 4704-4710
82. Takahashi, N., and Sato, T. (2001) *J Dent Res* 80(5), 1425-1429
83. Litwin, C. M., and Calderwood, S. B. (1993) *Clin Microbiol Rev* 6(2), 137-149
84. Gygi, S. P., Rochon, Y., Franza, B. R., and Aebersold, R. (1999) *Mol. Cell. Biol.* 19(3), 1720-1730
85. Baughn, A. D., and Malamy, M. H. (2003) *Microbiology* 149(Pt 6), 1551-1558
86. Macy, J., Probst, I., and Gottschalk, G. (1975) *J Bacteriol* 123(2), 436-442
87. Baughn, A. D., and Malamy, M. H. (2002) *Proc Natl Acad Sci USA* 99(7), 4662-4667
88. Mayrand, D., and McBride, B. C. (1980) *Infect Immun* 27(1), 44-50
89. Smith, M. A., Mendz, G. L., Jorgensen, M. A., and Hazell, S. L. (1999) *Int J Biochem Cell Biol* 31(9), 961-975
90. Kroger, A., Geisler, V., Lemma, E., Theis, F., and Lenger, R. (1992) *Archives of Microbiology* 158(5), 311-314
91. Shah, H., and Williams, R. (1987) *Current Microbiology* 15, 241-246
92. Klein, R. A., Linstead, D. J., and Wheeler, M. V. (1975) *Parasitology* 71(1), 93-107
93. Turrens, J. F. (1989) *Biochem J* 259(2), 363-368
94. Mendz, G. L., Hazell, S. L., and Srinivasan, S. (1995) *Arch Biochem Biophys* 321(1), 153-159
95. Mendz, G. L., Meek, D. J., and Hazell, S. L. (1998) *J Membr Biol* 165(1), 65-76
96. Mileni, M., MacMillan, F., Tziatzios, C., Zwicker, K., Haas, A. H., Mantele, W., Simon, J., and Lancaster, C. R. (2006) *Biochem J* 395(1), 191-201
97. Nealson, K., and D, S. (1994) *Annual review of microbiology* 48, 311-343
98. Sellars, M. J., Hall, S. J., and Kelly, D. J. (2002) *J Bacteriol* 184(15), 4187-4196
99. O'Toole, G. A., Gibbs, K. A., Hager, P. W., Phibbs, P. V., Jr., and Kolter, R. (2000) *J Bacteriol* 182(2), 425-431
100. Whiteley, M., Bangera, M. G., Bumgarner, R. E., Parsek, M. R., Teitzel, G. M., Lory, S., and Greenberg, E. P. (2001) *Nature* 413(6858), 860-864
101. Romeo, T., Gong, M., Liu, M. Y., and Brun-Zinkernagel, A. M. (1993) *J Bacteriol* 175(15), 4744-4755
102. Sabnis, N. A., Yang, H., and Romeo, T. (1995) *J Biol Chem* 270(49), 29096-29104
103. Mercante, J., Suzuki, K., Cheng, X., Babitzke, P., and Romeo, T. (2006) *J Biol Chem* 281(42), 31832-31842
104. Altier, C., Suyemoto, M., and Lawhon, S. D. (2000) *Infect Immun* 68(12), 6790-6797
105. Lawhon, S. D., Frye, J. G., Suyemoto, M., Porwollik, S., McClelland, M., and Altier, C. (2003) *Mol Microbiol* 48(6), 1633-1645
106. Hefford, M. A., D'Aoust, S., Cyr, T. D., Austin, J. W., Sanders, G., Kheradpir, E., and Kalmokoff, M. L. (2005) *Can. J. Microbiol.* 51(3), 197-208
107. Pancholi, V., and Fischetti, V. A. (1992) *J. Exp. Med.* 176(2), 415-426
108. Taylor, J. M., and Heinrichs, D. E. (2002) *Mol. Microbiol.* 43(6), 1603-1614
109. Maeda, K., Nagata, H., Yamamoto, Y., Tanaka, M., Tanaka, J., Minamino, N., and Shizukuishi, S. (2004) *Infect. Immun.* 72(3), 1341-1348
110. Gustaysson, N., Diez, A., and Nystrom, T. (2002) *Mol. Microbiol.* 43(1), 107-117
111. Kvint, K., Nachin, L., Diez, A., and Nystrom, T. (2003) *Curr. Opin. Microbiol.* 6(2), 140-145
112. Kuramitsu, H. K., Chen, W., and Ikegami, A. (2005) *J. Periodontol.* 76(11 Suppl), 2047-2051

The invention claimed is:

1. A method of inhibiting or reducing a *P. gingivalis* biofilm in a subject comprising administering to the subject a pharmaceutical composition comprising an inhibiting agent, wherein the inhibiting agent is selected from the group consisting of oxantel, morantel or thiabendazole.

2. The method of claim 1, wherein the inhibiting agent is oxantel.

3. The method of claim 1, wherein the inhibiting agent is morantel.

4. The method of claim 1, wherein the inhibiting agent is thiabendazole.

* * * * *